United States Patent
Wirtz et al.

(10) Patent No.: US 8,934,698 B2
(45) Date of Patent: Jan. 13, 2015

(54) SYSTEM AND DEVICE FOR CHARACTERIZING CELLS

(75) Inventors: Denis Gaston Wirtz, Washington, DC (US); Pei-Hsun Wu, Towson, MD (US); Shyam Bharat Khatau, Baltimore, MD (US); Wei-Chiang Chen, Baltimore, MD (US); Jude Marvin George Phillip, Jr., Washington, DC (US); Zev Ari Binder, Baltimore, MD (US); Yiider Tseng, Gainesville, FL (US)

(73) Assignees: The Johns Hopkins University, Baltimore, MD (US); University of Florida, Gainesville, FL (US)

( * ) Notice: Subject to any disclaimer, the term of this patent is extended or adjusted under 35 U.S.C. 154(b) by 112 days.

(21) Appl. No.: 13/530,772

(22) Filed: Jun. 22, 2012

(65) Prior Publication Data

US 2013/0071003 A1    Mar. 21, 2013

Related U.S. Application Data

(60) Provisional application No. 61/499,955, filed on Jun. 22, 2011, provisional application No. 61/500,234, filed on Jun. 23, 2011, provisional application No. 61/500,244, filed on Jun. 23, 2011, provisional application No. 61/533,446, filed on Sep. 12, 2011, provisional application No. 61/645,930, filed on May 11, 2012.

(51) Int. Cl.
*G06K 9/00* (2006.01)
*G06T 7/00* (2006.01)
*G06K 9/38* (2006.01)

(52) U.S. Cl.
CPC .......... *G06K 9/00127* (2013.01); *G06T 7/0012* (2013.01); *G06K 9/00134* (2013.01); *G06K 9/00147* (2013.01); *G06K 9/38* (2013.01); *G06T 2207/10056* (2013.01); *G06T 2207/30024* (2013.01)
USPC .......................................................... 382/133

(58) Field of Classification Search
None
See application file for complete search history.

(56) References Cited

U.S. PATENT DOCUMENTS 5,843,644 A * 12/1998 Liotta et al. .................. 435/6.12
5,991,028 A * 11/1999 Cabib et al. .................. 356/456

(Continued)

OTHER PUBLICATIONS

Assoian, "Anchorage-dependent Cell Cycle Progression," *The Journal of Cell Biology* 136, 1-4 (1997).

(Continued)

*Primary Examiner* — Shervin Nakhjavan
(74) *Attorney, Agent, or Firm* — Venable LLP; Henry J Daley; Miguel A. Lopez

(57) ABSTRACT

A diagnostic device includes a microscope configured to obtain image data on a plurality of cells and a computing device. The computing device is configured to receive the image data, identify at least a portion of each of the plurality of cells based on the received image data, determine at least one of a value of a morphological parameter for each identified at least a portion of the plurality of cells or a relative organization among the identified at least a portion of the plurality of cells, and calculate statistics for the plurality of cells based on the at least one of the determined values of the morphological parameter or the determined relative organization, the statistics including information suitable for distinguishing metastatic cells from non-metastatic cells. The diagnostic device further includes an output device configured to output the statistics for diagnosis.

13 Claims, 39 Drawing Sheets

(56) References Cited

U.S. PATENT DOCUMENTS

| | | | |
|---|---|---|---|
| 6,134,354 A * | 10/2000 | Lee et al. | 382/270 |
| 6,771,803 B1 * | 8/2004 | Turek et al. | 382/131 |
| 7,461,048 B2 * | 12/2008 | Teverovskiy et al. | 706/62 |
| 8,060,348 B2 * | 11/2011 | Cline et al. | 703/2 |
| 8,144,966 B2 * | 3/2012 | Provenzano et al. | 382/133 |
| 8,559,693 B2 * | 10/2013 | MacAulay et al. | 382/133 |
| 8,611,620 B2 * | 12/2013 | Karasikov et al. | 382/128 |
| 2002/0028460 A1 * | 3/2002 | Pinkel et al. | 435/6 |
| 2002/0186875 A1 * | 12/2002 | Burmer et al. | 382/133 |
| 2003/0021457 A1 * | 1/2003 | Kirk et al. | 382/133 |
| 2003/0023385 A1 * | 1/2003 | Lazaridis | 702/19 |
| 2004/0038406 A1 * | 2/2004 | Unger et al. | 435/459 |
| 2004/0114800 A1 * | 6/2004 | Ponomarev et al. | 382/173 |
| 2004/0117124 A1 | 6/2004 | Kiros et al. | |
| 2005/0265588 A1 * | 12/2005 | Gholap et al. | 382/128 |
| 2006/0014137 A1 * | 1/2006 | Ghosh et al. | 435/4 |
| 2006/0120580 A1 * | 6/2006 | Makram-Ebeid et al. | 382/128 |
| 2006/0188140 A1 * | 8/2006 | Gholap et al. | 382/133 |
| 2006/0210962 A1 | 9/2006 | Imaizumi et al. | |
| 2008/0212867 A1 * | 9/2008 | Provenzano et al. | 382/133 |
| 2008/0248499 A1 | 10/2008 | Chiu et al. | |
| 2008/0317325 A1 * | 12/2008 | Ortyn et al. | 382/133 |
| 2009/0072171 A1 | 3/2009 | So et al. | |
| 2009/0232381 A1 | 9/2009 | Matsunaga et al. | |
| 2010/0290692 A1 * | 11/2010 | Macaulay et al. | 382/133 |
| 2010/0317002 A1 * | 12/2010 | Daniely et al. | 435/6 |
| 2011/0274337 A1 * | 11/2011 | Hunter et al. | 382/133 |
| 2012/0002852 A1 * | 1/2012 | Karasikov et al. | 382/128 |
| 2013/0201317 A1 * | 8/2013 | Ortyn et al. | 348/77 |
| 2013/0252888 A1 * | 9/2013 | Jiang | 514/8.5 |

OTHER PUBLICATIONS

Ballabeni et al., "Cell cycle adaptations of embryonic stem cells," *Proceedings of the National Academy of Sciences* (2011).

Benecke et al., "The control of mRNA production, translation and turnover in suspended and reattached anchorage-dependent fibroblasts," *Cell* 14, 931-939 (1978).

Cooper et al., "Rethinking synchronization of mammalian cells for cell cycle analysis," *Cellular and Molecular Life Sciences* 60, 1099-1106 (2003).

Cooper et al., "Nocodazole does not synchronize cells: implications for cell-cycle control and whole-culture synchronization," *Cell and Tissue Research* 324, 237-242 (2006).

Darzynkiewicz et al., "Bivariate Analysis of DNA Content and Expression of Cyclin Proteins," in Current Protocols in Cytometry (John Wiley & Sons, Inc., 2001).

Dechat et al., "Alterations in mitosis and cell cycle progression caused by a mutant lamin A known to accelerate human aging," *Proceedings of the National Academy of Sciences* 104, 4955-4960 (2007).

Dorner et al., "Lamina-associated polypeptide 2α regulates cell cycle progression and differentiation via the retinoblastoma-E2F pathway," *The Journal of Cell Biology* 173, 83-93 (2006).

Folkman et al., "Role of cell shape in growth control," *Nature* 273, 345-349 (1978).

Hale et al., "Dysfunctional Connections Between the Nucleus and the Actin and Microtubule Networks in Laminopathic Models," *Biophysical Journal* 95, 5462-5475 (2008).

Harper, "Synchronization of Cell Populations in G1/S and G2/M Phases of the Cell Cycle," in *Methods in Molecular Biology*, vol. 296 157-166 (2004).

Hartwell et al., "Cell cycle control and cancer," *Science* 266, 1821-1828 (1994).

Jayat et al., "Cell cycle analysis by flow cytometry: Principles and applications," *Biology of the Cell* 78, 15-25 (1993).

Johnson et al., "A-type lamins regulate retinoblastoma protein function by promoting subnuclear localization and preventing proteasomal degradation," *Proceedings of the National Academy of Sciences of the United States of America* 101, 9677-9682 (2004).

Kastan et al., "Cell-cycle checkpoints and cancer," *Nature* 432, 316-323 (2004).

Keyomarsi et al., "Redundant cyclin overexpression and gene amplification in breast cancer cells," *Proceedings of the National Academy of Sciences* 90, 1112-1116 (1993).

Khatau et al., "A perinuclear actin cap regulates nuclear shape," *Proceedings of the National Academy of Sciences* 106, 19017-19022 (2009).

Klein et al., "Cell-Cycle Control by Physiological Matrix Elasticity and In Vivo Tissue Stiffening," *Current Biology* 19, 1511-1518 (2009).

Kues et al. "Cell Cycle Synchronization of Porcine Fetal Fibroblasts: Effects of Serum Deprivation and Reversible Cell Cycle Inhibitors," *Biology of Reproduction* 62, 412-419 (2000).

Maeshima et al., "Cell-cycle-dependent dynamics of nuclear pores: pore-free islands and lamins," *Journal of Cell Science* 119, 4442-4451 (2006).

Moseley et al., "Cdk1 and cell morphology: connections and directions," *Current Opinion in Cell Biology* 21, 82-88 (2009).

Ng et al. "Laser excitation power and the flow cytometric resolution of complex karyotypes," *Cytometry Part A* 77A, 585-588 (2010).

Polyak et al., "p27Kip1, a cyclin-Cdk inhibitor, links transforming growth factor-beta and contact inhibition to cell cycle arrest," *Genes & Development* 8, 9-22 (1994).

Salpingidou et al., "A novel role for the nuclear membrane protein emerin in association of the centrosome to the outer nuclear membrane," *The Journal of Cell Biology* 178, 897-904 (2007).

Sherr, "Cancer Cell Cycles," *Science* 274, 1672-1677 (1996).

Soni et al., "Selective In Vivo and In Vitro Effects of a Small Molecule Inhibitor of Cyclin-Dependent Kinase 4," *Journal of the National Cancer Institute* 93, 436-446 (2001).

Stewart-Hutchinson et al., "Structural requirements for the assembly of LINC complexes and their function in cellular mechanical stiffness," *Experimental Cell Research* 314, 1892-1905 (2008).

Tobey et al., "Synchronization of human diploid fibroblasts at multiple stages of the cell cycle," *Experimental Cell Research* 179, 400-416 (1988).

van den Heuvel et al., "Distinct roles for cyclin-dependent kinases in cell cycle control," *Science* 262, 2050-2054 (1993).

Wang et al., "Neural cell cycle dysregulation and central nervous system diseases," *Progress in Neurobiology* 89, 1-17 (2009).

Wu et al., "A general method for improving spatial resolution by optimization of electron multiplication in CCD imaging," *Opt. Express* 18, 5199-5212 (2010).

Wu et al., "Cell cycle-dependent alteration in NAC1 nuclear body dynamics and morphology," *Physical Biology* 8, 015005 (2011).

International Search Report in PCT/US2012/043826 dated Nov. 28, 2012.

Written Opinion of the International Searching Authrotityin PCT/US2012/043286 dated Nov. 26, 2012.

* cited by examiner

SYSTEM AND DEVICE FOR CHARACTERIZING CELLS

CROSS-REFERENCE OF RELATED APPLICATION

This application claims priority to U.S. Provisional Application No. 61/499,955 filed Jun. 22, 2011, U.S. Provisional Application No. 61/500,234 filed Jun. 23, 2011, U.S. Provisional Application No. 61/500,244 filed Jun. 23, 2011, U.S. Provisional Application No. 61/533,446 filed Sep. 12, 2011, and U.S. Provisional Application No. 61/645,930 filed on May 11, 2012, which are hereby incorporated by reference in their entireties.

This invention was made with Government support of Grant No. 54 CA-143868, awarded by the National Institute of Health/National Cancer Institute. The U.S. Government has certain rights in this invention.

BACKGROUND

1. Field of Invention

The currently claimed embodiments of this invention relate to analyzing cells.

2. Discussion of Related Art

The contents of all references, including articles, published patent applications and patents referred to anywhere in this specification are hereby incorporated by reference.

Ninety percent of cancer-related deaths are caused by metastatic disease, i.e. the spreading of a subset of cells from a primary tumor in an organ to distal sites in other organs. However, despite research efforts, no reliable genetic, epigenetic, or proteomic signature of cancer metastasis has been identified so far. In particular, a recent systematic genetic analysis of cells from primary pancreatic tumors of early-stage patients and liver metastatic sites of late-stage patients, while displaying shared signaling pathways, revealed highly heterogeneous genetic mutational sets, potentially limiting the ability of genetic profiling to stage tumors and predict clinical outcomes. Traditional efforts in cancer diagnostics and prognosis have focused on identifying molecular signatures of metastatic disease (e.g. over-expression of prostate-specific antigen (PSA) in prostate cancer, expression of cell receptor HER2 in breast cancer, degree of DNA methylation in ovarian cancer, mutation in KRAS in colorectal cancer, etc.), which too often fail to usefully or reliably recommend courses of therapy and/or predict clinical outcomes.

There is thus a need for improved analyzing of cells.

SUMMARY

A diagnostic device according to an embodiment of the current invention includes a microscope configured to obtain image data on a plurality of cells and a computing device. The computing device is configured to receive the image data, identify at least a portion of each of the plurality of cells based on the received image data, determine at least one of a value of a morphological parameter for each identified at least a portion of the plurality of cells or a relative organization among the identified at least a portion of the plurality of cells, and calculate statistics for the plurality of cells based on the at least one of the determined values of the morphological parameter or the determined relative organization, the statistics including information suitable for distinguishing metastatic cells from non-metastatic cells. The diagnostic device further includes an output device configured to output the statistics for diagnosis.

A method of characterizing a plurality of cells according to an embodiment of the current invention includes receiving image data of a plurality of cells, identifying at least a portion of each of the plurality of cells in the received image data, determining at least one of a value of a morphological parameter for each identified at least a portion of each of the plurality of cells or a relative organization among the identified at least a portion of each of the plurality of cells, calculating statistics for the plurality of cells based on the at least one of the determined values of the morphological parameter or the determined relative organization, the statistics including information suitable for distinguishing metastatic cells from non-metastatic cells, and outputting the statistics for diagnosis.

One or more tangible non-transitory computer-readable storage media for storing computer-executable instructions executable by processing logic, the media according to an embodiment of the current invention storing one or more instructions. The one or more instructions for receiving image data of a plurality of cells, identifying at least a portion of each of the plurality of cells in the received image data, determining at least one of a value of a morphological parameter for each identified at least a portion of each of the plurality of cells or a relative organization among the identified at least a portion of each of the plurality of cells, calculating statistics for the plurality of cells based on the at least one of the determined values of the morphological parameter or the determined relative organization, the statistics including information suitable for distinguishing metastatic cells from non-metastatic cells, and outputting the statistics for diagnosis.

A microscopy device according to an embodiment of the current invention includes a microscope configured to obtain image data on a plurality of cells in different cell cycle phases on a substrate and a computing device. The computing device is configured to receive the image data, normalize the received image data, identify at least a portion of each of the plurality of cells based on the normalized image data, determine a value of a morphological parameter for each identified at least a portion of each of the plurality of cells, and determine values of the morphological parameter for corresponding cell cycle phases and fractions of the plurality of cells in the corresponding cell cycle phases based on the determined value of the morphological parameter for each identified at least a portion of each of the plurality of cells. The microscopy device further includes an output device configured to output the values of the morphological parameter for corresponding cell cycle phases and fractions of the plurality of cells in the corresponding cell cycle phases.

A method for determining morphological parameters of a plurality of cells according to an embodiment of the present invention includes receiving image data on the plurality of cells in different cell cycle phases on a substrate, normalizing the received image data, identifying at least a portion of each of the plurality of cells based on the normalized image data, determining a value of a morphological parameter for each identified at least a portion of each of the plurality of cells, determining values of the morphological parameter for corresponding cell cycle phases and fractions of the plurality of cells in the corresponding cell cycle phases based on the determined value of the morphological parameter for each identified at least a portion of each of the plurality of cells, and outputting the values of the morphological parameter for corresponding cell cycle phases and fractions of the plurality of cells in the corresponding cell cycle phases.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

Figure 1:
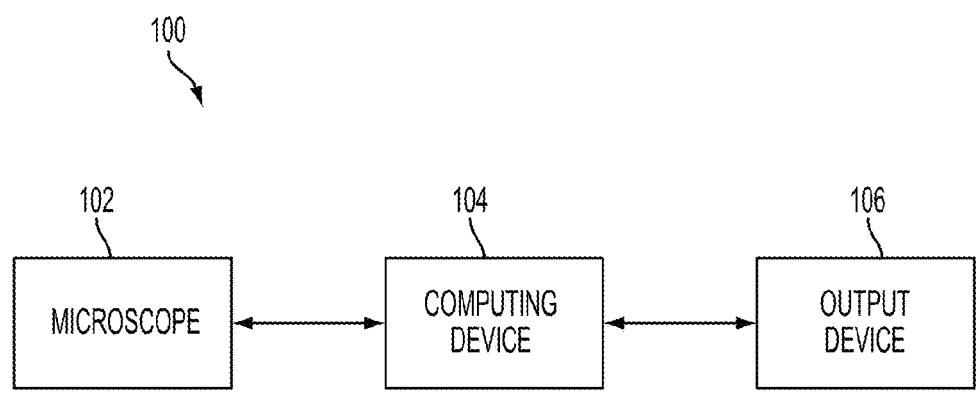
FIG. 1 illustrates a block diagram of a system according to an embodiment of the current invention.

FIG. 1 illustrates a block diagram of system 100 according to an embodiment of the current invention. System 100 may include microscope 102, computing device 104, and output device 106. Microscope 102 may be configured to obtain image data on a plurality of cells. Microscope 102 may include a camera, a motorized stage, and motorized excitation and emission filters. The image data obtained by microscope 102 may be a plurality of images of a cell sample. For a given field of view in the plurality of images, the plurality of images may include an image using different fluorescence channels under the same field of view. For example, images may be taken for fields of view of a 9 by 9 grid of a sample, where for each of the 81 fields of view, an image is taken corresponding to a fluorescence channels corresponding to ultraviolet (UV), red fluorescent protein (RFP), green fluorescent protein (GFP), and Cy5, and one phase-contrast channel. The camera may capture image data, the motorized stage may move the sample to each of the fields of view, and the motorized excitation and emission filters may control the current channel shown in the image.

Computing device 104 may be a device operable to perform computations, for example, a computer or a processor. Computing device 104 is in communication with microscope 102 and is configured to receive image data obtained by microscope 102. Computing device 104 is configured to use the received image data of a plurality of cells and calculate statistics for the plurality of cells in the image data. Statistics may include information suitable for distinguishing metastatic cells from non-metastatic cells. For example, computing device 104 may output the likelihood that one or more cells in the plurality of cells are cancerous or information on the cells that a doctor may use to determine the likelihood that one or more cells in the plurality of cells.

Output device 106 may be a device configured to output the statistics for diagnosis. Output device 106 may in communication with computing device 104 and may receive the statistics from computing device 104. Output device 106 may output the statistics visually, aurally, or tacitilely. For example, output device 106 may be a liquid crystal display monitor coupled to computing device 104.

Microscope 102, computing device 104, and output device 106 may be separate devices, a single integrated device, or a combination of separate devices and integrated devices. Imaging device 102, imaging device model source 104, component model source 106, processor 108, and display device 110 may be in communication via a network (e.g., an intranet or the Internet) or via circuitry within one or more integrated devices.

Figure 2:
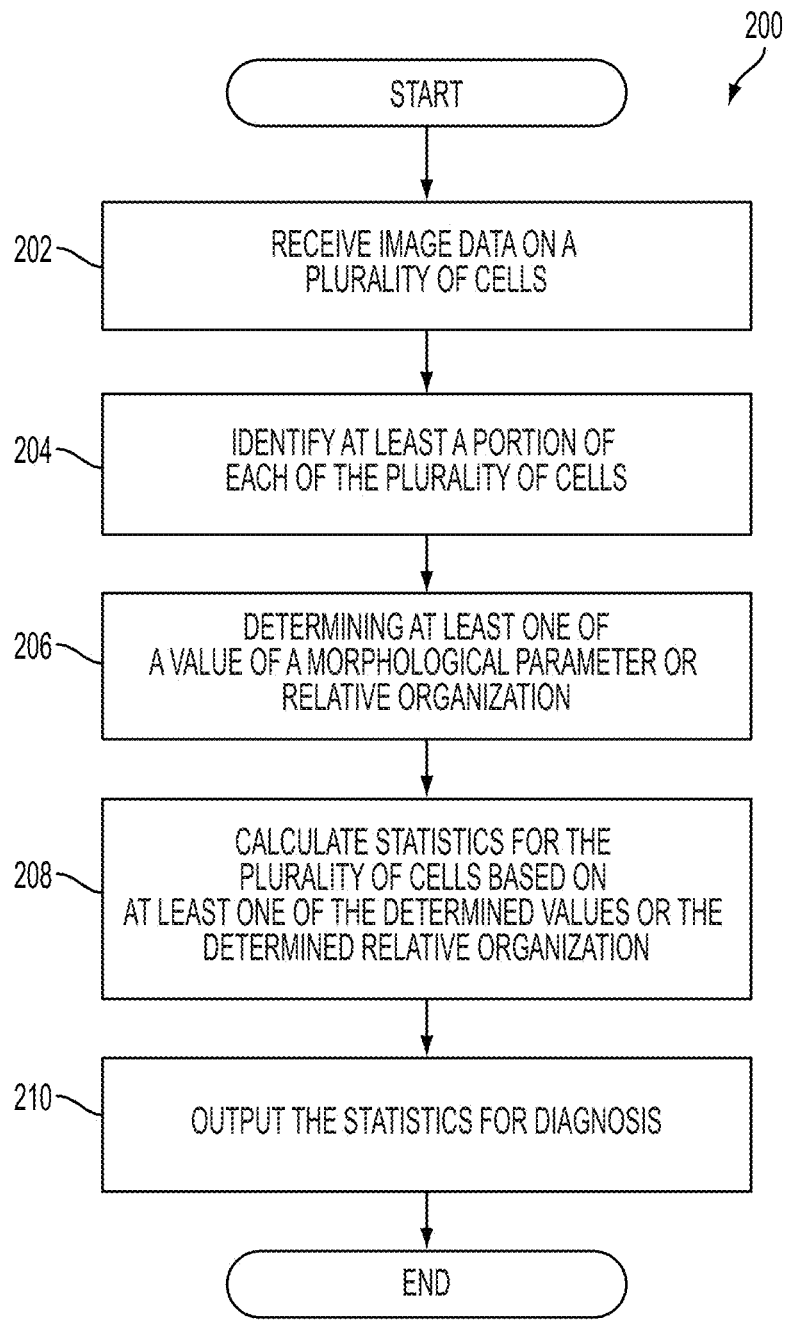
FIG. 2 illustrates an exemplary process flowchart for outputting statistics for diagnosis according to an embodiment of the current invention.

FIG. 2 illustrates an exemplary process flowchart for outputting statistics for diagnosis according to an embodiment of the current invention.

Initially, computing device 104 may receive image data on a plurality of cells from microscope 102 (block 202). The image data may correspond to image data captured based on the microscope example described above.

Computing device 104 may identify at least a portion of each of the plurality of cells in the received image data (block 204). A portion of the plurality of cells may correspond with at least one of the nucleus of cells, the cell boundaries of cells, another part of the cells, or the entire cell. Identification of a portion of each of the plurality of cells may be based on cell segmentation, explained in greater detail in FIG. 3 below.

Computing device 104 may determine at least one of a value of a morphological parameter for each identified at least a portion of the plurality of cells or a relative organization among the identified at least a portion of the plurality of cells (block 206). A morphological parameter may be a parameter regarding the shape of the cell, shape of the nucleus within the cell, or shape of other parts of the cell. For example, a morphological parameter may be associated with perimeter, long axis length, short axis length, orientation, solidity, equivalent diameter, aspect ratio, circularity, roundness, roughness, curvature, nucleus:cytoplasm ratio, and relative nuclear location. Relative organization among the identified at least a portion of the plurality of cells may be the density, structural arrangement, etc.

Computing device 104 may determine a value of the morphological parameter for each identified at least a portion of the plurality of cells based on estimated boundaries of the cell or portion of the cell. Roughness may be defined by transforming the two dimensional boundary of each cell and nucleus into a corresponding one dimensional curve. Curvature may be defined by convolving object boundary coordinates. Relative nuclear location may be characterized using a polar coordinate system with an origin at the center of the nucleus where the angle and distance corresponds to the distance to the cell boundary at each angle. Computing device 104 may determine the relative organization among the identified at least a portion of the plurality of cells based on the relative locations of at least one of the nuclei or cell boundaries of the plurality of cells.

Computing device 104 may calculate statistics for the plurality of cells based on the at least one of the determined values of the morphological parameter or the determined relative organization (block 208). The statistics may be associated with mean, median, mode, max, min, standard deviation, skewness, kurtosis, gini, entropy, or summation for the various morphological parameters of the plurality of cells, or density, structural arrangement, etc. of the plurality of cells.

Computing device 104 may output the statistics for a user, e.g., a doctor, to make a diagnosis based on the statistics. For example, a doctor may determine that the standard deviation in roughness indicates that the cells are metastatic cells. Computing device 104 may also calculate further statistics regarding the likelihood that cells are cancerous based on the statistics for the morphological parameters. For example, computing device 104 may calculate a likelihood of cancer based on the deviation of the morphological parameter statistics from non-cancerous cells or similarity of morphological parameter statistics with cancerous cells.

Computing device 104 may also calculate the likelihood cells in the plurality of cells are metastatic based on the density of the plurality of cells. For example, if the number of cells in a volume is higher than a threshold, the computing device 104 may determine there is a high likelihood the cells are metastatic. Computing device 104 may further determine likelihood based on training data. System 100 may be provided non-cancerous cells and cancerous cells so that computing device 104 may develop a model by which to more accurately determine if cells are cancerous. The statistics calculated by computing device 104 are not limited to use in diagnosis of cancer. For example, the statistics can be used for diagnosing genetic disorders, etc.

Figure 3:
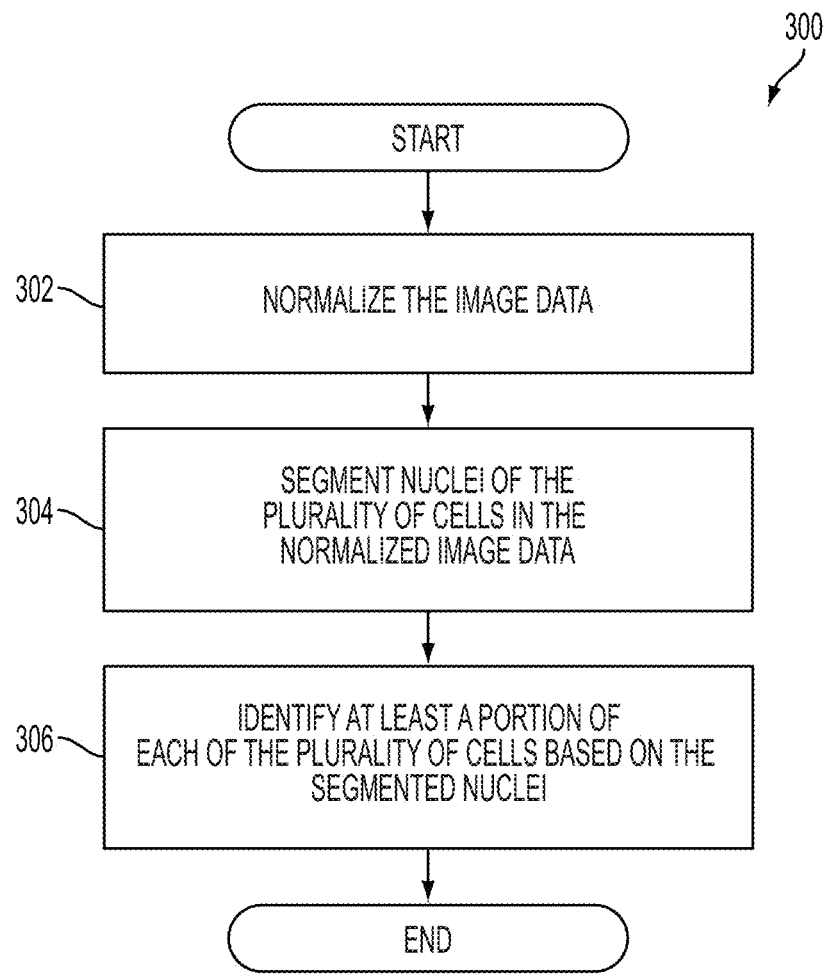
FIG. 3 illustrates an exemplary process flowchart for identifying at least a portion of each cell according to an embodiment of the current invention.

FIG. 3 illustrates an exemplary process flowchart for identifying at least a portion of each cell according to an embodiment of the current invention. Computing device 104 may normalize the image data received from microscope 102 (block 302). Computing device 104 may normalize the image based on intensity to account for fluctuations in intensity caused by errors. For example, the light source illuminating the cells may not provide uniform lighting on the cells, the lens of microscope 102 may be dirty causing reduction in intensity received by a camera in microscope 102, the lens of the camera of microscope 102 may be dirty, the intensity detector of the camera of microscope 102 maybe malfunctioning, etc.

Computing device 104 may segment nuclei of the cells in the normalized image data (block 304). For example, computing device 104 may use normalized image data corresponding to a UV channel and/or a blue filter in which cells are stained with Hoescht stain. Hoescht stains bind to deoxyribonucleic acid (DNA), which within cells is generally most prevalent within the nucleus. Areas with intense fluorescence may be identified and determined to be separate nuclei of cells and segmented based on the determination.

Computing device 104 may identify at least a portion of each of the plurality of cells based on the segmented nuclei (block 306). For example, computing device 104 may compare the locations of nuclei and the locations of cells to identify individual cells that correspond to locations of segmented nuclei and locations of segmented cells.

Figure 4:
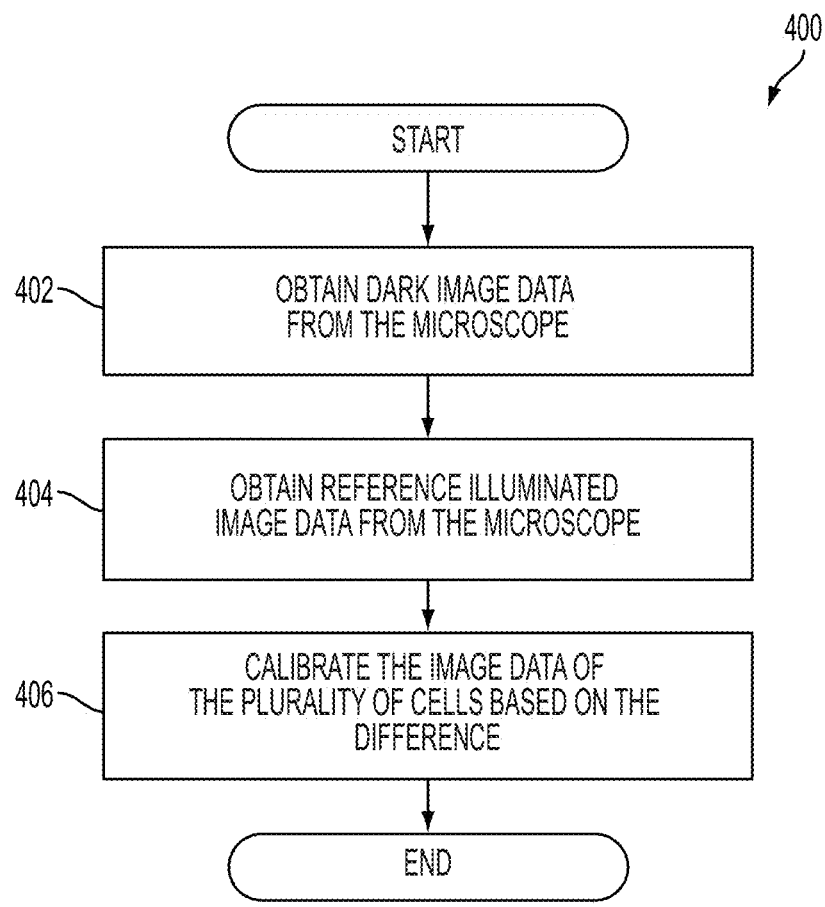
FIG. 4 illustrates an exemplary process flowchart for normalizing image data according to an embodiment of the current invention.

FIG. 4 illustrates an exemplary process flowchart for normalizing image data according to an embodiment of the current invention. Computing device 104 may obtain dark image data from the microscope 102 (block 402). Dark image data may be image data where no fluorescence is expected so that the intensities captured by in the dark image data are at minimum intensity.

Computing device 104 may obtain reference illuminated image data from microscope 102 (block 404). Reference illuminated data may be image data where the maximum intensity is captured. For example, a fluorescent sample may be prepared where the entire sample is stained to fluoresce. Computing device 104 may convert all image data to grayscale where each pixel corresponds to an intensity of light.

Computing device 104 may calibrate image data of the plurality of cells based on the difference between the intensities in dark image data and the reference illuminated image data. For example, computing device 104 may create normalized image data based on the following equation, $I_c = I_r - I_{offset}/(I_{ill} - I_{offset}) * \langle (I_{ill} - I_{offset}) \rangle$, where $I_c$ corresponds to the corrected image, $I_r$ corresponds to the original image, $I_{offset}$ corresponds to the dark image data, and $I_{ill}$ corresponds to the reference illuminated image data.

Figure 5:
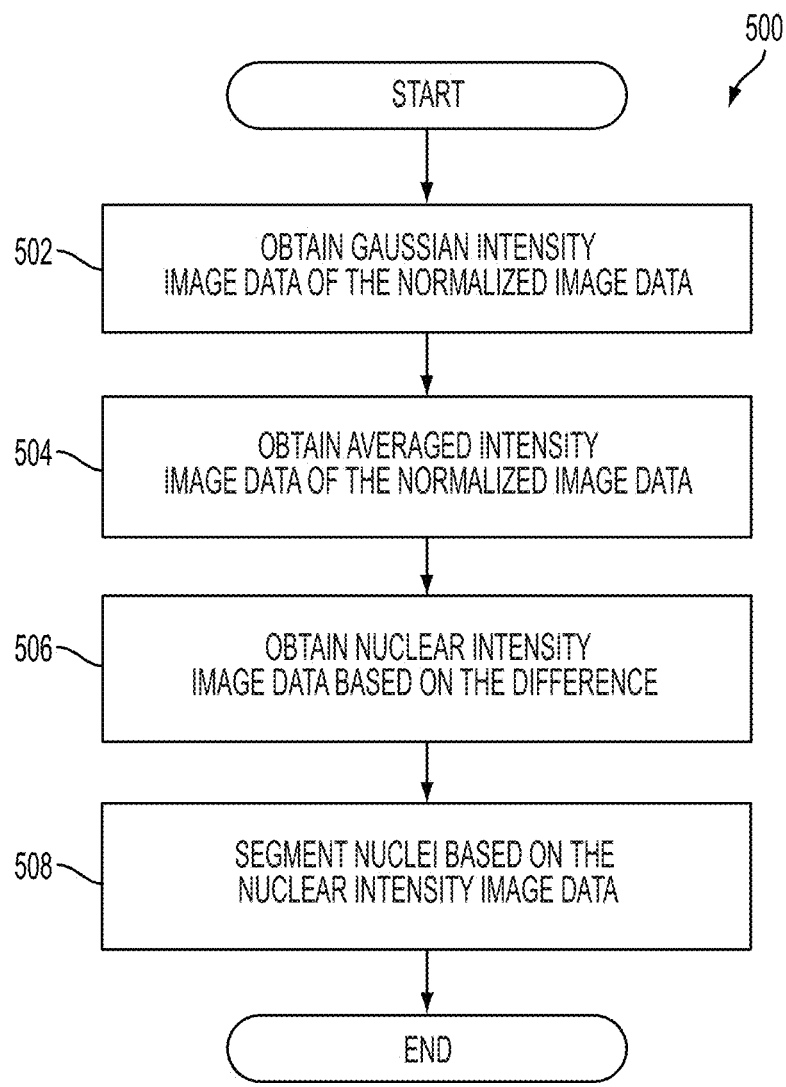
FIG. 5 illustrates an exemplary process flowchart for segmenting nuclei according to an embodiment of the current invention.

FIG. 5 illustrates an exemplary process flowchart for segmenting nuclei according to an embodiment of the current invention. Computing device 104 may obtain Gaussian intensity image data of the normalized image data (block 502). For example, computing device 104 may filter the Gaussian intensity image data with a normalized Gaussian filter. The Gaussian filter may have a similar scale to the size of nuclei in the image data, for example, with pixel sizes of 0.575 μm, the Gaussian filter may be 23 pixels by 23 pixels.

Computing device 104 may obtain averaged intensity image data of the normalized image data (block 504). For example, computing device 104 may calculate the average intensity across individual images by averaging the intensity of all pixels within each individual image. Computing device 104 may obtain nuclear intensity values without regional background by subtracting the averaged intensity image data from the Gaussian intensity image data (block 506). Computing device 104 may then segment nuclei in the image data based on identifying pixels with intensity values greater than a threshold (block 508).

Figure 6:
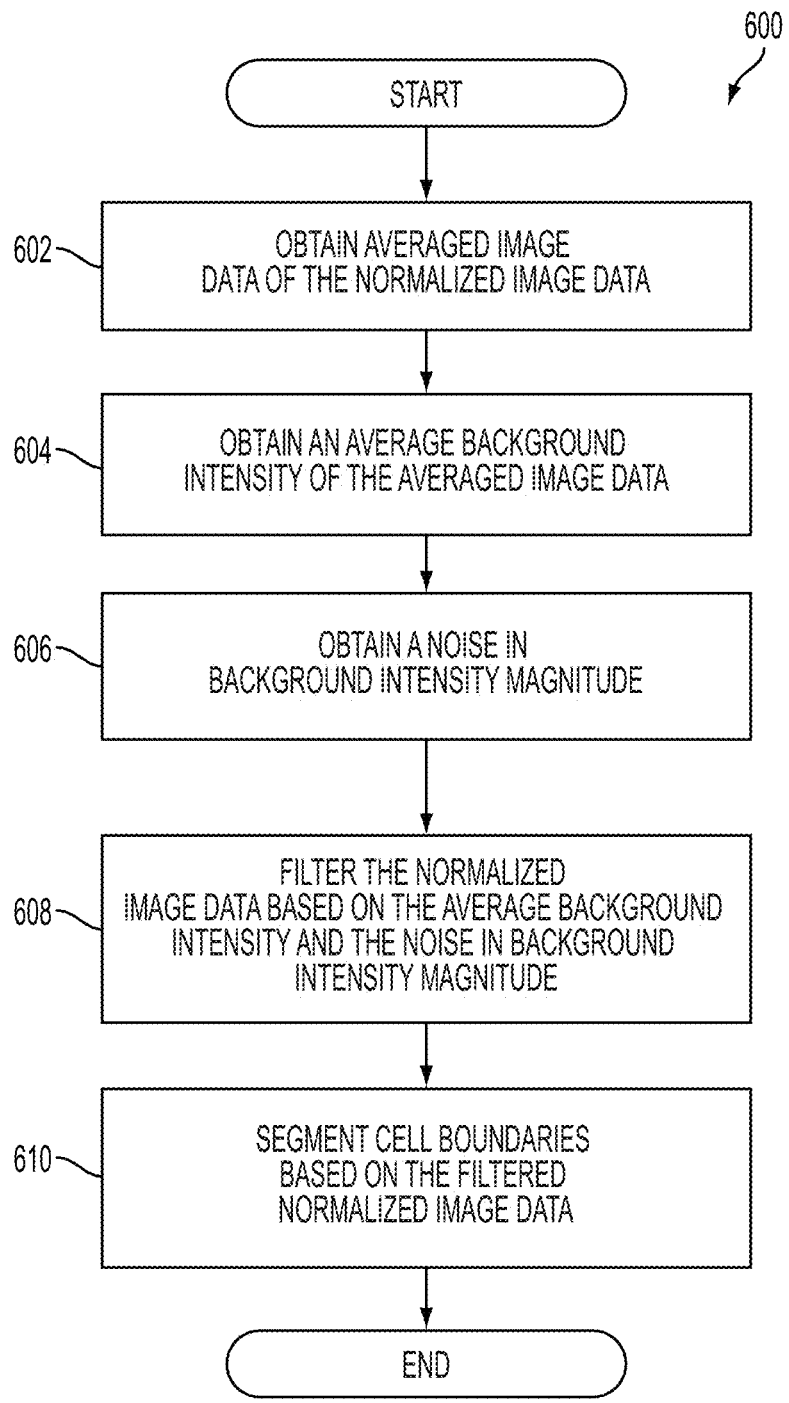
FIG. 6 illustrates an exemplary process flowchart for segmenting cell boundaries according to an embodiment of the current invention.

FIG. 6 illustrates an exemplary process flowchart for segmenting cell boundaries according to an embodiment of the current invention. Cell boundaries may correspond to cell membranes separating the interior of the cells from an outside environment. For example, computing device 104 may use normalized image data corresponding to a UV channel and/or a red filter in which cells are stained with phalloidin. Phalloidon binds to F-actin, which generally results in a stronger signal at cell boundaries allowing segmentation of cell boundaries. In cases where cells are very close together or in direct contact, computing device may use normalized image data corresponding to a homogenous dye, e.g., HCS cell mask, to identify edges between cells based on watershed segmentation.

Computing device 104 may obtain averaged image data of the normalized image (block 602). Computing device 104 may obtain the averaged image data by processing the images with a three pixel by three pixel averaging smoothing filter.

Computing device 104 may then obtain an average background intensity of the averaged image data (block 604) and noise in background intensity magnitude (block 606). An initial average background intensity and initial associated noise in background intensity magnitude may be calculated based on the averaged image data. The initial average background intensity may be initially set to the average of all pixel intensities and the initial associated noise in background intensity magnitude may be the standard deviation in intensity of the pixels. A set of pixel intensities may then be determined by including pixels with intensity values less than the sum of the initial average background intensity and 3.5 times the standard deviation. The average background intensity may then be updated to be equal to the mode of the set of pixel intensities and the associated noise in background intensity magnitude may then be updated to be the standard deviation of intensity within the set of pixel intensities.

Computing device 104 may filter the normalized image data based on selecting all pixels in an image with intensity values greater than the sum of the average background intensity, noise in background intensity magnitude, and a threshold factor (block 608). The threshold factor may range from a value of 2 to 5. Computing device 104 may then segment cell boundaries based on the filtered normalized image data (block 610). For example, the filtered normalized image may filter out all intensity values except those corresponding to cell boundaries whereby the computing device 104 may segment cell boundaries.

Figure 7:
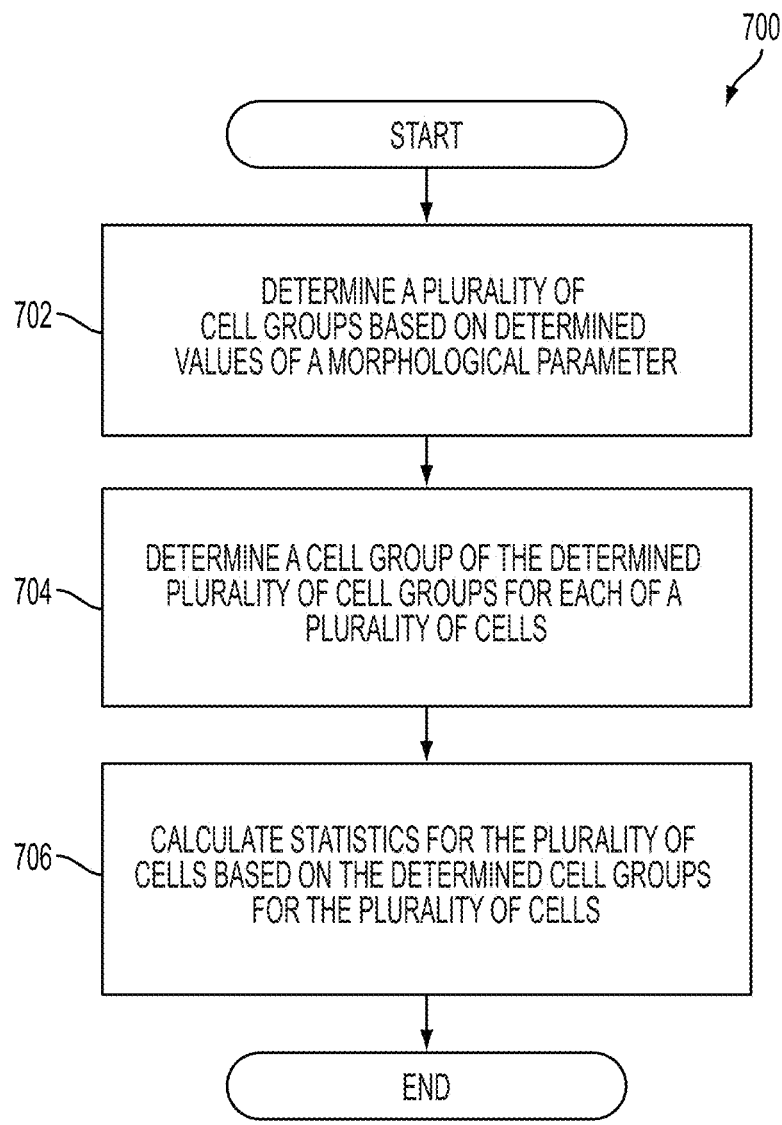
FIG. 7 illustrates an exemplary process flowchart for calculating statistics for a plurality of cells based on cell groups according to an embodiment of the current invention.

FIG. 7 illustrates exemplary process flowchart 700 for calculating statistics for a plurality of cells based on cell groups according to an embodiment of the current invention. Computing device 104 may calculate statistics from values of a morphological parameter as determined above. Computing device 104 may determine a plurality of cell groups based on the determined values of the morphological parameter (block 702). For example, computing device 104 may determine there are 15 different cell groups within the plurality of cells. Each cell group may correspond with cells with a particular range of the value of the morphological parameter. Cell groups may also be determined based on determined values of a plurality of morphological parameters. For example, computing device 104 may determine that there are 15 different cell groups with varying ranges of the plurality of morphological parameters. The ranges for the cell groups may be determined by the computing device 104 based on the determined values of one or more morphological parameters for the plurality of cells.

In determining the plurality of cell groups, the parameters for cells may also be grouped together so that the mean value of the parameters in the groups are used to represent the value of the grouped parameters. Parameters may be grouped based on principle component analysis (PCA).

Computing device 104 may determine a cell group of the determined plurality of cell groups for each of the plurality of cells (block 704). For example, computing device 104 may determine that based on the determined morphological parameters of a given cell, that cell is determined to belong to a particular cell group. Each cell is treated as its own entity and grouped in one group based on its parameter values.

Computing device 104 may calculate statistics for the plurality of cells based on the determined cell groups for the plurality of cells (block 706). For example, computing device 104 may calculate statistics on a cell group basis using the morphological parameters of the cells in the cell groups. Computing device 104 may determine that a cell group corresponds to metastatic dells based on the morphological parameters of the cells in the cell group. Computing device 104 may also calculate statistics on the plurality of cells based on cell group statistics.

System 100 may also be used to determine values of a morphological parameter for corresponding cell cycle phases and fractions of a plurality of cells in the corresponding cell cycle phases according to an embodiment of the current invention.

Figure 8:
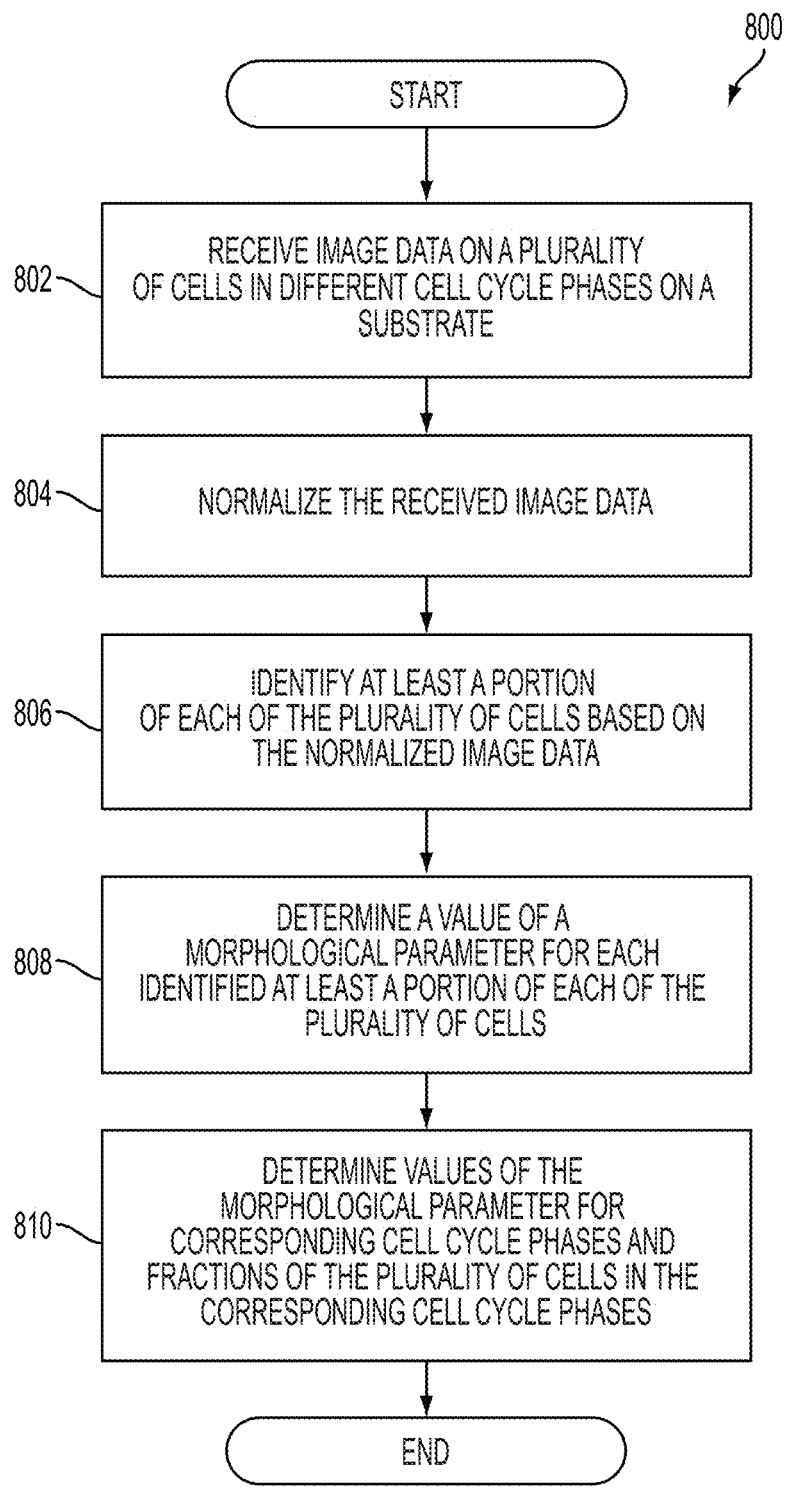
FIG. 8 illustrates an exemplary process flowchart for determining values of a morphological parameter for corresponding cell cycle phases and fractions of a plurality of cells in the corresponding cell cycle phases according to an embodiment of the current invention.

FIG. 8 illustrates exemplary process flowchart 800 for determining values of a morphological parameter for corresponding cell cycle phases and fractions of a plurality of cells in the corresponding cell cycle phases according to an embodiment of the current invention.

The cell cycle is the series of highly regulated steps that lead to controlled cell division. Typically, cells first prepare for DNA synthesis ($G_1$ phase), replicate their DNA (S phase), prepare for mitosis ($G_2$ phase), and undergo mitosis (M phase) [Hartwell, L. & Kastan, M. Cell cycle control and cancer. *Science* 266, 1821-1828 (1994); Folkman, J. & Moscona, A. Role of cell shape in growth control. *Nature* 273, 345-349 (1978)]. During this cell cycle, specific proteins serve as door guards at every phase to prevent cells from early entrance into the next stage of cell cycle [van den Heuvel, S. & Harlow, E. Distinct roles for cyclin-dependent kinases in cell cycle control. *Science* 262, 2050-2054 (1993)]. Misregulation of cell cycle in human and rodent cells has been implicated in a number of disease states [Sherr, C. J. Cancer Cell Cycles. *Science* 274, 1672-1677 (1996); Wang, W. et al. Neural cell cycle dysregulation and central nervous system diseases. *Progress in Neurobiology* 89, 1-17 (2009); Keyomarsi, K. & Pardee, A. B. Redundant cyclin overexpression and gene amplification in breast cancer cells. *Proceedings of the National Academy of Sciences* 90, 1112-1116 (1993)]. For example, mutated p53 causes cells to lose the function of the $G_1$/S checkpoint, replicating defective DNA, and finally leading to cancer [Sherr, C. J. Cancer Cell Cycles. *Science* 274, 1672-1677 (1996); Keyomarsi, K. & Pardee, A. B. Redundant cyclin overexpression and gene amplification in breast cancer cells. *Proceedings of the National Academy of Sciences* 90, 1112-1116 (1993); Kastan, M. B. & Bartek, J. Cell-cycle checkpoints and cancer. *Nature* 432, 316-323 (2004)].

Flow cytometry (FC) is the instrument of predilection to measure cell-cycle distribution and the effects of drug treatment or genetic alteration (knockdown, knockout, over-expression, etc.) on cell cycle [Jayat, C. & Ratinaud, M.-H. Cell cycle analysis by flow cytometry: Principles and applications. *Biology of the Cell* 78, 15-25 (1993); Harper, J. V. in, Vol. 296 157-166 2004)]. A major advantage of FC is its ability to analyze a large number of cells in a short time.

However, conventional FC analysis requires cells to be detached from their substrate and therefore cannot measure cell properties (e.g. nuclear morphology, cell migration, cytoskeleton organization, etc.) at the same time in the same environment. Moreover, since the expression of a wide range of proteins greatly vary during cell cycle, [Klein, E. A. et al. Cell-Cycle Control by Physiological Matrix Elasticity and In Vivo Tissue Stiffening. *Current Biology* 19, 1511-1518 (2009); Benecke, B.-J., Ben-Ze'ev, A. & Penman, S. The control of mRNA production, translation and turnover in suspended and reattached anchorage-dependent fibroblasts. *Cell* 14, 931-939 (1978); Maeshima, K. et al. Cell-cycle-dependent dynamics of nuclear pores: pore-free islands and lamins. *Journal of Cell Science* 119, 4442-4451 (2006)] these cell properties may adopt significantly different values in different phases.

Consequently, without simultaneous measurement of cell cycle phase and cell properties in the same cells, an observed change in cell properties following a forced change in protein expression does not necessarily mean that this protein is a regulator of the cell property of interest. Rather this protein could be a cell cycle regulator [Cooper, S. Rethinking synchronization of mammalian cells for cell cycle analysis. *Cellular and Molecular Life Sciences* 60, 1099-1106 (2003); Pei-Hsun, W., Shen-Hsiu, H., Tina, R., Ie-Ming, S. & Yiider, T. Cell cycle-dependent alteration in NAC1 nuclear body dynamics and morphology. *Physical Biology* 8, 015005 (2011)].

Computing device 104 may determine values of a morphological parameter for corresponding cell cycle phases and fractions of a plurality of cells in the corresponding cell cycle phases from image data on the plurality of cells on a substrate. Computing device 104 may receive image data on the plurality of cells in difference cell cycle phases on the substrate (block 802). Computing device 104 may receive image data from microscope 102.

Computing device 104 may normalize the received image data (block 804). Computing device 802 may normalize the image data based on the process shown in FIG. 4. Computing device 802 may identify at least a portion of each of the plurality of cells based on the normalized image data (block 806). Computing device 104 may identify at least a portion of each of the plurality of cells based on the processes shown in FIGS. 3, 5, and/or 6. Computing device 802 may determine a value of a morphological parameter for each identified at least a portion of each of the plurality of cells (block 808). Computing device 104 may determine the value of the morphological parameter based on the process shown in FIG. 2.

Computing device 104 may determine values of the morphological parameter for corresponding cell cycle phases and fractions of the plurality of cells in the corresponding cell cycle phases (block 810). Phases may include, for example, a G0 phase which may be a resting phase where the cell is not dividing, $G_1$ phase, S phase, $G_2$ phase, and M phase. The values of the morphological parameter for corresponding cell cycle phases may be the mean value of a given cell property for the cell cycle phase. Fractions of the plurality of cells may correspond to the percentage of the plurality of cells which are determined to correspond with a particular cell cycle phase or the relative time cells spend in the phase during the cell cycle.

Computing device 104 may determine values of the morphological parameter for corresponding cell cycle phases and fractions of the plurality of cells in the corresponding cell cycle phases based on solving for a linear combination of the fractions and the values of the morphological parameter for corresponding cell cycle phases.

Computing device 104 may also identify at least a portion of the plurality of cells based on obtaining a total intensity of the plurality of cells in a sample, obtaining an estimate of average intensity across a cell cycle of the plurality of cells, obtaining a number of cells in the plurality of cells based on the total intensity and the estimate of average intensity, and identifying the cells based on the number of cells. For example, computing device 104 may calculate the number of cells to be equal to summation of the pixel intensities in an image of the sample divided by the average intensity of a cell across a cell cycle.

Diagnostic Example

Genetic analysis has not revealed so far predictive correlations between specific mutations and metastatic disease, the primary cause of pancreatic cancer-related death. Herein is described a high-throughput, high-content, microscopy-based phenotypic assay that quantitatively and highly reproducibly characterizes >11,000 nucleus- and cell-associated properties and corresponding statistical parameters in >5,000 individual cells in a matter of minutes. Analysis of a training dataset of early and late-stage pancreatic cancer patients indicates that an ensemble of 38 non-conventional cell properties correlates extremely strongly with metastatic disease. Validation of this multi-parameter correlation with additional pancreatic cancer patients, cancer cells from other organs, cells from other species, and drug-resistant cells highlighted the predictive power of this phenotypic signature in pancreatic cancer metastasis. These results suggest that cells of a primary tumor with divergent mutations and genetic backgrounds adopt highly convergent physical properties in order to successfully metastasize to a distal site.

Recent estimates suggest that millions of cells are shed from a primary tumor sites every day; yet, progression to metastatic disease often take years which suggests that metastasis is a highly inefficient process. In order to successfully overcome the difficult multiple-step metastatic process—invade and migrate through the dense, tortuous stromal matrix, intravasation, survive shear forces of blood flow, successfully re-attach to blood vessel walls, colonize a distal site, and be reactivated following dormancy—metastatic cells may share precise physical properties. This could be in variant with the observation described below that isogenic cells growing in the same microenvironment often display an extremely wide range of properties, including huge variations in cell size, cell shape, nuclear size, and nuclear shape, presumably due to differences in protein expression and epigenetic profiles among cells. Support for this stems from the observation that highly metastatic cells often show mechanically softer cytoplasm than transformed non-metastatic cells. This approach is that pancreatic cancer cells with different genetic backgrounds (i.e. harvested from different patients) and different genetic mutations (i.e. as shown in REF) may need to fulfill specific phenotypic conditions in order to successfully metastasize to the liver, a common metastatic target organ from tumors in the tail and body of the pancreas, for which surgery is usually not an option.

Since it is unknown which cellular or nuclear properties, if any, would correlate with metastatic disease in pancreatic cancer, a high-throughput, high-content, microscopy-based phenotypic assay is developed that can quantitatively and highly reproducibly characterize a large number (here, >11,000) nucleus- and cell-associated properties and corresponding statistical parameters in a large number of individual cells (here >5,000) rapidly (here, in a matter of minutes). First, this assay is described, which was applied on previously characterized, genetically sequenced pancreatic cancer cells to generate a training dataset and identify cell and nuclear properties that highly correlated with the pathologically assessed stage of cancer patients. These high phenotypic correlates were then validated and tested by applying the assay in a blind test to unknown samples, including other pancreatic cancer cells, cells from different species (mouse), and normal cells of different types (myoblasts and fibroblasts).

Methods
Cell Culture

Purposely, the pancreatic cells used to establish the training dataset for htCP were chosen to be the same as those recently sequenced to establish common pathways for pancreatic cancer [science 2008 and nature 2010] (Table 1).

| Sample | Cell Line | Patient Age (yr) | sex | Carcinoma type | Tissue derivation | Stage |
|---|---|---|---|---|---|---|
| PAC001 | A2.1 | 62 | M | Ductal adeno-carcinoma | Liver metastasis | IV |
| PAC002 | A38.5 | 51 | M | Ductal adeno-carcinoma | Liver metastasis | IV |

-continued

| Sample | Cell Line | Patient Age (yr) | sex | Carcinoma type | Tissue derivation | Stage |
|---|---|---|---|---|---|---|
| PAC003 | A6L | 57 | M | Ductal adeno-carcinoma | Liver metastasis | IV |
| PAC004 | E3 (A10.7) | 60 | M | Ductal adeno-carcinoma | Liver metastasis | IV |
| PAC005 | PANC215 | 60 | F | Ductal adeno-carcinoma | primary pancreatic tumor | IIB |
| PAC006 | Panc10.05 | 81 | M | Ductal adeno-carcinoma | primary pancreatic tumor | IIB |
| PAC007 | Panc198 | 69 | M | Ductal adeno-carcinoma | primary pancreatic tumor | IIB |
| PAC008 | panc2.5 | 54 | F | Ductal adeno-carcinoma | primary pancreatic tumor | IIB |
| PAC009 | panc5.04 | 77 | F | Ductal adeno-carcinoma | primary pancreatic tumor | IIB |
| PAC010 | HPDE | NA | NA | | Ductal epithelium | cell |
| PAC011 | HPNE | NA | NA | | Normal epithelium | cell |

Special care was also taken to characterize cells of same passage number as in these earlier papers. Cells were cultured at 37° C. and 5% $CO_2$, approximately 1.5 weeks prior to imaging. Every day, 7 images (Five at 10× magnification and 2 at 20× magnification) of every cell line were recorded to estimate the proliferation rate every day. Cells were passaged every three to four days, based on these proliferation rates. Cells for the validation dataset were blindly provided to use by the Maitra lab and were cultured according to the same protocol used for the training data set with their appropriate media.

Immunostaining and Microscopy

Approximately 12,000 cells were plated in each of the well of a 24-well glass bottom plate (MatTek, MA), corresponding to approximately 20% surface coverage; to ensure single cell resolution. After 16 h incubation, cells were fixed with 3.7% para-formaldehyde for 12 min at room temperature (RT). Cells were then permeabilized with 0.1% Triton X-100 (Sigma, St. Louis, Mo.) for 10 min; nonspecific binding was blocked with phosphate-buffered saline (PBS) supplemented with 1% albumin from bovine serum (BSA) for 40 min. Cells were then incubated for 60 min. with a primary antibody, and then for an additional 60 min. with three dyes and one secondary antibody, which had been pre-diluted in PBS supplemented with 1% of BSA at specified concentration. To stain microtubule (MT), cells were incubated with a monoclonal mouse anti-alpha tubulin (Abcam, Cambridge, Mass.) at 1:500 dilution, and subsequently incubated with Alexa Fluor 568 goat anti-mouse antibody (Invitrogen, Carlsbad, Calif.) at 1:200 dilution. Nuclear DNA was stained with Hoechst 33342 (Sigma, St. Louis, Mo.) at 1:50 dilution. Cytoplasm was stained with the non-specific dye HCS CellMask Cy-5 (Invitrogen, Carlsbad, Calif.) at 1:20000 dilution. Actin was stained with phalloidin 488 (Invitrogen, Carlsbad, Calif.) at a 1:40 dilution. PBS rinse was conducted three times between each staining step.

Eighty-one (9-by-9 square grid) fields of view of each well were visualized with a Nikon [model] camera mounted on a Nikon TE300 epifluorescence microscope (Nikon Melville, N.Y.), and equipped with a motorized stage and motorized excitation and emission filters (all Prior Scientific, Rockland, Mass.) controlled by NIS-Elements (Nikon). Four fluorescence channels (UV, RFP, GFP, and Cy5) and one phase-contrast channel were recorded to obtain the necessary morphometric information about the nucleus, actin filament network, MT, and cellular body of every single cell within the scanning region. Quantification of nuclear and cellular phenotypic parameters was conducted using a low-magnification lens (10× Plan Fluor lens; N.A. 0.3, Nikon) with a custom high throughput phenotyping Matlab code developed in our laboratory. Quantitative estimation of the cellular and nuclear phenotypes was validated using both manual tracing of cells and nuclei and using high-magnification imaging (40× Plan Fluor lens; N.A. 1.3, Nikon), as explained in the main text.

Image Scanning Grid Setup

For each well of the culture dish, 405 images (81 fields of view×5 channels) were acquired with a 10× objective, covering a contiguous area of 5.6 mm×5 mm (26 mm$^2$) The size of the camera sensor was 1280×1024 pixels; under 10× magnification, the pixel size was 0.575 µm. A 10% (~50 µm) overlay was set between adjacent fields of view to reduce artificially fragmented cells and to stitch images (based on stage position instead of image mapping). Frame dimensions were (1280× 0.9×0.575=) 662 µm in the x-direction, and (1024×0.9×0.575=) 520 µm in the y-direction. Therefore for a 9 by 9 scanned region, the total imaging field on the sample dish was 662*(9+1/9) µm*520*(9+1/9) µm~28.5 mm$^2$ region.

Image Calibration

Unavoidable non-uniform illumination of the samples presents challenges when doing intensity-based cell segmentation of fluorescent images. Briefly, for each well, reference illumination and dark images were taken and used to normalize the intensities in the illumination field.

Figure 9:
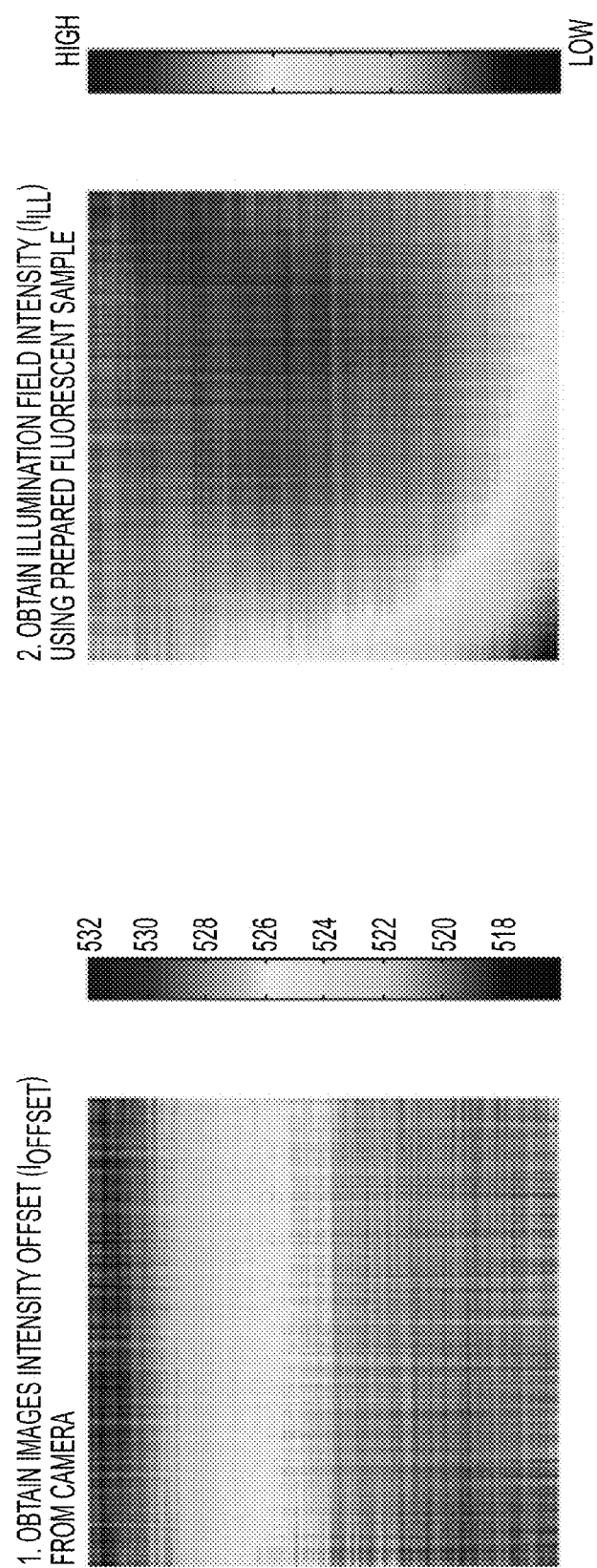
FIG. 9 illustrates exemplary intensity offset and illumination field intensity images according to an embodiment of the current invention.

FIG. 9 illustrates exemplary intensity offset and illumination field intensity images according to an embodiment of the current invention. The images intensity offset image is shown on the left and the illumination field intensity image is shown on the right. The intensity offset image may correspond with dark image data and the illumination field intensity image may correspond to reference illuminated image data.

Figure 10:
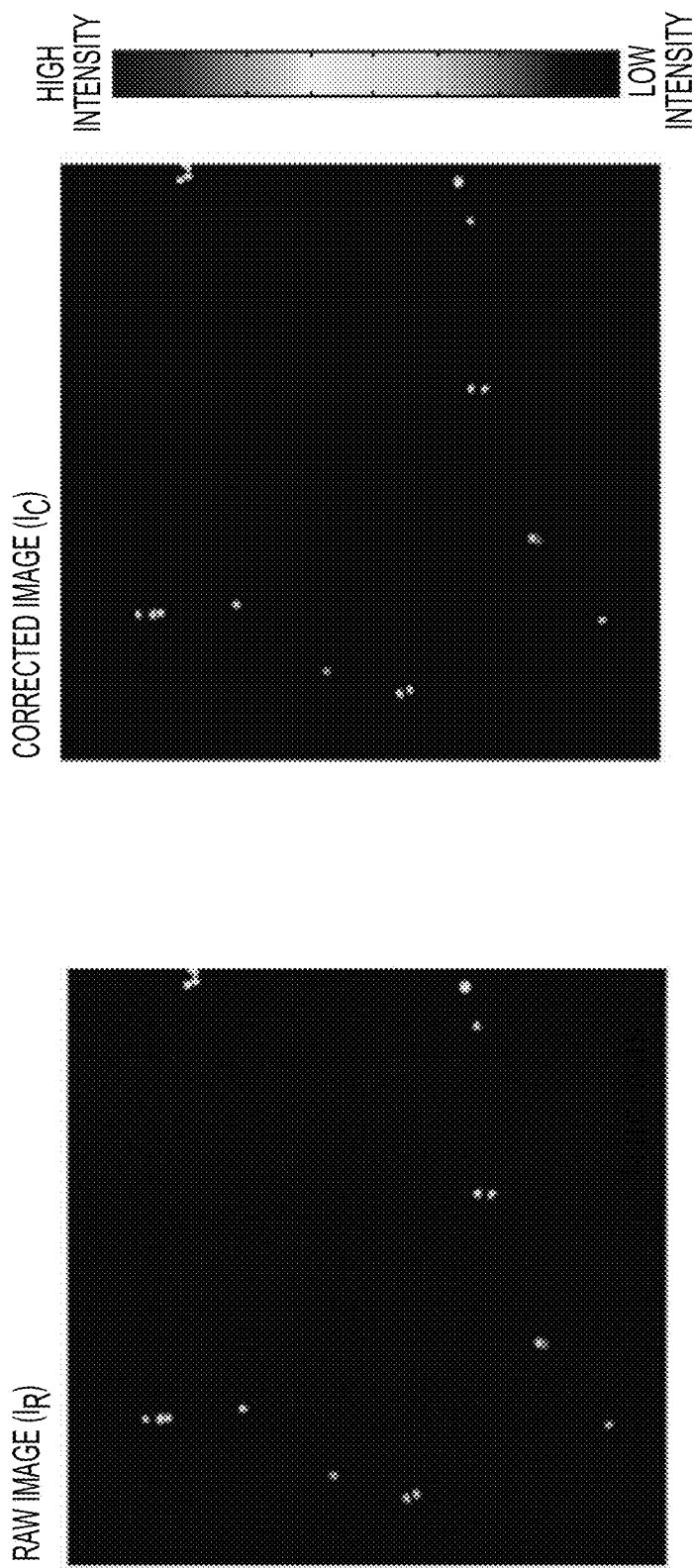
FIG. 10 illustrates exemplary images of a raw image before normalization and a corrected image after normalization according to an embodiment of the current invention.

FIG. 10 illustrates exemplary images of a raw image before normalization and a corrected image after normalization according to an embodiment of the current invention. The raw image ($I_r$) is shown on the left and the corrected image ($I_c$) is shown on the right.

Figure 11:
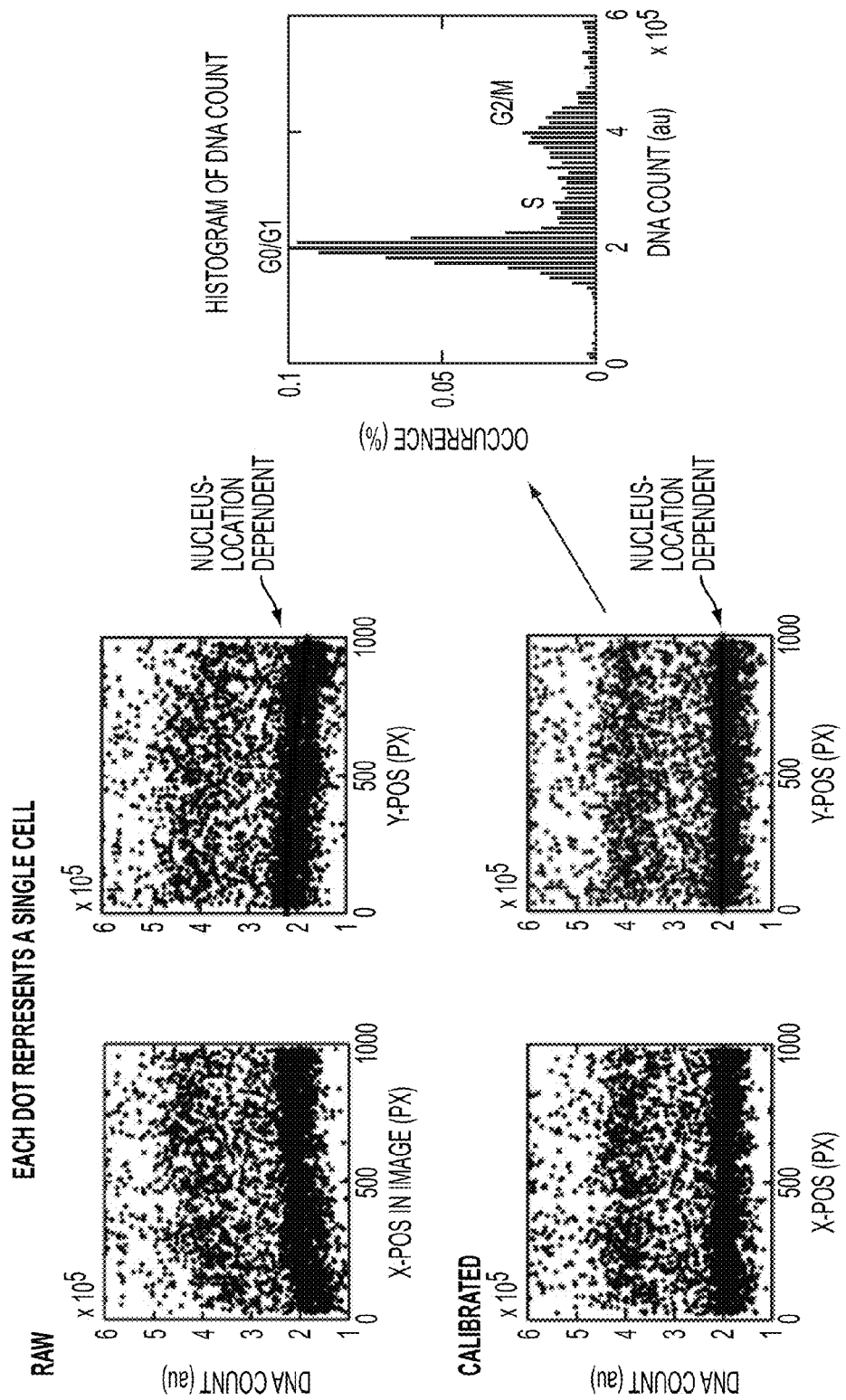
FIG. 11 illustrates histograms showing how normalization, or intensity-field correction, ensures more accurate intensity counts.

FIG. 11 illustrates histograms showing how normalization, or intensity-field correction, ensures more accurate intensity counts. Verification of the histograms is given by a typical DNA count histogram as generally shown in flow cytometry results.

Segmentation of Cellular and Nuclear Boundaries

To segment individual cells and nuclei, slightly different approaches are used based on the same principle. For nuclear segmentation, because of the relatively circular shape and relatively even intensity of the Hoechst stain, calibrated images (as described in the previous section) are filtered with a 23×23 px normalized Gaussian filter (similar scale as the size of nuclei) and an averaging filter (same size) to obtain $I_G$ (Gaussian intensity) and $I_M$ (averaged intensity). Subtracting $I_M$ from $I_G$ gives $I_N$, the nuclear intensity values without regional background. Empirical testing showed that a threshold setting of 10 was optimal.

Because cells are larger than nuclei, larger size filters are used. One major limitation with spatial domain image filters is non-continuous edges. Increasing the size of the filter increases the size of this "non-trustable" region. The use of a spatial filter 2r+1 in size will lead to the loss of r+1 pixels from the edge because of incomplete information, which greatly reduces the usable image size. For the nucleus, there are only ~12 pixels lost, which is acceptable. For an object the size of the cell, the much larger number of lost pixels may be unacceptable. Thus, spatial filters were not used to segment individual cells. Rather, images of cells were processed with a 3×3 averaging smoothing filter.

Because the background intensity was not eliminated during processing (as it is for the nucleus), background intensity is estimated to properly threshold cell boundaries. First, the average, $<I_{BG}>$, and associated standard deviation, $I_{RBG}$, of the background intensity of the smoothed imaged are calculated to obtain a set of pixel intensities less than $<I_{BG}>+ 3.5*I_{RBG}=I_{nn}$. Then, the value of $<I_{BG}>$ is updated using the mode of $I_{nn}$, $I_{RBG}$, and the standard deviation of $I_{nn}$. Three to five iterations will generally result in stable values of $I_{BG}$ and $I_{RBG}$, which represent the average background intensity value and associated noise in background intensity magnitude, respectively. Next, $I_{BG}$ and $I_{RBG}$ are used to select the signal region of fluorescently labeled cells. The threshold factor, thc, is defined and all the pixels in the image with an intensity value larger than $I_{BG}+$thc$+I_{RBG}$ are selected. The assumption is made that the background noise intensity can be described by a Gaussian distribution and set thc>2, representing the >95% of the background that will not be thresholded out. Depending on the signal intensity level, the value of thc will range between 2 and 5.

Using the above approach, the cell boundary is determined using phalloidin-stained F-actin images. F-actin usually gives a stronger signal at the cell boundary than at the cell center, differentiating the boundary from the cytoplasm with less bias than a more homogenous dye (such as HCS cell mask) would allow for. In fact, HCS cell mask intensities concentrated around the nucleus—the ticker region of the cell—and decayed towards the edge of the cell; because of the low NA objective, the edge intensity values was blurred, making edge detection very sensitive to bias and sample-to-sample variation.

However, when cells were very close to one another or in direct contact, then edge intensity values given by phalloidin staining were all above background and may not allow for direct segmentation. In these cases, HCS cell mask is used to perform so-called watershed segmentation and identify edges between two cells. The collected set of nucleus and cell objects is used to calculate their morphological parameters, as described in the next section.

Cell Morphology Description and Representation

There used five general categories of nuclear and cellular shape parameters: basic shape and size, "roughness", "curvature", N/C ratios, and nuclear positioning in the cell. Basic cellular and nuclear morphology parameters included apparent surface area, perimeter, shape factor, aspect ratio, etc. Characterization of cellular and nuclear roughness was performed by transforming the 2D boundary, $(\underline{X}_{bc}(k),\underline{Y}_{bc}(k))$, of each cell and nucleus into a corresponding 1D curve, R, which was computed from the distance between the center of the object (nucleus or cell) to its curvilinear boundary using the following equation: $R(k)=((\underline{X}(k)-<\underline{X}_{bc}>)^2+(\underline{Y}(k)-<\underline{Y}_{bc}>)^2)^{0.5}$. The shape of the curve R(k) was characterized by 38 different parameters, including mean value, maximum value, minimum value, mode, etc.

Characterization of the cellular and nuclear curvature of each cell and nucleus was performed by first obtaining smoothed sets of boundary coordinates, $(\underline{X}_{bcs}(k),\underline{Y}_{bcs}(k))$. These were obtained by convolving the raw coordinates, $(\underline{X}_{bc}(k),\underline{Y}_{bc}(k))$ in the x- and y-directions with a discrete 1D Gaussian distribution that was 11 pixels in size and of unity standard deviation. A set of curvature, (κ), was then estimated using the following equation:

$$\kappa = \frac{|x'y'' - y'x''|}{(x'^2 + y'^2)^{3/2}},$$

Figure 12:
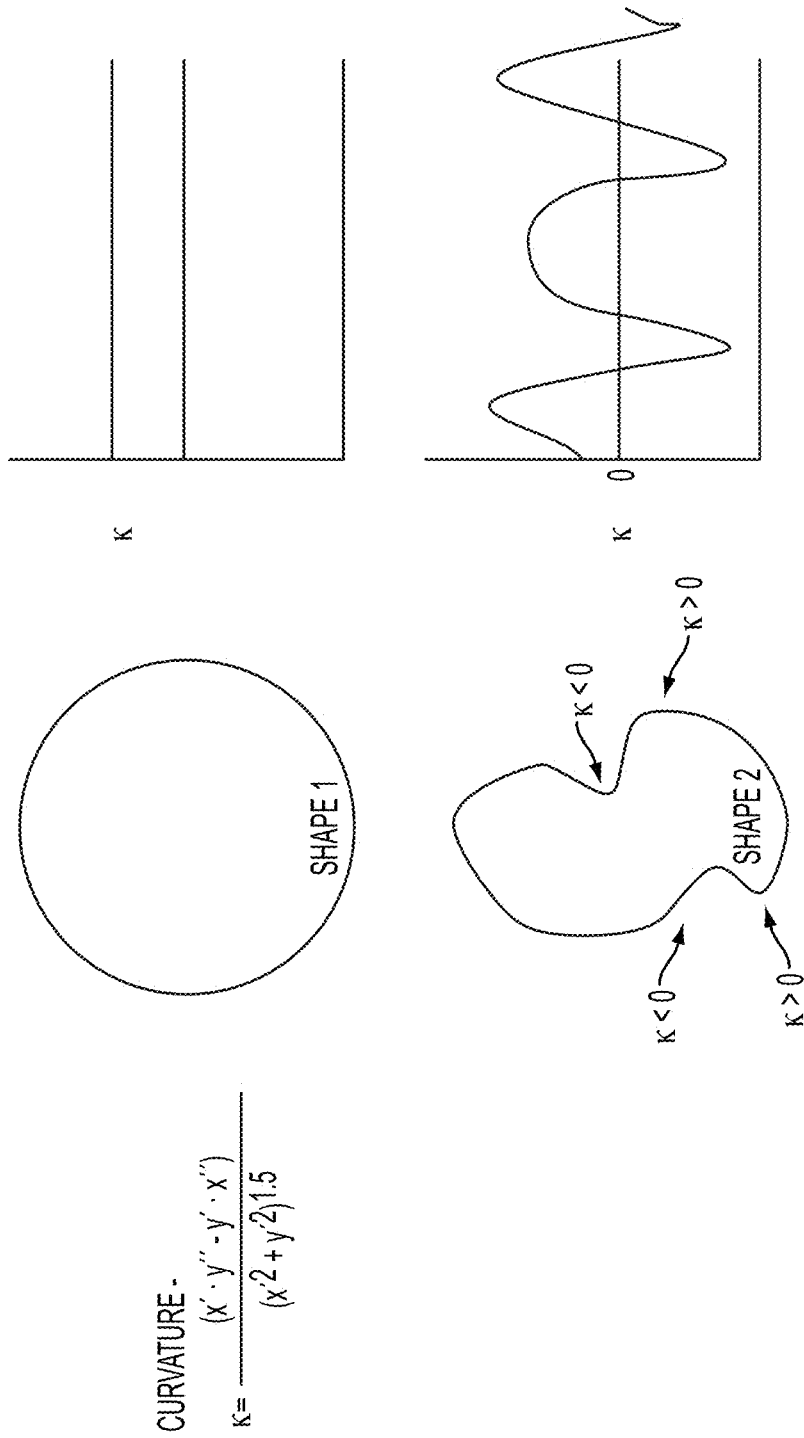
FIG. 12 illustrates two exemplary shapes transformed into a corresponding curvature curves according to an embodiment of the current invention.

FIG. 12 illustrates two exemplary shapes transformed into a corresponding curvature curves according to an embodiment of the current invention. The shape of the curvature was obtained in the same transformation as for the shape roughness.

Figure 13:
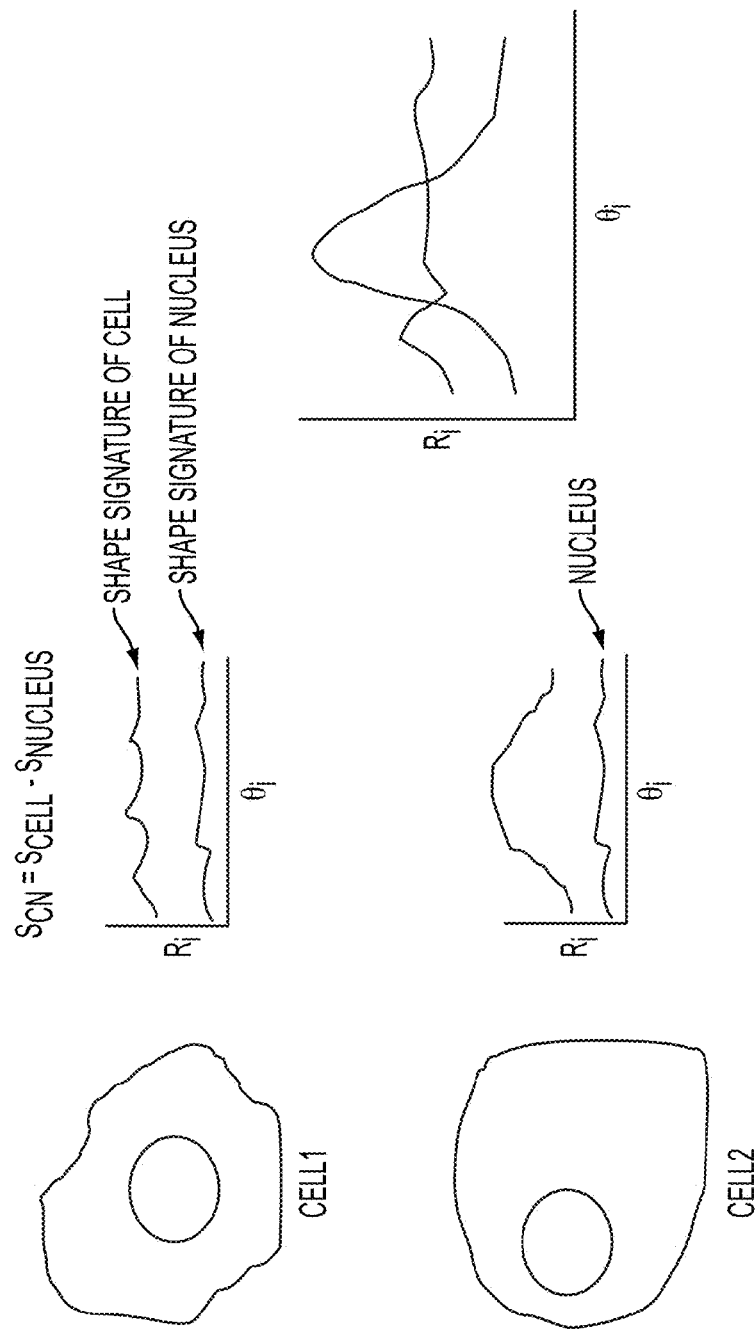
FIG. 13 illustrates a shape signature of cell-nucleus relative positioning according to an embodiment of the current invention.

FIG. 13 illustrates a shape signature of cell-nucleus relative positioning according to an embodiment of the current invention. The shape signature of cell-nucleus relative positioning may be determined based on the difference between the shape signature of the cell and shape signature of the nucleus.

Nucleus:cytoplasm ratios (of size, shape, etc), which are widely used for the pathological assessment of cancerous tissues, were also calculated.

Finally, the relative nuclear and cell locations are characterized using a polar coordinate system with an origin at the center of the nucleus. A set of distances, $R_N(\theta)$, were computed from the center of the nucleus to the edge of the nucleus, and $R_C(\theta)$, from the center of the nucleus to the edge of the cell as a function of the angle θ.

Figure 14:
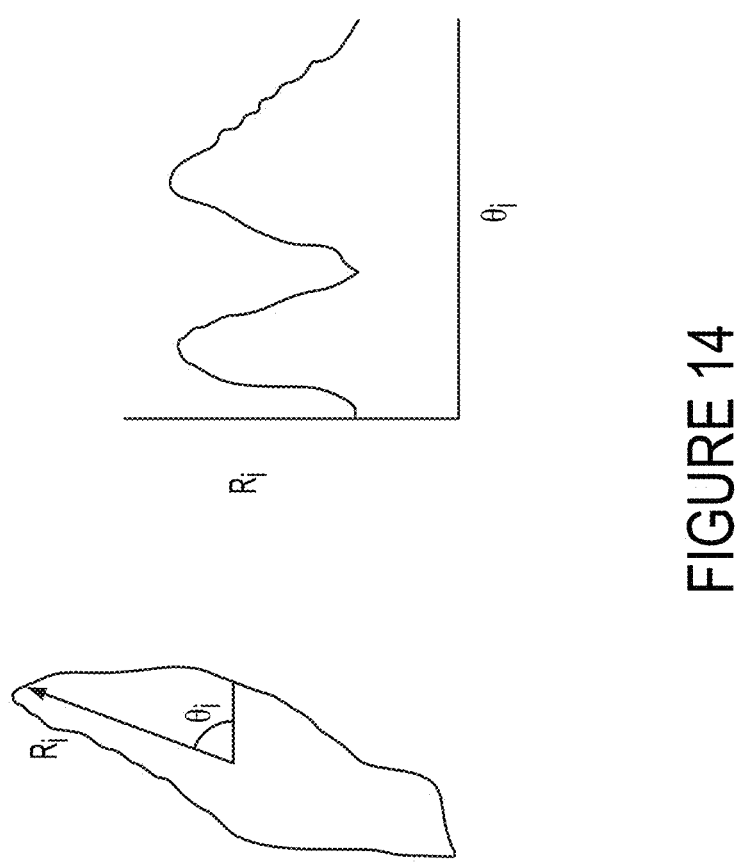
FIG. 14 illustrates an exemplary 2D boundary transformed into a corresponding curve according to an embodiment of the current invention.

FIG. 14 illustrates an exemplary 2D boundary transformed into a corresponding curve according to an embodiment of the current invention. The angle θ, and distance $R_i$ shown in the 2D boundary one the left are transformed into the curve on the right based on the above equation. Relative shape distribution between cell and nucleus were obtained by $R_{NC}(\theta)=R_C(\theta)-R_N(\theta)$. Then, as described above, 38 parameters were estimated to describe this shape.

In all, 297 primary nuclear and cellular parameters were estimated to quantitatively characterize the morphology of a single cell. These parameters are listed in the below table.

| parameter ID | subcellular object | shape estimator category | estimator description |
|---|---|---|---|
| 1 | nucleus | basic | area |
| 2 | nucleus | basic | perimeter |
| 3 | nucleus | basic | long axis length |
| 4 | nucleus | basic | short axis length |
| 5 | nucleus | basic | orientation |
| 6 | nucleus | basic | solidity |
| 7 | nucleus | basic | equivalent diameter |
| 8 | nucleus | basic | aspect ratio |
| 9 | nucleus | basic | circularity |
| 10 | nucleus | basic | roundness |
| 11 | nucleus | boundary signature | mean |
| 12 | nucleus | boundary signature | median |
| 13 | nucleus | boundary signature | mode |
| 14 | nucleus | boundary signature | max |
| 15 | nucleus | boundary signature | min |
| 16 | nucleus | boundary signature | 25% percentile value |
| 17 | nucleus | boundary signature | 75% percentile value |
| 18 | nucleus | boundary signature | mean value above 75% percentile |
| 19 | nucleus | boundary signature | mean value below 25% percentile |
| 20 | nucleus | boundary signature | summation |
| 21 | nucleus | boundary signature | harmonic mean |
| 22 | nucleus | boundary signature | mean after eliminate 3% outlier |
| 23 | nucleus | boundary signature | mean after eliminate 5% outlier |
| 24 | nucleus | boundary signature | mean after eliminate 15% outlier |
| 25 | nucleus | boundary signature | mean after eliminate 25% outlier |
| 26 | nucleus | boundary signature | standard deviation |
| 27 | nucleus | boundary signature | CV - use mean |
| 28 | nucleus | boundary signature | CV - use median |
| 29 | nucleus | boundary signature | CV - use mode |
| 30 | nucleus | boundary signature | skewness |
| 31 | nucleus | boundary signature | kurtosis |
| 32 | nucleus | boundary signature | $<|x-<x>|>$ |
| 33 | nucleus | boundary signature | range (Xmax-Xmin) |
| 34 | nucleus | boundary signature | difference between X75% and X25% |
| 35 | nucleus | boundary signature | sum(X^2) |
| 36 | nucleus | boundary signature | sum(X^3) |
| 37 | nucleus | boundary signature | mean(X.^2) |
| 38 | nucleus | boundary signature | mean(X.^3) |
| 39 | nucleus | boundary signature | mean(X.^4) |
| 40 | nucleus | boundary signature | mean(X.^5) |
| 41 | nucleus | boundary signature | sum((X-<X>)^2) |
| 42 | nucleus | boundary signature | sum((X-<X>)^3) |
| 43 | nucleus | boundary signature | mean((X-<X>)^2) |
| 44 | nucleus | boundary signature | mean((X-<X>)^3) |
| 45 | nucleus | boundary signature | mean((X-<X>)^4) |
| 46 | nucleus | boundary signature | mean((X-<X>)^5) |
| 47 | nucleus | boundary signature | peak number |
| 48 | nucleus | boundary signature | gini coefficient |
| 49 | nucleus | boundary curvature | mean |
| 50 | nucleus | boundary curvature | median |
| 51 | nucleus | boundary curvature | mode |
| 52 | nucleus | boundary curvature | max |

-continued

| parameter ID | subcellular object | shape estimator category | estimator description |
|---|---|---|---|
| 53 | nucleus | boundary curvature | min |
| 54 | nucleus | boundary curvature | 25% percentile value |
| 55 | nucleus | boundary curvature | 75% percentile value |
| 56 | nucleus | boundary curvature | mean value above 75% percentile |
| 57 | nucleus | boundary curvature | mean value below 25% percentile |
| 58 | nucleus | boundary curvature | summation |
| 59 | nucleus | boundary curvature | harmonic mean |
| 60 | nucleus | boundary curvature | mean after eliminate 3% outlier |
| 61 | nucleus | boundary curvature | mean after eliminate 5% outlier |
| 62 | nucleus | boundary curvature | mean after eliminate 15% outlier |
| 63 | nucleus | boundary curvature | mean after eliminate 25% outlier |
| 64 | nucleus | boundary curvature | standard deviation |
| 65 | nucleus | boundary curvature | CV - use mean |
| 66 | nucleus | boundary curvature | CV - use median |
| 67 | nucleus | boundary curvature | CV - use mode |
| 68 | nucleus | boundary curvature | skewness |
| 69 | nucleus | boundary curvature | kurtosis |
| 70 | nucleus | boundary curvature | <|x-<x>|> |
| 71 | nucleus | boundary curvature | range (Xmax-Xmin) |
| 72 | nucleus | boundary curvature | difference between X75% and X25% |
| 73 | nucleus | boundary curvature | sum(X^2) |
| 74 | nucleus | boundary curvature | sum(X^3) |
| 75 | nucleus | boundary curvature | mean(X.^2) |
| 76 | nucleus | boundary curvature | mean(X.^3) |
| 77 | nucleus | boundary curvature | mean(X.^4) |
| 78 | nucleus | boundary curvature | mean(X.^5) |
| 79 | nucleus | boundary curvature | sum((X-<X>)^2) |
| 80 | nucleus | boundary curvature | sum((X-<X>)^3) |
| 81 | nucleus | boundary curvature | mean((X-<X>)^2) |
| 82 | nucleus | boundary curvature | mean((X-<X>)^3) |
| 83 | nucleus | boundary curvature | mean((X-<X>)^4) |
| 84 | nucleus | boundary curvature | mean((X-<X>)^5) |
| 85 | nucleus | boundary curvature | peak number |
| 86 | nucleus | boundary curvature | gini coefficient |
| 87 | cell | basic | area |
| 88 | cell | basic | perimeter |
| 89 | cell | basic | long axis length |
| 90 | cell | basic | short axis length |
| 91 | cell | basic | orientation |
| 92 | cell | basic | solditiy |
| 93 | cell | basic | equvilant diameter |
| 94 | cell | basic | aspect ratio |
| 95 | cell | basic | circularity |
| 96 | cell | basic | roundness |
| 97 | cell | boundary signature | mean |
| 98 | cell | boundary signature | median |
| 99 | cell | boundary signature | mode |
| 100 | cell | boundary signature | max |
| 101 | cell | boundary signature | min |
| 102 | cell | boundary signature | 25% percentile value |
| 103 | cell | boundary signature | 75% percentile value |
| 104 | cell | boundary signature | mean value above 75% percentile |
| 105 | cell | boundary signature | mean value below 25% percentile |
| 106 | cell | boundary signature | summation |
| 107 | cell | boundary signature | harmonic mean |
| 108 | cell | boundary signature | mean after eliminate 3% outlier |
| 109 | cell | boundary signature | mean after eliminate 5% outlier |
| 110 | cell | boundary signature | mean after eliminate 15% outlier |
| 111 | cell | boundary signature | mean after eliminate 25% outlier |
| 112 | cell | boundary signature | standard deviation |
| 113 | cell | boundary signature | CV - use mean |
| 114 | cell | boundary signature | CV - use median |
| 115 | cell | boundary signature | CV - use mode |
| 116 | cell | boundary signature | skewness |
| 117 | cell | boundary signature | kurtosis |
| 118 | cell | boundary signature | <|x-<x>|> |
| 119 | cell | boundary signature | range (Xmax-Xmin) |
| 120 | cell | boundary signature | difference between X75% and X25% |
| 121 | cell | boundary signature | sum(X^2) |
| 122 | cell | boundary signature | sum(X^3) |
| 123 | cell | boundary signature | mean(X.^2) |
| 124 | cell | boundary signature | mean(X.^3) |
| 125 | cell | boundary signature | mean(X.^4) |
| 126 | cell | boundary signature | mean(X.^5) |

| parameter ID | subcellular object | shape estimator category | estimator description |
|---|---|---|---|
| 127 | cell | boundary signature | sum((X-<X>)^2) |
| 128 | cell | boundary signature | sum((X-<X>)^3) |
| 129 | cell | boundary signature | mean((X-<X>)^2) |
| 130 | cell | boundary signature | mean((X-<X>)^3) |
| 131 | cell | boundary signature | mean((X-<X>)^4) |
| 132 | cell | boundary signature | mean((X-<X>)^5) |
| 133 | cell | boundary signature | peak number |
| 134 | cell | boundary signature | gini coefficient |
| 135 | cell | boundary curvature | mean |
| 136 | cell | boundary curvature | median |
| 137 | cell | boundary curvature | mode |
| 138 | cell | boundary curvature | max |
| 139 | cell | boundary curvature | min |
| 140 | cell | boundary curvature | 25% percentile value |
| 141 | cell | boundary curvature | 75% percentile value |
| 142 | cell | boundary curvature | mean value above 75% percentile |
| 143 | cell | boundary curvature | mean value below 25% percentile |
| 144 | cell | boundary curvature | summation |
| 145 | cell | boundary curvature | harmonic mean |
| 146 | cell | boundary curvature | mean after eliminate 3% outlier |
| 147 | cell | boundary curvature | mean after eliminate 5% outlier |
| 148 | cell | boundary curvature | mean after eliminate 15% outlier |
| 149 | cell | boundary curvature | mean after eliminate 25% outlier |
| 150 | cell | boundary curvature | standard deviation |
| 151 | cell | boundary curvature | CV - use mean |
| 152 | cell | boundary curvature | CV - use median |
| 153 | cell | boundary curvature | CV - use mode |
| 154 | cell | boundary curvature | skewness |
| 155 | cell | boundary curvature | kurtosis |
| 156 | cell | boundary curvature | <|x-<x>|> |
| 157 | cell | boundary curvature | range (Xmax-Xmin) |
| 158 | cell | boundary curvature | difference between X75% and X25% |
| 159 | cell | boundary curvature | sum(X^2) |
| 160 | cell | boundary curvature | sum(X^3) |
| 161 | cell | boundary curvature | mean(X.^2) |
| 162 | cell | boundary curvature | mean(X.^3) |
| 163 | cell | boundary curvature | mean(X.^4) |
| 164 | cell | boundary curvature | mean(X.^5) |
| 165 | cell | boundary curvature | sum((X-<X>)^2) |
| 166 | cell | boundary curvature | sum((X-<X>)^3) |
| 167 | cell | boundary curvature | mean((X-<X>)^2) |
| 168 | cell | boundary curvature | mean((X-<X>)^3) |
| 169 | cell | boundary curvature | mean((X-<X>)^4) |
| 170 | cell | boundary curvature | mean((X-<X>)^5) |
| 171 | cell | boundary curvature | peak number |
| 172 | cell | boundary curvature | gini coefficient |
| 173 | N-C orientation | boundary signature | mean |
| 174 | N-C orientation | boundary signature | median |
| 175 | N-C orientation | boundary signature | mode |
| 176 | N-C orientation | boundary signature | max |
| 177 | N-C orientation | boundary signature | min |
| 178 | N-C orientation | boundary signature | 25% percentile value |
| 179 | N-C orientation | boundary signature | 75% percentile value |
| 180 | N-C orientation | boundary signature | mean value above 75% percentile |
| 181 | N-C orientation | boundary signature | mean value below 25% percentile |
| 182 | N-C orientation | boundary signature | summation |
| 183 | N-C orientation | boundary signature | harmonic mean |
| 184 | N-C orientation | boundary signature | mean after eliminate 3% outlier |
| 185 | N-C orientation | boundary signature | mean after eliminate 5% outlier |
| 186 | N-C orientation | boundary signature | mean after eliminate 15% outlier |
| 187 | N-C orientation | boundary signature | mean after eliminate 25% outlier |
| 188 | N-C orientation | boundary signature | standard deviation |
| 189 | N-C orientation | boundary signature | CV - use mean |
| 190 | N-C orientation | boundary signature | CV - use median |
| 191 | N-C orientation | boundary signature | CV - use mode |
| 192 | N-C orientation | boundary signature | skewness |
| 193 | N-C orientation | boundary signature | kurtosis |
| 194 | N-C orientation | boundary signature | <|x-<x>|> |
| 195 | N-C orientation | boundary signature | range (Xmax-Xmin) |
| 196 | N-C orientation | boundary signature | difference between X75% and X25% |
| 197 | N-C orientation | boundary signature | sum(X^2) |
| 198 | N-C orientation | boundary signature | sum(X^3) |
| 199 | N-C orientation | boundary signature | mean(X.^2) |
| 200 | N-C orientation | boundary signature | mean(X.^3) |

-continued

| parameter ID | subcellular object | shape estimator category | estimator description |
|---|---|---|---|
| 201 | N-C orientation | boundary signature | mean(X.^4) |
| 202 | N-C orientation | boundary signature | mean(X.^5) |
| 203 | N-C orientation | boundary signature | sum((X-<X>)^2) |
| 204 | N-C orientation | boundary signature | sum((X-<X>)^3) |
| 205 | N-C orientation | boundary signature | mean((X-<X>)^2) |
| 206 | N-C orientation | boundary signature | mean((X-<X>)^3) |
| 207 | N-C orientation | boundary signature | mean((X-<X>)^4) |
| 208 | N-C orientation | boundary signature | mean((X-<X>)^5) |
| 209 | N-C orientation | boundary signature | peak number |
| 210 | N-C orientation | boundary signature | gini coefficient |
| 211 | N-C orientation | boundary signature | correlation |
| 212 | NC-ratio | basic | area |
| 213 | NC-ratio | basic | perimeter |
| 214 | NC-ratio | basic | long axis length |
| 215 | NC-ratio | basic | short axis length |
| 216 | NC-ratio | basic | orientation |
| 217 | NC-ratio | basic | solditiy |
| 218 | NC-ratio | basic | equvilant diameter |
| 219 | NC-ratio | basic | aspect ratio |
| 220 | NC-ratio | basic | circularity |
| 221 | NC-ratio | basic | roundness |
| 222 | NC-ratio | boundary signature | mean |
| 223 | NC-ratio | boundary signature | median |
| 224 | NC-ratio | boundary signature | mode |
| 225 | NC-ratio | boundary signature | max |
| 226 | NC-ratio | boundary signature | min |
| 227 | NC-ratio | boundary signature | 25% percentile value |
| 228 | NC-ratio | boundary signature | 75% percentile value |
| 229 | NC-ratio | boundary signature | mean value above 75% percentile |
| 230 | NC-ratio | boundary signature | mean value below 25% percentile |
| 231 | NC-ratio | boundary signature | summation |
| 232 | NC-ratio | boundary signature | harmonic mean |
| 233 | NC-ratio | boundary signature | mean after eliminate 3% outlier |
| 234 | NC-ratio | boundary signature | mean after eliminate 5% outlier |
| 235 | NC-ratio | boundary signature | mean after eliminate 15% outlier |
| 236 | NC-ratio | boundary signature | mean after eliminate 25% outlier |
| 237 | NC-ratio | boundary signature | standard deviation |
| 238 | NC-ratio | boundary signature | CV - use mean |
| 239 | NC-ratio | boundary signature | CV - use median |
| 240 | NC-ratio | boundary signature | CV - use mode |
| 241 | NC-ratio | boundary signature | skewness |
| 242 | NC-ratio | boundary signature | kurtosis |
| 243 | NC-ratio | boundary signature | <|x-<x>|> |
| 244 | NC-ratio | boundary signature | range (Xmax-Xmin) |
| 245 | NC-ratio | boundary signature | difference between X75% and X25% |
| 246 | NC-ratio | boundary signature | sum(X^2) |
| 247 | NC-ratio | boundary signature | sum(X^3) |
| 248 | NC-ratio | boundary signature | mean(X.^2) |
| 249 | NC-ratio | boundary signature | mean(X.^3) |
| 250 | NC-ratio | boundary signature | mean(X.^4) |
| 251 | NC-ratio | boundary signature | mean(X.^5) |
| 252 | NC-ratio | boundary signature | sum((X-<X>)^2) |
| 253 | NC-ratio | boundary signature | sum((X-<X>)^3) |
| 254 | NC-ratio | boundary signature | mean((X-<X>)^2) |
| 255 | NC-ratio | boundary signature | mean((X-<X>)^3) |
| 256 | NC-ratio | boundary signature | mean((X-<X>)^4) |
| 257 | NC-ratio | boundary signature | mean((X-<X>)^5) |
| 258 | NC-ratio | boundary signature | peak number |
| 259 | NC-ratio | boundary signature | gini coefficient |
| 260 | NC-ratio | boundary curvature | mean |
| 261 | NC-ratio | boundary curvature | median |
| 262 | NC-ratio | boundary curvature | mode |
| 263 | NC-ratio | boundary curvature | max |
| 264 | NC-ratio | boundary curvature | min |
| 265 | NC-ratio | boundary curvature | 25% percentile value |
| 266 | NC-ratio | boundary curvature | 75% percentile value |
| 267 | NC-ratio | boundary curvature | mean value above 75% percentile |
| 268 | NC-ratio | boundary curvature | mean value below 25% percentile |
| 269 | NC-ratio | boundary curvature | summation |
| 270 | NC-ratio | boundary curvature | harmonic mean |
| 271 | NC-ratio | boundary curvature | mean after eliminate 3% outlier |
| 272 | NC-ratio | boundary curvature | mean after eliminate 5% outlier |
| 273 | NC-ratio | boundary curvature | mean after eliminate 15% outlier |
| 274 | NC-ratio | boundary curvature | mean after eliminate 25% outlier |
| 275 | NC-ratio | boundary curvature | standard deviation |

-continued

| parameter ID | subcellular object | shape estimator category | estimator description |
|---|---|---|---|
| 276 | NC-ratio | boundary curvature | CV - use mean |
| 277 | NC-ratio | boundary curvature | CV - use median |
| 278 | NC-ratio | boundary curvature | CV - use mode |
| 279 | NC-ratio | boundary curvature | skewness |
| 280 | NC-ratio | boundary curvature | kurtosis |
| 281 | NC-ratio | boundary curvature | $<|x-<x>|>$ |
| 282 | NC-ratio | boundary curvature | range (Xmax-Xmin) |
| 283 | NC-ratio | boundary curvature | difference between X75% and X25% |
| 284 | NC-ratio | boundary curvature | $sum(X^2)$ |
| 285 | NC-ratio | boundary curvature | $sum(X^3)$ |
| 286 | NC-ratio | boundary curvature | $mean(X.^2)$ |
| 287 | NC-ratio | boundary curvature | $mean(X.^3)$ |
| 288 | NC-ratio | boundary curvature | $mean(X.^4)$ |
| 289 | NC-ratio | boundary curvature | $mean(X.^5)$ |
| 290 | NC-ratio | boundary curvature | $sum((X-<X>)^2)$ |
| 291 | NC-ratio | boundary curvature | $sum((X-<X>)^3)$ |
| 292 | NC-ratio | boundary curvature | $mean((X-<X>)^2)$ |
| 293 | NC-ratio | boundary curvature | $mean((X-<X>)^3)$ |
| 294 | NC-ratio | boundary curvature | $mean((X-<X>)^4)$ |
| 295 | NC-ratio | boundary curvature | $mean((X-<X>)^5)$ |
| 296 | NC-ratio | boundary curvature | peak number |
| 297 | NC-ratio | boundary curvature | gini coefficient |

Results

First, the training dataset was established. Approximately 12,000 cells from nine pancreatic cancer samples (five from primary tumors (PT), four from liver metastasis (LM)), as well as two normal pancreatic lines (NM) were plated in each of the well of a 24-well glass-bottom plate. After incubation, cells were fixed, permeabilized, and incubated with three different dyes. Actin filaments, nuclear DNA, and cellular cytoplasm were stained using, Alexa-Fluor Phalloidon 488, Hoechst, and the non-specific dye HCS CellMask Cy-5, respectively. Eighty one (9-by-9 square grid) fields of view of each well were visualized with a fully automated, computer-controlled epifluorescence microscope. For each well, 405 images (81 fields of view×5 channels) were acquired, covering a contiguous area of 26 mm$^2$. Images were acquired at 10× magnification to allow for the rapid imaging of a large number of individual cells. This approach was later validated on the same cells using a high-magnification lens and manual tracing.

Figure 15:
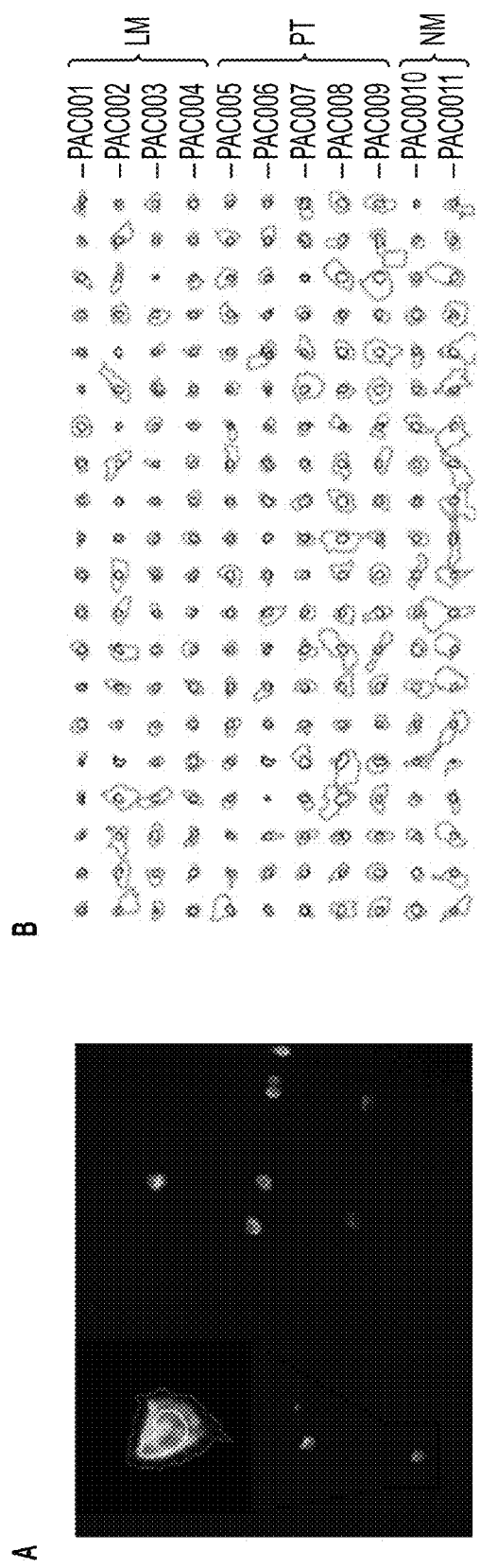
FIGS. 15 and 16 illustrate exemplary results of phenotyping analysis of individual human pancreatic cancer cells according to an embodiment of the current invention.
Figure 16:
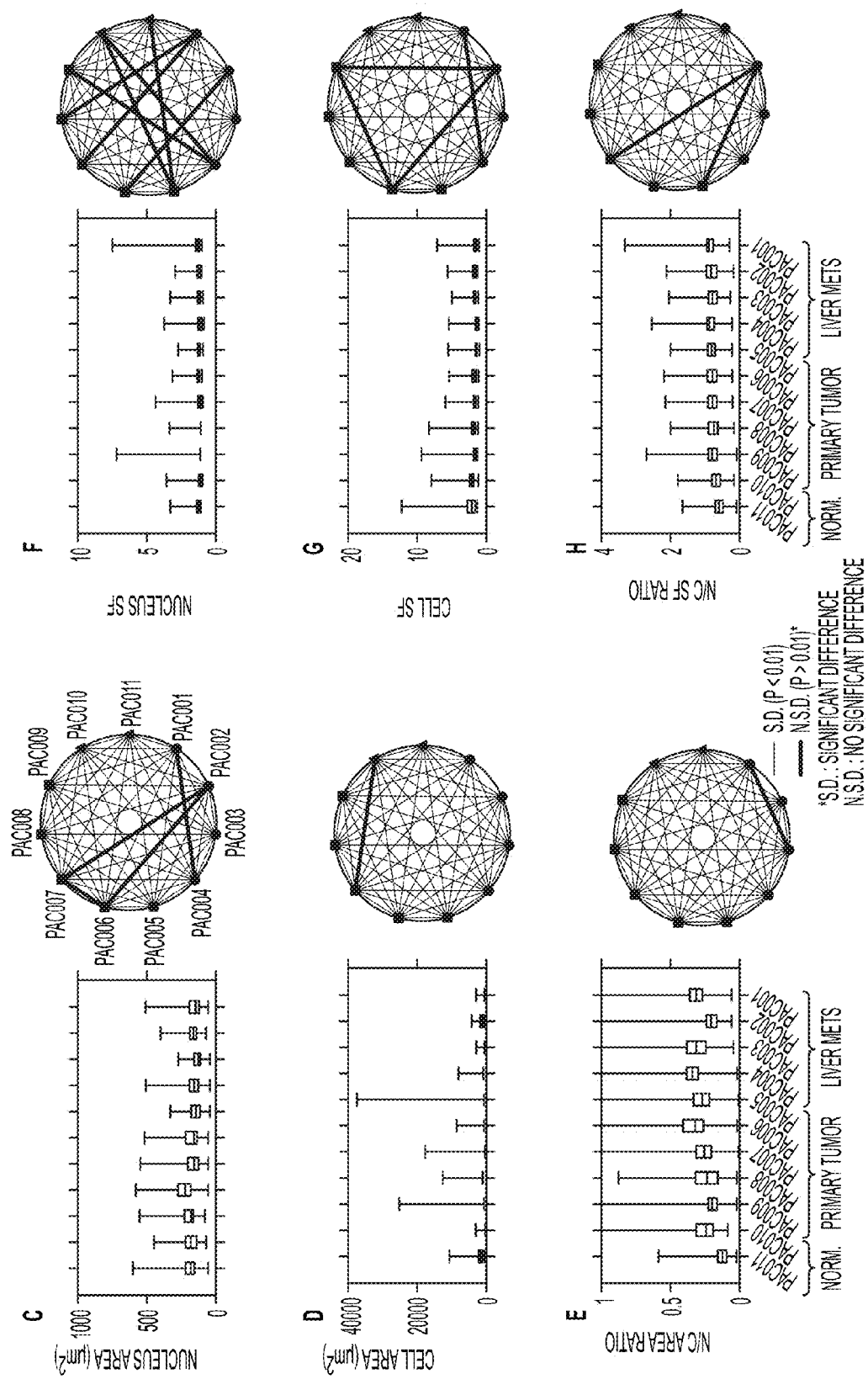

FIGS. 15 and 16 illustrate exemplary results of phenotyping analysis of individual human pancreatic cancer cells according to an embodiment of the current invention. (A). High-throughput phenotypic analysis of individual cells. Single-cell phenotyping is conducted by thresholding and binarizing three-color fluorescent images: nuclear DNA (DAPI) is used for nuclear morphometry, cytoplasmic stain (HCS cell mask) is used for cell segmentation and identification, and actin stain (phalloidin) is used for automated edge detection of the cell periphery and associated cell morphometry. (B). Non-parametric representation of randomly selected individual pancreatic ductal epithelial cells (HPDE), pancreatic normal epithelial cells (HPNE), ductal adenocarcinoma cells from the primary pancreatic tumor (stage IIB patients), and ductal adenocarcinoma cells from liver metastasis (stage IV patients). (C-H). Quantification of representative nuclear and cellular phenotypic parameters: nuclear area (C), cell area (D), nucleus/cell area ratio (E), nuclear shape factor (F), cell shape factor (G), ratio of nucleus/cell shape factor (H). At least 1,000 cells were examined per sample. Significance of measurements is shown in the right of each shape measurement plot. P value is computed using two way t-test and 0.01 is set as threshold for distinguish the sample cells has significance difference (P<0.01) or no significant difference (P>0.01). All 9 samples is listed in the along a circle and the connected line to other cell samples represent the significant difference (cyan) or non-significant difference (magenta). There is no morphology signature from using area and shape factor to distinguish the liver mets and primary tumor; i.e. most liver mets or primary has non-significant difference connection between each other but has significant difference between different group.

Quantification of nuclear and cellular phenotypic parameters was conducted using a custom developed, high-throughput phenotyping Matlab-based code. Issues related to non-uniform illumination of the samples were circumvented, image contrast was enhanced, and cells and nuclei were segmented using a multiple-channel imaging method. In particular, cell boundaries determined using the phalloidin channel as F-actin gave a significantly stronger signal at the cell boundary than at the cell center, differentiating the boundary from the cytoplasm with less bias than a more homogenous dye (such as HCS cell mask)(A). In contrast, HCS cell mask intensity was concentrated around the nucleus—the thicker region of the cell—and decayed towards the edge of the cell; Quantitative estimation of phenotypic parameters was validated by assessing whether their values were statistically similar to the values of the same parameters obtained by manually tracing the cells and nuclei and values of the same parameters evaluated from high-magnification images of the same cells.

Visual inspection of randomly selected cells showed apparent differences among PT, LM, and NM cells (B). However, quantification of several commonly used morphological parameters (area, roundness, nucleus:cell area and roundness ratios) revealed no overt and consistent differences between PT and LM cells (C-H, global statistical significance is shown in the right), which prompted defining additional cell- and nucleus-associated parameters. The need for introducing non-conventional parameters is best illustrated as follows.

Figure 17:
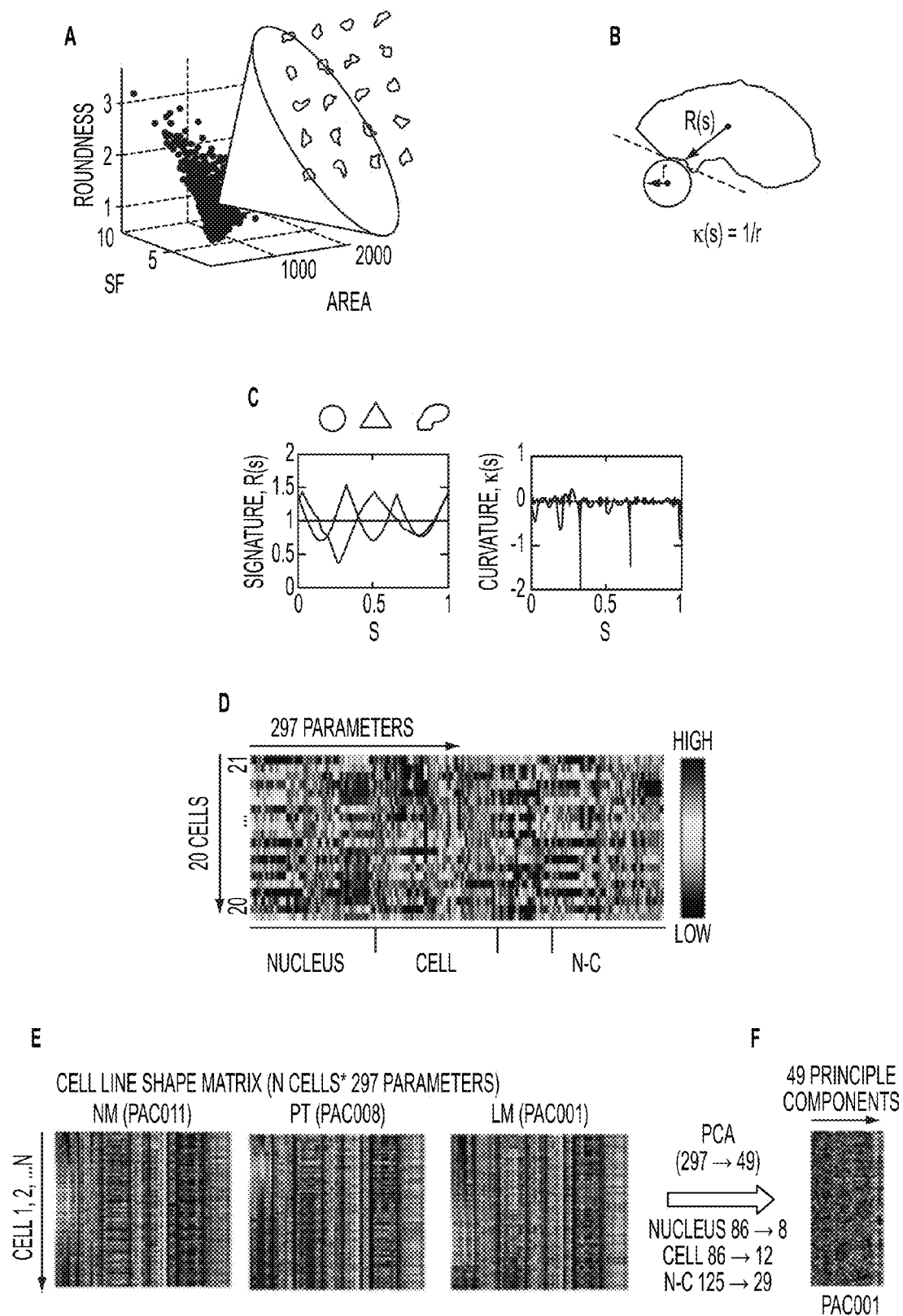
FIGS. 17 and 18 illustrate high-definition (HD) quantitative phenotyping according to an embodiment of the current invention.
Figure 18:
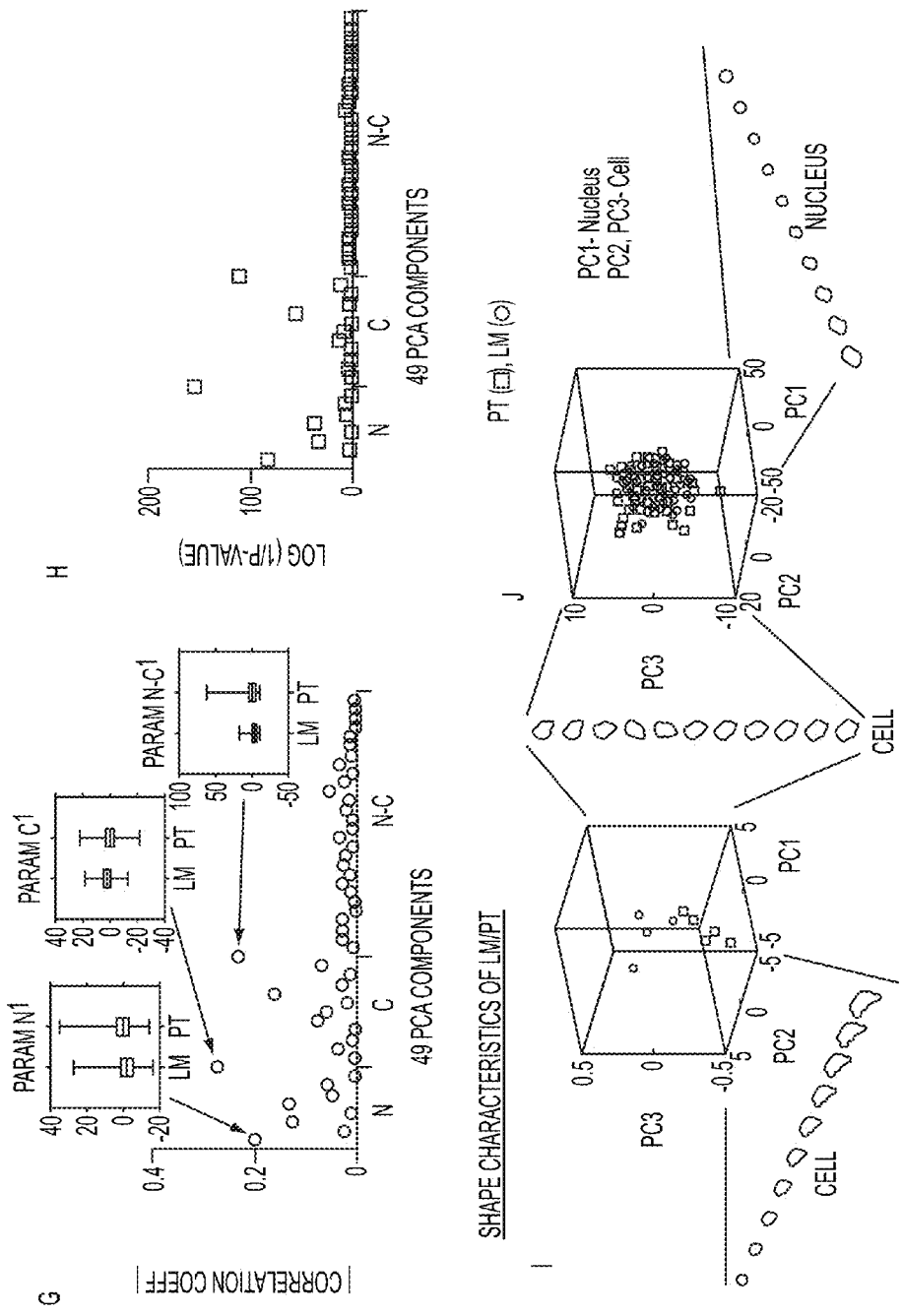

FIGS. 17 and 18 illustrate high-definition (HD) quantitative phenotyping according to an embodiment of the current invention. (A) illustrates an exemplary three-parameter space image of twenty cells according to an embodiment of the current invention. The twenty cells are of very similar cell size, shape factor, and roundness constituting a minuscule region representing a total of 1700 PANC001 cells. Yet, these 20 cells showed overtly different shapes, clearly not captured by these three parameters or other conventional parameters. Therefore, in addition to conventional shape and size parameters, we defined four additional general categories of cellular and nuclear phenotypes to describe the shape, size, and relative position of cell and nuclei: (i and ii) cellular and nuclear "roughness" and "curvature", (iii) N/C ratios, and (iv) nuclear position in the cell. Conventional cellular and nuclear morphology parameters included apparent surface area, perimeter, shape factor, aspect ratio, etc. Cellular and nuclear roughness was defined by transforming the 2D boundary of each cell and nucleus into a corresponding 1D curve.

(A) is an illustration of how individual HPNE cells with values of cell shape, cell roundness and cell area within an extremely narrow range can already display high variability, yet only represent a minuscule fraction of the arbitrarily chosen 3-parameter space (cell shape, cell roundness, and cell area) obtained with 1,700 HPNE cells shown in (A). This justifies the need for additional phenotypic parameters.

(B) illustrates an exemplary image of a shape transformed into a curve according to an embodiment of the current invention. The shape of the resulting curve was characterized by 39 additional parameters, including mean value, maximum value, minimum value, mode, and less conventional parameters like kurtosis and the Gini coefficient. Cellular and nuclear curvature was defined by first obtaining smoothed sets of boundary coordinates, which were obtained by convolving the raw object boundary coordinates in the x- and y-directions with a discrete 1D Gaussian smooth filter with window size of 11 and standard deviation of 1. The shape of the curvature was obtained using the same transformation as for cell and nucleus roughness.

(B) demonstrates additional shape parameters, signature of a shape and curvature to describe cell shapes.

(C) illustrates an exemplary curvature and roughness of a circle, a triangle and a real cell object according to an embodiment of the current invention. Nucleus:cytoplasm ratios (of size, shape, etc), which are widely used for the pathological assessment of cancerous tissues (REFs), was also calculated. Finally, the relative nuclear location was characterized using a polar coordinate system with an origin at the center of the nucleus. In all, 297 primary nuclear and cellular parameters were estimated to quantitatively characterize cell properties at the single-cell level. (C) demonstrates additional shaping data using model shapes; circle, triangle and a real irregular cell shape. Further, these 1-D curves from signature and curvature are represented by several parameters and along with different categories of shape from nucleus, cell and nucleus-cell distribution and ratio, which then describe a single cell with 297 phenotype parameters.

Subjecting these 20 seemingly cells of similar cell size, shape factor, and roundness to these 297 measurements indeed showed distinct morphology signature of each single cell.

(D) illustrates exemplary morphology signatures of various cells based on morphology parameters according to an embodiment of the current invention. (D) may illustrate a heat map showing 297 phenotypes for the 20 cells shown on (A). Each column represents a phenotype; each line represents a single individual cell. The cells are shown along the y-axis and the parameters are shown along the x-axis. This multiple-parameter analysis was extended to 500 randomly selected cells from each of the nine pancreatic cancer samples, which were sorted by nuclear DNA intensity level (see details under Methods). Phenotypic maps were generated and sub-categorized into nuclear phenotypes (columns 1-86), cellular phenotypes (columns 87-173), parameters describing the spatial organization of the nucleus within the cell (columns 173-212), and nuclear/cellular parametric ratios (columns 213-297) for a total of 297 phenotypes. Intensity values correspond to the lowest and highest values of each phenotype after normalization of each phenotype to span values between −1 and 1.

(E) illustrates exemplary heat maps of various cells according to an embodiment of the current invention. Visual inspection of the resulting heat map from 500 randomly selected cells among three cell lines in different classification suggested a phenotypic pattern describing each sample. The map shows 500 randomly selected cells (rows) described by 297 phenotypes (columns) for each pancreatic cell line. Cells were ordered from the lowest value (top row) to the highest value (bottom row) of nuclear DAPI intensity. Principle component analysis (PCA) analysis was further implemented into morphological dataset constructed from these 9 pancreatic cancer cell lines to reduce the dimensionality and repeatability among dataset while preserving the 90% cumulative energy (not sure the wording). To be noted, principle components are obtained from applying PCA into three different categories of morphology parameters and they are nucleus parameters, cell parameters and nucleus-cell relative distribution parameters. There are 8 identified principle components to represent nucleus shape out of original 86 parameters for nuclei, and 12 principle component for cells (out of 86 parameters), and 29 for nucleus-cell distribution (out of 125 parameters)

(F) illustrates exemplary morphology signatures based on principle components of various cells according to an embodiment of the current invention. Different arbitrary values were assigned for all LM and PT cells from different cell lines and computed correlation coefficient in single cell level to identify the principle components that can indicate LM from PT. There are several principle components found which have significantly higher correlation level than others. Principle component analysis (PCA) was applied on this dataset to reduce the high correlated parameters among 297 parameters while preserving the 90% variation in the sample. To note, each category of parameters is processed PCA with themselves. There are 8 identified principle components to represent nucleus shape out of original 86 parameters, and 12 principle component for cells (out of 86 parameters), and 29 for nucleus-cell distribution (out of 125 parameters).

(G) illustrates exemplary principle components with higher levels according to an embodiment of the current invention. Different arbitrary values were assigned for all LM and PT cells from different cell lines and computed correlation coefficient in single cell level to identify the principle components that can indicate LM from PT. There are several principle components are significantly higher correlation level than others.

(H) illustrates an exemplary scatter plot showing the corresponding p-value from correlation test according to an embodiment of the current invention. (I) illustrates an exemplary 3-D scatter plot of mean value of three-highest cancer stage-correlated principle components according to an embodiment of the current invention. The principle components have minimum mutual correlation from 9 different cancer cell lines (the highly correlated N-C category principle components is strongly correlated with nucleus parameters (□>0.9) and hence is not selected). The separation between LM (circle) cell lines and PT (square) cell lines is shown in this 3D-plot using the same principle component for 100 random selected single cells for each different cell lines. This result shows the great variability exist in single cell level with difficult visualization to distinguish LM from PT.

(J) illustrates an exemplary 3-D scatter plot of different shape of nucleus/cell values according to an embodiment of the current invention. The different shapes are among a single principle component while minimizing the difference among others parameters and plotted along the different principle component axis. In PC2 is clearly size dependent. In PC1 and PC3, there may be more shaping dependent. The 3-D scatter plot uses the same principle component for 100 random selected single cells for each different cell lines. This result shows the great variability exist in single cell level with difficult visualization to distinguish LM from PT. To conclude, the results show a morphological trait of nucleus and cell is existing in between pancreatic liver met cells and pancreatic primary tumors cells. It has been reported that there are no mutated gene signature or specific molecular markers marking liver mets from pancreatic cancer and pancreatic primary tumor using 24 advanced cell lines derived from pancreatic cancer (REF). This morphological study only uses 9 cell lines among these 24 cell lines. Further confirmed is no somatic mutation signature either in these 9 cells by collecting the mutated that occur more than once among these 9 cancer cell lines.

Figure 19:
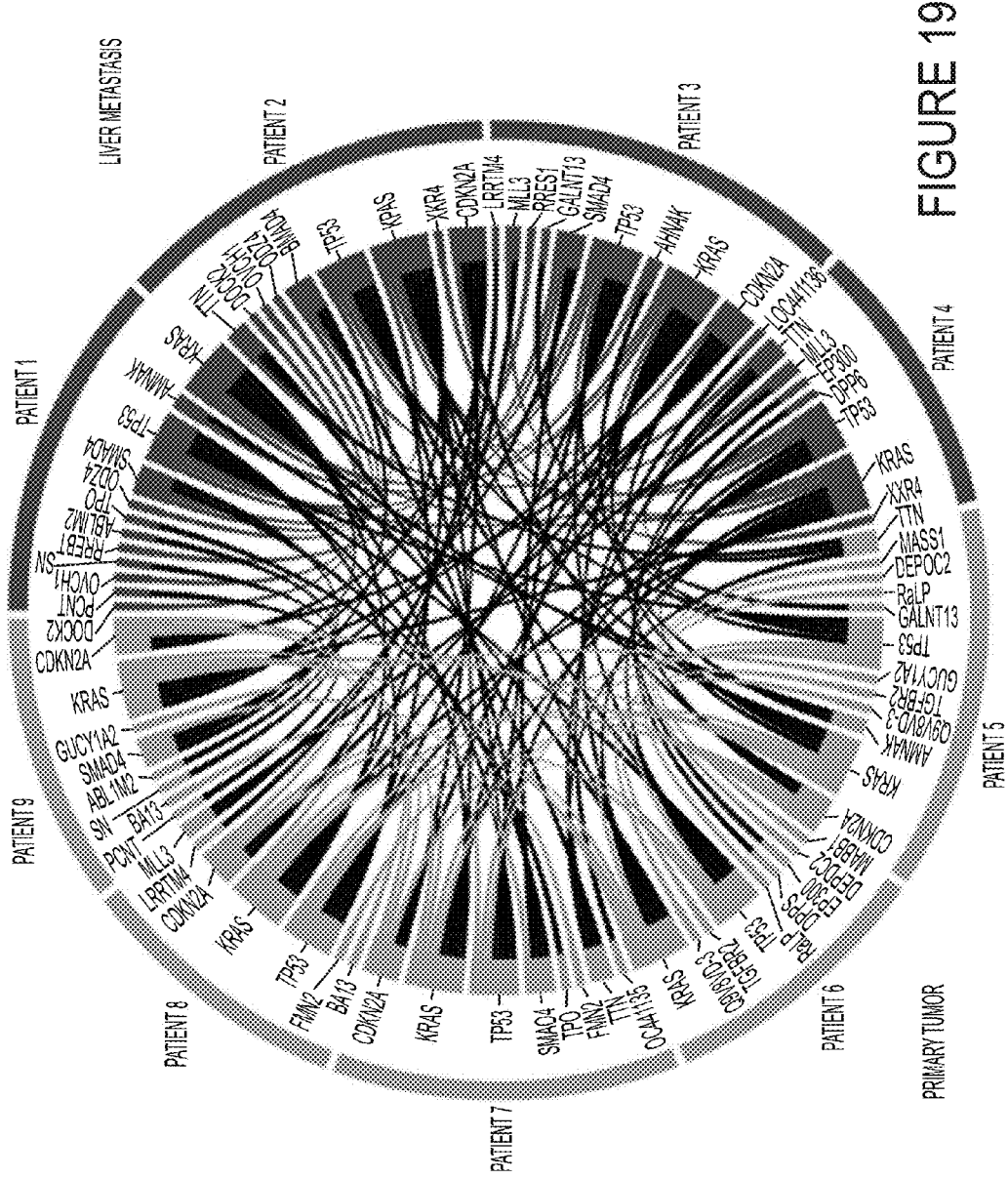
FIG. 19 illustrates repeated mutated gene hits for 9 different patient-derived primary and metastatic cell lines according to an embodiment of the current invention.

FIG. 19 illustrates repeated mutated gene hits for 9 different patient-derived primary and metastatic cell lines according to an embodiment of the current invention. The patient-derived cancer cells that were used in this study had between 20-70 mutated genes. To identify whether a mutated gene signature existed and could be used to differentiate between primary tumor and liver met-derived cells, recurrent mutations were from each line were listed around the plot. A line connection is drawn for the same mutated gene from different patient derived cells—a line for mutation connections between liver mets, a line for primary tumor lines, and a line for common mutations between primary tumor and liver met-derived cells. If a signature were to emerge, more of the first two connections than the latter connection would expect to be seen. All the cells had mutated Kras and most had mutated TP53, but no signature presented between primary tumor and liver met-derived cells.

Among these 9 cell lines (5PT, 4LM) the highest occurrence mutated genes is following; Kras mutation occurs in all cancer cell lines, TP53 mutation occurs in 8 cell lines (4 PT, 4 LM), Smad4 mutation has in 5 cell lines (2PT, 3LM) and CDkN2A mutations has in 6 cell lines (4PT, 2LM) and TTN mutation (2PT, 2LM). Therefore, we did not identify any distinct mutated gene between PT and LM among these 9 cell lines.

Importantly, the assay was subject to a battery of test of reproducibility and robustness against a wide range of potential variability. Potential variations in the measurements of cellular and nuclear properties were assessed as a function of user (i.e. the same samples were assayed by two different trained users), light microscope (i.e. the same samples were assayed by the same user using two different microscopes), positioning of the sample on the microscope stage (i.e. the same sample was assayed, then removed from the microscope, rotated, and re-assayed on the same microscope), biological repeats (i.e. different frozen vials from same patient different were assayed by the same user using the same microscope), as well as passage number of the cells, fixation method, and shelf life of the fixed sample.

These phenotypic patterns, however, still did not fully describe cell populations.

Figure 20:
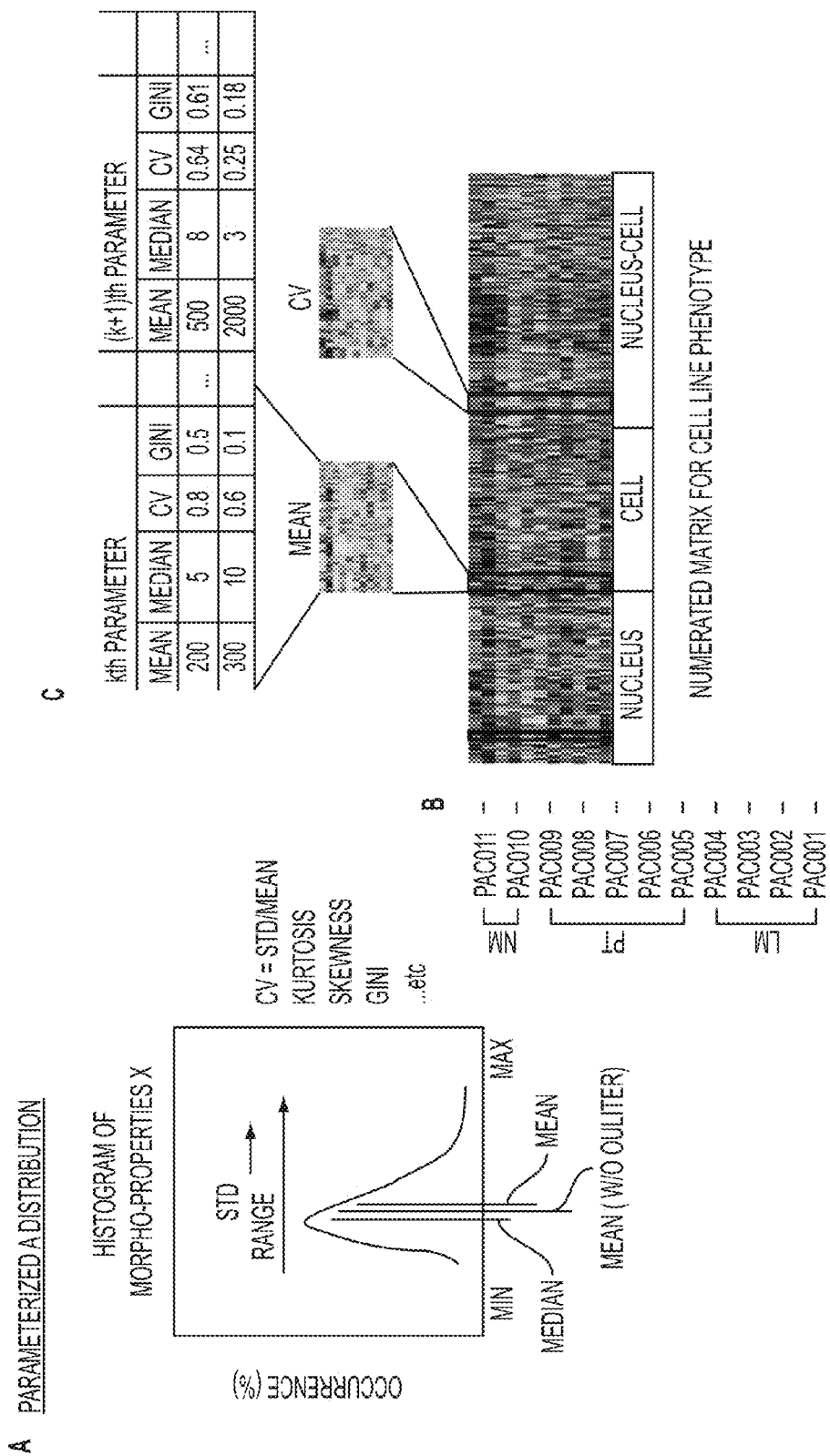
FIGS. 20 and 21 illustrate an exemplary shape distribution of phenotypes according to an embodiment of the current invention.
Figure 21:
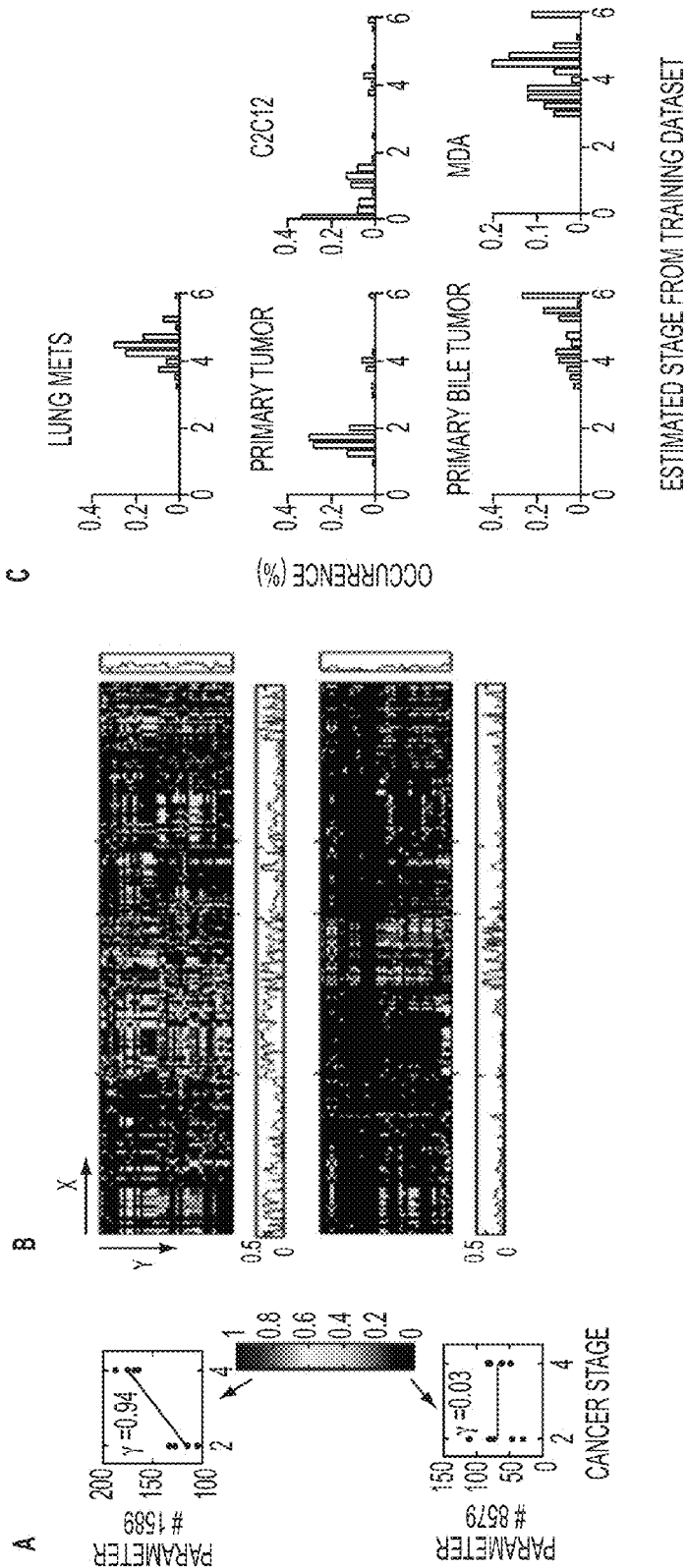

FIGS. 20 and 21 illustrate an exemplary shape distribution of phenotypes according to an embodiment of the current invention. Each of the 297 distributions of cell properties was further characterized by 40 descriptors, including mean value, standard deviation, coefficient of variation, Gini coefficients, and median. After generating a heat map of the now 11,880 (=297×40) parameters for all 11 samples, consistent differences between PT and LM samples clearly emerged, as shown in FIG. 20. Values of nuclear and cell morphological parameters and distribution descriptors tended to be higher in PT samples when compared to LM samples. Interestingly, the PAC005 cell line, derived from a primary tumor, showed a signature more like the liver metastasis-derived lines. The heat map shown displays variations in mean values of cell and nuclear properties across the training 11 samples. Many differences between PT and LM cells could stem from outliers. To better resolve these parameters, we generated comparative phenotypic maps for the mean values of the top 75% outliers, media values, and GINI coefficients of the 297 measured phenotypes. Once again, these maps showed that the majority of differentiators between the PT's and LM's were nuclear-related parameters.

To assess potential correlations between cell phenotypes and cancer stage, Pearson correlation coefficients were calculated between the 11,880 measurements on 11 samples and cancer stage. It was found that cell and nuclear data were more highly correlated with cancer stage than cell and nuclear orientation parameters and nuclear/cell ratios, as shown in FIG. 21. As negative controls, it was verified that Pearson coefficients between the morphological data and age and sex were low, which suggested that cell morphological changes are more associated with cancer staging than with either age or sex.

To validate these results, these newly identified highest phenotypic metastatic correlates were subjected to a stringent blind test. The developers of the assay were given cells of unknown oncological status (normal vs. non-metastatic cancer vs. metastatic cancer), unknown species (human, rodent), and unknown type (pancreatic, fibroblasts, myoblasts). It also turned out that one of the validating tests was one of the 11 previously tested samples.

Figure 22:
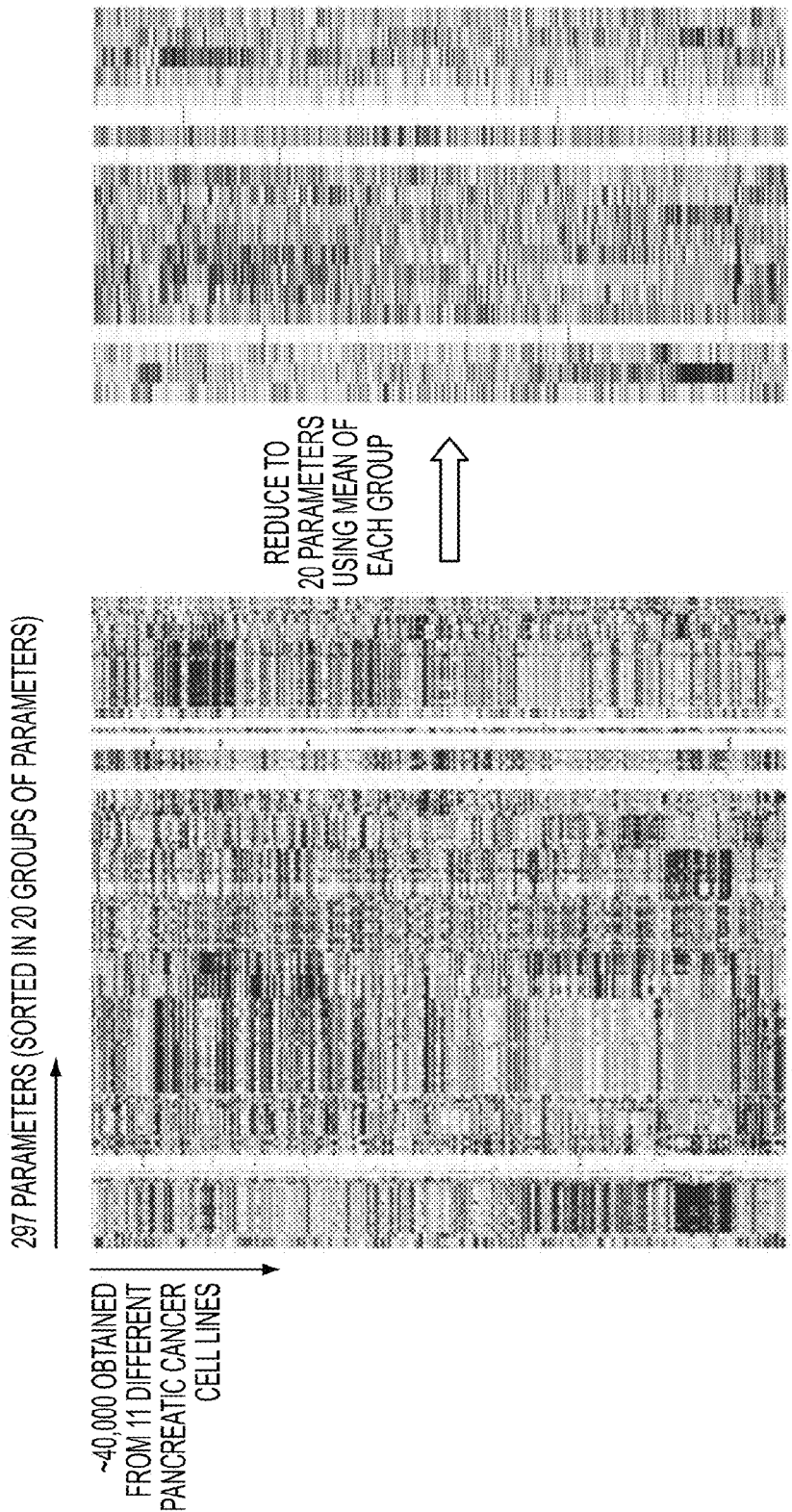
FIG. 22 illustrates an exemplary process of reducing the dimensions of a heat map using clustering according to an embodiment of the current invention.

FIG. 22 illustrates an exemplary process of reducing the dimensions of a heat map using clustering according to an embodiment of the current invention. The heat map on the left may have individual cells in the y-axis and morphological parameters for the cells in the x-axis. Lighter shading of areas may indicate higher values and darker shading may indicate lower values. The morphological parameters may be sorted into groups of parameters. In this example, 297 parameters of 40,000 cells from 11 different pancreatic cancer cell lines are sorted into 20 groups of parameters using the mean of the morphological parameter for each group. The resulting heat map with reduced dimensions is shown on the right.

Figure 23:
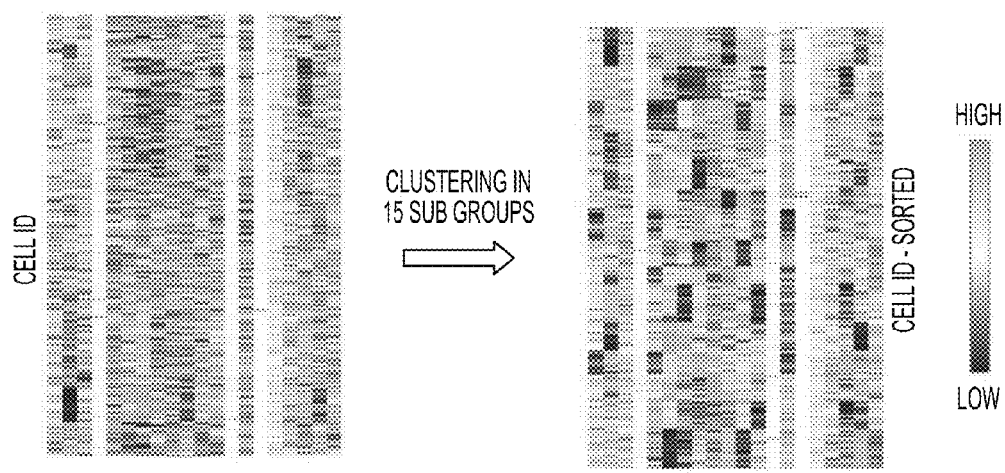
FIG. 23 illustrates an exemplary process of clustering cells into cell groups according to an embodiment of the current invention.

FIG. 23 illustrates an exemplary process of clustering cells into cell groups according to an embodiment of the current invention. Cells in a reduced dimension heat map may be clustered into cell groups based on determining cell groups in the cells. FIG. 22 shows an example where principle component analysis (PCA) reduced parameters of cell shape are selected, including size, factor, curvature, and roughness from nucleus and cells. There are approximately 36,000 cells from 9 different cell lines shown. Clustering analysis is applied to identify 15 cell groups, where on the right the heat map is shaded for PCA reduced parameters for a cell basis using the cell group closest to the PCA reduced parameter for the cell.

Figure 24:
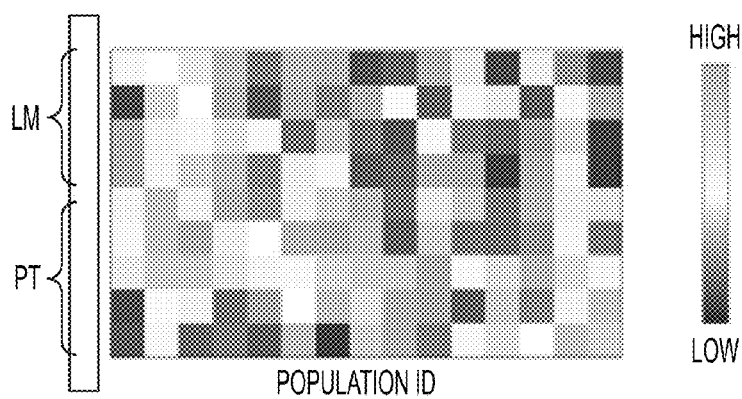
FIG. 24 illustrates an exemplary heat map and histogram based on cell groups according to an embodiment of the current invention.
Figure 24:
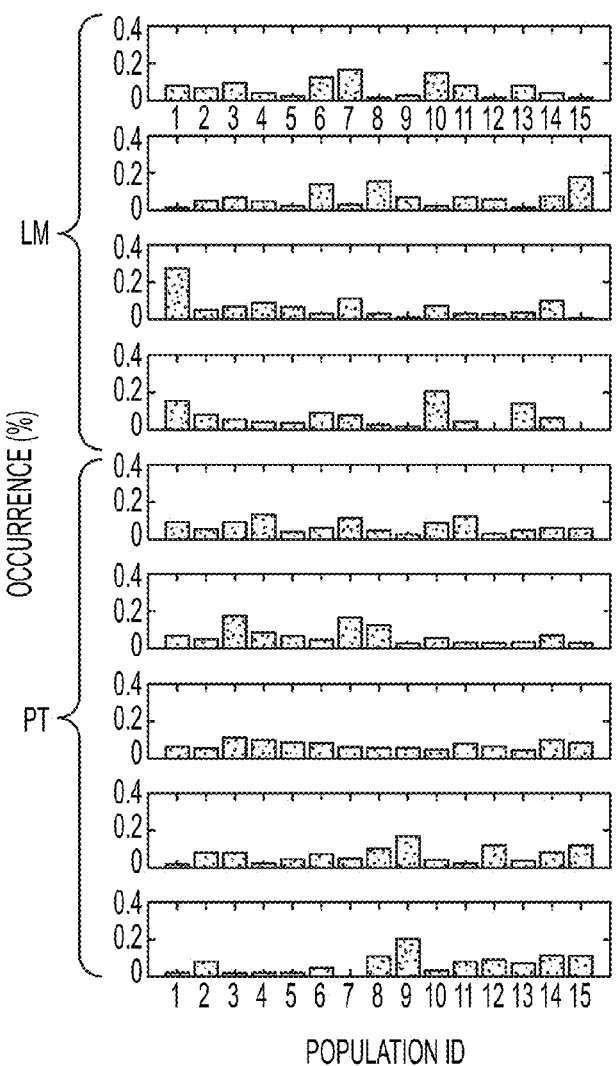

FIG. 24 illustrates an exemplary heat map and histogram based on cell groups according to an embodiment of the current invention. The heat map shows the percentage of each cell line (shown in the y-axis) by the different cell groups (shading) for each clustered parameter (x-axis) by cell line.

Figure 25:
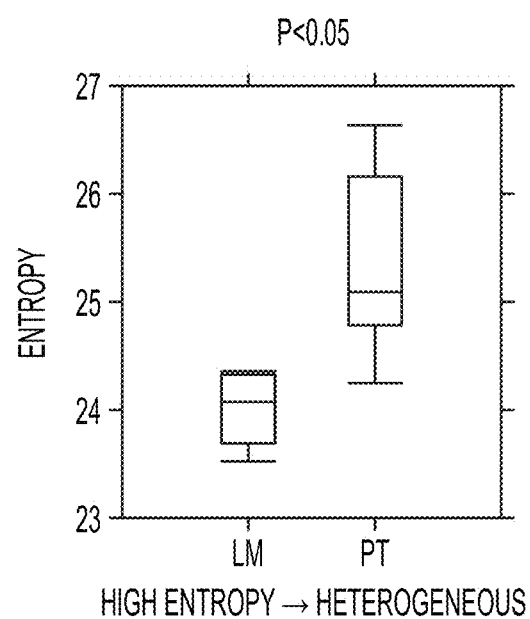
FIG. 25 illustrates an exemplary chart showing entropy according to an embodiment of the current invention.

FIG. 25 illustrates an exemplary chart showing entropy according to an embodiment of the current invention. Entropy may correspond with heterogeneity of the cells, where more heterogeneity corresponds with greater entropy. Entropy may be estimated in the following example. Say there are i subgroup in a set of cells and pi is the probability for cells being in the group i. Entropy (S) can be estimated as following equation S=sum (pi*log(pi)) where sum (pi)=1. Entropy may be used to determine if a group of cells correspond with metastatic cells or not. For example, based on the results shown in the chart, if entropy is 24, a group of cells may be determined to more likely correspond with LM cells.

Cell Phase Example

Here a microscope-based assay is used to measure both the cell cycle phase of a thousand of individual cells and their associated cellular and nuclear properties rapidly and simultaneously. This assay demonstrates that population-averaged cell morphological properties strongly depend on cell-cycle phase and could be written as linear combinations of cell-cycle fractions and phase-dependent morphological properties. This assay reveals that key structural nuclear-envelope proteins (Nesprins, Lamin A/C) are regulators of nuclear size and shape partially because they affect cell cycle distribution; they are not bona fide (intrinsic) regulators of nuclear morphology [Stewart-Hutchinson, P. J., Hale, C. M., Wirtz, D. & Hodzic, D. Structural requirements for the assembly of LNC complexes and their function in cellular mechanical stiffness. *Experimental Cell Research* 314, 1892-1905 (2008); Johnson, B. R. et al. A-type lamins regulate retinoblastoma protein function by promoting subnuclear localization and preventing proteasomal degradation. *Proceedings of the National Academy of Sciences of the United States of America* 101, 9677-9682 (2004); Dechat, T. et al. Alterations in mitosis and cell cycle progression caused by a mutant lamin A known to accelerate human aging. *Proceedings of the National Academy of Sciences* 104, 4955-4960 (2007)].

Vice versa, this assay indicates that inhibition of cell cycle regulator cyclin-dependent kinase 4/6, cdk4/6, are also nuclear morphological regulators, and that some commonly used cell cycle synchronization methods have significant and lasting effects on cell and nuclear morphology [Moseley, J. B. & Nurse, P. Cdkl and cell morphology: connections and directions. *Current Opinion in Cell Biology* 21, 82-88 (2009); Polyak, K. et al. p27Kip1, a cyclin-Cdk inhibitor, links transforming growth factor-beta and contact inhibition to cell cycle arrest. *Genes & Development* 8, 9-22 (1994); Cooper, S., Iyer, G., Tarquini, M. & Bissett, P. Nocodazole does not synchronize cells: implications for cell-cycle control and whole-culture synchronization. *Cell and Tissue Research* 324, 237-242 (2006)].

Results and Discussion

Measurements of Cell Cycle Distributions In Situ

Figure 26:
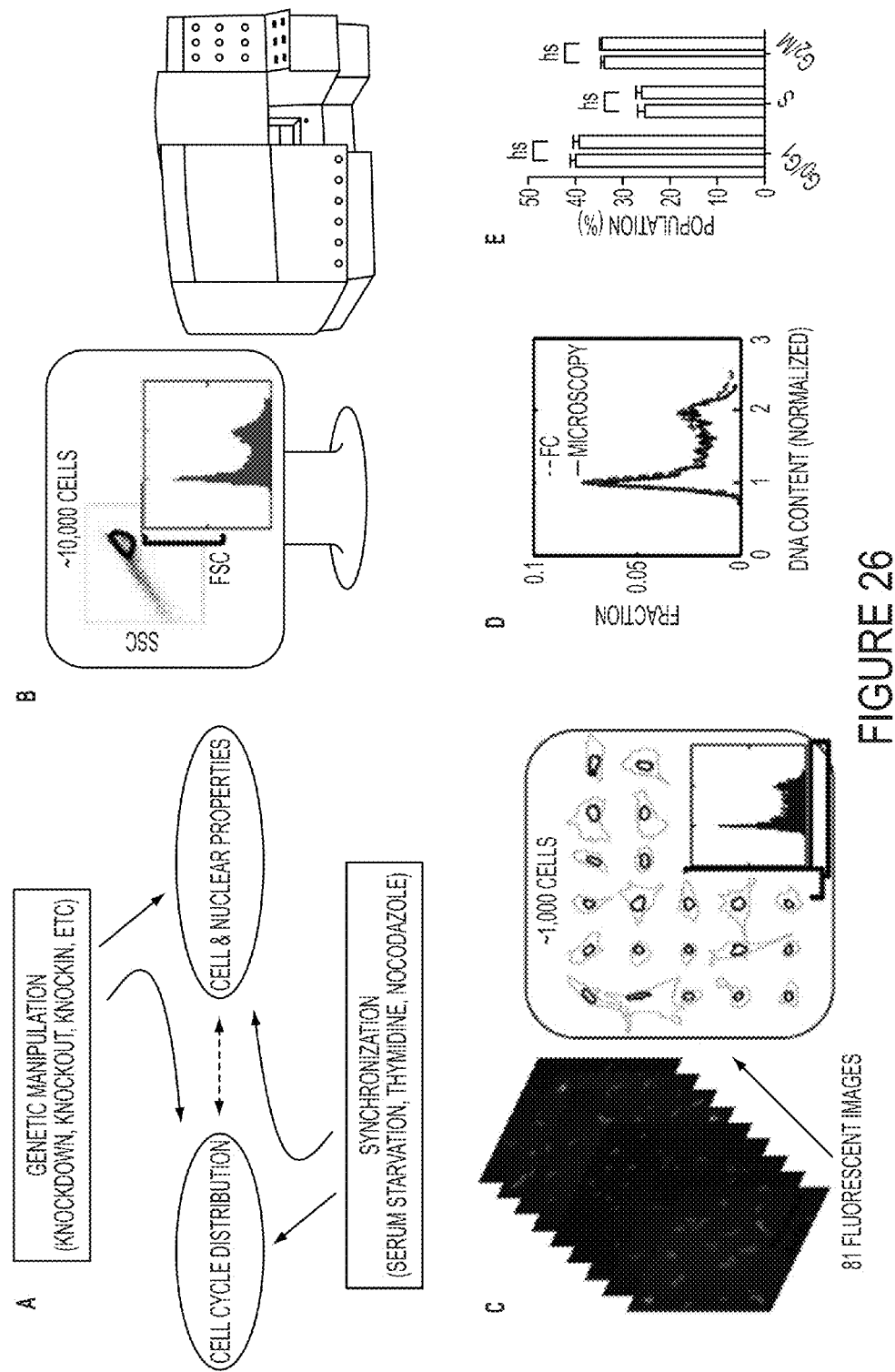
FIG. 26 illustrates measurement of cell cycle phase distribution in situ according to an embodiment of the current invention.

FIG. 26 illustrates measurement of cell cycle phase distribution in situ according to an embodiment of the current invention). (A) Schematic showing that genetic manipulations (knockdown, knockout, etc.) or cell treatments (e.g. serum starvation, drugs, etc.) designed to change cell cycle distribution can inadvertently affect cell properties (e.g. nuclear shape) and, vice versa, cell manipulations meant to change cell properties can inadvertently affect cell cycle distribution. These possible confounding effects can be measured simultaneously using the method presented in this study. (B) Conventional FC analysis. Mouse myoblasts (c2c12) were fixed and their nuclear DNA was stained with Hoechst 33342. Inset. DNA stain intensity distribution of ~10,000 cells was analyzed through user-dependent gating (circle) of forward-scatter (FSC) and side scatter (SSC) intensities. (C) Our Microscopy-based high-throughput assay used in these studies. Eight one fields of four-channel fluorescence/phase contrast images were collected (only DNA channel and actin channel are shown here) to analyze the intensity of ~1,200 nuclei and simultaneously measure cell and nuclear properties (cell size, nuclear size, nuclear shape, etc.) in the same individual cells through edge detection of cell boundaries (contours) and nuclear boundaries (contours). Inset. This analysis produced a DNA stain intensity distribution (profile). (D) Normalized DNA stain intensity distribution of c2c12 cells obtained from FC analysis and our microscopy-based assay. (E) Proportion of cells in the $G_0/G_1$, S, and $G_2/M$ cell-cycle phases, as measured by conventional FC analysis and by microscopy-based analysis. NS: non-significant differences; $P>0.05$ (t-test for phase-to-phase comparison). For (E), three biological repeats on different cells were conducted for both FC analysis and microscopy-based analysis.

First we established and validated a microscopy-based method to measure the cell-cycle phase in individual adherent cells. Mouse myoblasts (c2c12) were plated on a glass-bottom dish. After 48 h incubation, cells were fixed, permeabilized, and incubated with nuclear DNA stain Hoechst33342, a dye routinely used in FC analysis of cell cycle distribution (FIG. 1B), [Jayat, C. & Ratinaud, M.-H. Cell cycle analysis by flow cytometry: Principles and applications. *Biology of the Cell* 78, 15-25 (1993); Darzynkiewicz, Z. & Juan, G. in Current Protocols in Cytometry (John Wiley & Sons, Inc., 2001)] as well as additional stains to detect actin filament structures at the cell cortex and delineate the cytoplasm for cell edge detection (C).

The dish was placed on a customized scanning fluorescence light microscope equipped with a motorized stage (C) Importantly, to quantitatively determine cell cycle phases at single-cell resolution, we introduced a calibration step to correlate measured Hoechst light intensity in the nucleus to DNA content (see Materials and Methods below). Light intensities from solutions of Hoechst molecules were measured using the same customized scanning microscope used subsequently to measure cell properties in the same cells (C).

For each dish, reference illumination and dark images were collected and used to normalize the intensities in the illumination field (see additional details under Methods). This calibration step addressed potential non-uniform illumination of the samples by the light microscope and the non-uniform recording by the optical train of the microscope and the CCD camera. [Wu, P.-H., Nelson, N. & Tseng, Y. A general method for improving spatial resolution by optimization of electron multiplication in CCD imaging. *Opt. Express* 18, 5199-5212 (2010)].

The cell cycle-phase distribution of c2c12 mouse myoblasts measured by this microscopy-based assay was carefully compared to the cycle-phase distribution obtained from conventional FC analysis (D and E) [Jayat, C. & Ratinaud, M.-H. Cell cycle analysis by flow cytometry: Principles and applications. *Biology of the Cell* 78, 15-25 (1993)]. For both methods, cells were fixed and their DNA was stained with the same nuclear DNA dye Hoechst 33342. Even though different numbers of cells were assessed (~10,000 cells for FC vs. 1,000-2,000 for our assay), cell cycle distributions were statistically indistinguishable (D and E). By zooming in on the $G_0/G_1$ phase peak, we found that the coefficients of variation (CV) of these cell sub-populations using Gaussian fits were close, and that the signal-to-noise ratios (1/CV) were highly similar (E) and Table 1 below) [Ng, B. L. & Carter, N. P. Laser excitation power and the flow cytometric resolution of complex karyotypes. *Cytometry Part A* 77A, 585-588 (2010)].

TABLE 1

|  | Population in $G_0/G_1$ | Population in S | Population in $G_2/M$ | SNR | $R^2$ |
|---|---|---|---|---|---|
| FC | 40.3% | 25.6% | 34.1% | 8.6 | 0.97 |
| FC (sampled) | 39.4% | 28.5% | 32.1% | 9.1 | 0.88 |
| Microscopy | 39.3% | 26.1% | 34.6% | 8.3 | 0.92 |

* SNR represents signal to noise ratio

Table 1 shows resolution of cell cycle phase determination: FC vs. microscopy-based assay. Fractions of cells in each cell cycle phase estimated by FC analysis and the microscopy-based assay showed no statistical difference (FIG. 26). The resolution of the cell cycle-phase distributions obtained by these two methods was estimated by Gaussian fits of the $G_0/G_1$ peaks. The coefficient of variation (CV) is defined as the ratio of standard deviation over mean value. Signal to noise ratio (SNR) is the reciprocal of the coefficient of variation. Cells in the $G_0/G_1$ phase were analyzed by: (i) flow cytometry (denoted FC) using 10,000 cells, (ii) flow cytometry using the same number of cells as analyzed by our microscopy-based assay (1,000 cells; denoted FC (sampled)), and (iii) by our microscopy-based assay.

Figure 27:
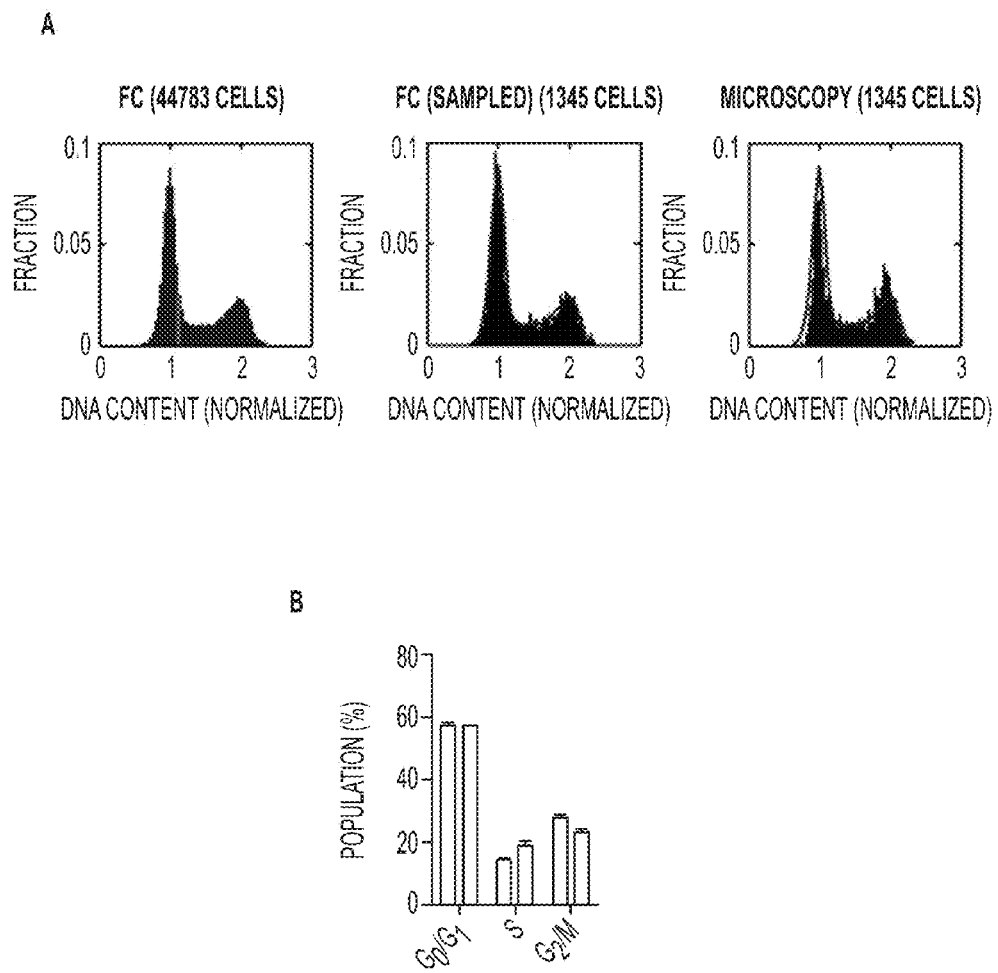
FIG. 27 illustrates cell cycle distributions of MD-MB-231 cells verified by flow cytometry (FC) analysis according to an embodiment of the current invention.

FIG. 27 illustrates cell cycle distributions of MD-MB-231 cells verified by flow cytometry (FC) analysis according to an embodiment of the current invention. A direct comparison between FC analysis and the analysis using our assay also showed statistically indistinguishable cycle distributions for human breast carcinoma cells (MD-MB-231). (A) Cell cycle distribution of human breast cancer cells (MDA-MB-231) were measured by both FC and the microscopy assay. The number of analyzed cells is indicated above each graph. (B) Fractions of cells in each phase of the cell cycle quantified with our microscopy-based assay and compared to FC.

Figure 28:
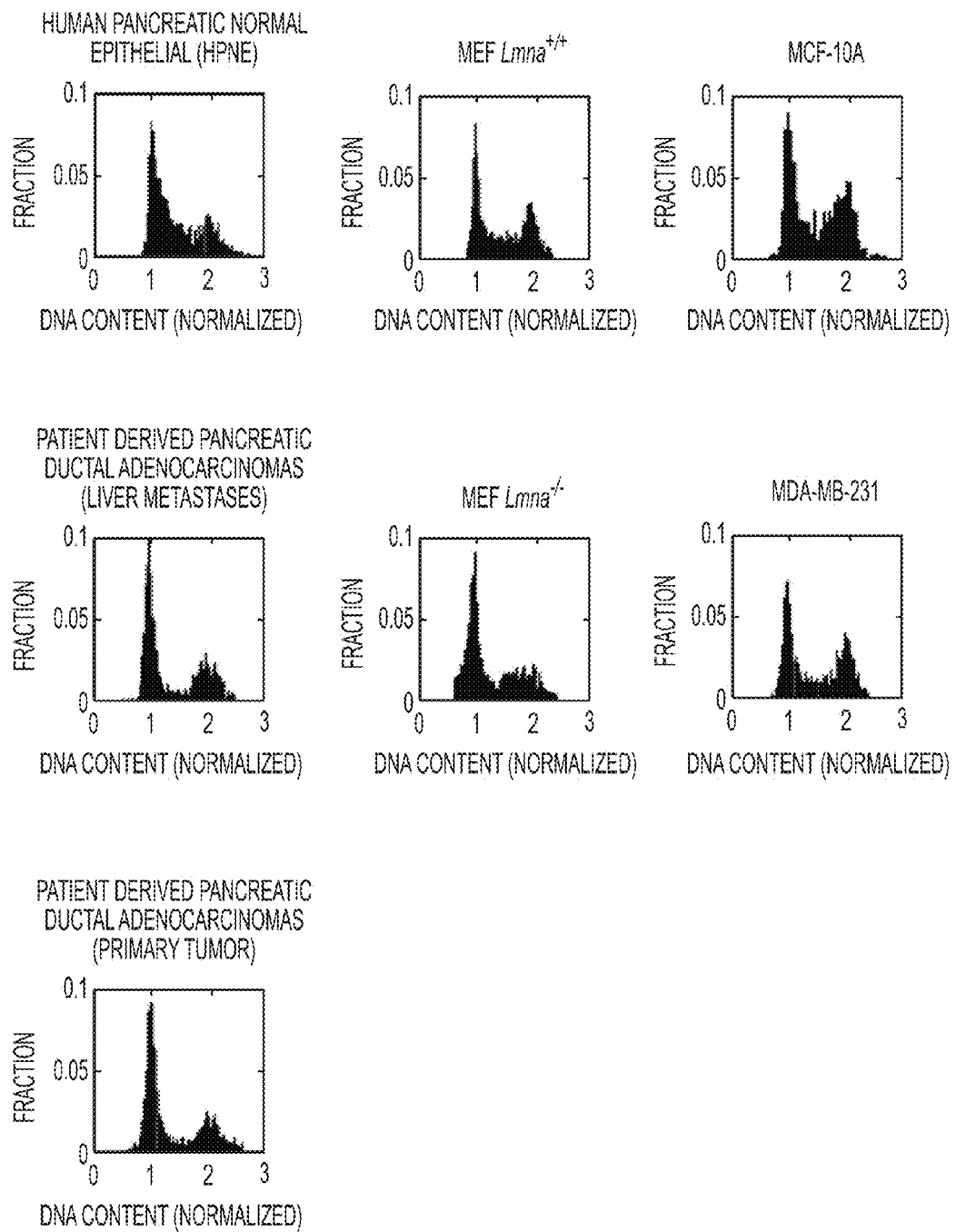
FIG. 28 illustrates cell cycle analysis applied to a wide range of cell types according to an embodiment of the current invention.

FIG. 28 illustrates cell cycle analysis applied to a wide range of cell types according to an embodiment of the current invention. The assay was not limited to c2c12 and MD-MB-231 cells. We tested seven additional types of cells and found that our assay could readily measure their cell-cycle distributions. To demonstrate the versatility of our method, seven additional types of cells were analyzed. These cells include human pancreatic normal epithelial cells (HPNE), human breast normal epithelial cells (MCF10A), patient-derived pancreatic cancer ductal adenocarcinoma cells that metastasized to the liver, LMNA$^{+/+}$ mouse embryonic fibroblasts (MEFs), LMNA$^{-/-}$ MEFs, metastatic breast cancer cells (MD-MB-231), and patient-derived pancreatic cancer ductal adenocarcinoma cells from the primary tumor. At least 1,000 cells were analyzed for each cell line.

These cells were chosen to determine whether our assay worked on both normal and diseases cells, immortalized and primary cells, as well as human and rodent cells. The tested cells include human pancreatic normal epithelial cells, patient-derived pancreatic cancer ductal adenocarcinoma cells harvested from the primary tumor and from liver metastatic sites, normal human breast epithelial cells (MCF10A), and primary mouse embryonic fibroblast).

Cell Properties Depend Critically on Cell Cycle Phase

Next, we used the same microscopy method to measure both cell-cycle phase and cell and nuclear properties simultaneously in the same cells. To help clarify the potential influence of cell cycle-phase distribution on cell properties (such as nuclear size or cell shape), ENREF 24 [Assoian, R. K. Anchorage-dependent Cell Cycle Progression. *The Journal of Cell Biology* 136, 1-4 (1997)] we wrote the mean value of a given cell property <x> as a linear combination of cell fractions in each phase and mean values of the cell property in each of the cell cycle phase:

$$\langle x \rangle = f_{G_0/G_1} x_{G_0/G_1} + f_S x_S + f_{G_2/M} x_{G_2/M} = \sum_{i=G_0/G_1}^{G_2/M} f_i x_i \quad \text{Eq 1}$$

Here, <x> is the cell population-averaged value of the cell property being considered (e.g. the cell population-averaged values of nuclear and cell sizes and shapes), $x_i$ are the mean values of this property in the cell-cycle phases i (i=$G_0/G_1$, S, and $G_2/M$ phases), which might be different in each phase i, and $f_i$ are the fractions of cells in each phase i, which is also the relative time cells spend in each phase of the cell cycle. The method presented here enables us to measure $x_i$ and $f_i$ simultaneously in the same cells. When assessing the role of the expression or activity of a protein in a given cell function, cells are typically subjected to a drug that specifically inhibits/activates the protein or the gene of interest is knocked down (KD), knocked out (KO) or over-expressed. It is then pervasively assumed than any measured change in mean cell property (i.e. a change in the population averaged value <x>) reflects the involvement of this protein in the cell function being assessed, without considering the possible redistribution of the cells along the cell cycle.

For example, the nuclear lamina-associated structural proteins Nesprins are widely believed to be structural regulators of nuclear shape because of their role of physically connecting the nuclear lamina to the cytoskeleton and because the depletion of Nesprins changes nuclear roundness [Stewart-Hutchinson, P. J., Hale, C. M., Wirtz, D. & Hodzic, D. Structural requirements for the assembly of LNC complexes and their function in cellular mechanical stiffness. *Experimental Cell Research* 314, 1892-1905 (2008); Khatau, S. B. et al. A perinuclear actin cap regulates nuclear shape. *Proceedings of the National Academy of Sciences* 106, 19017-19022 (2009)]. This approach to assess the role of a protein in cell functions is only legitimate if the fractions $f_i$ of cells in the different cell-cycle phases remain unchanged following application of the inhibitor/activator or genetic manipulation, i.e. that the protein of interest is not also a cell cycle regulator. Alternatively, when in doubt that it is actually correct and that cell properties could be cell-cycle dependent, then cells can be synchronized. To synchronize cells, cells are often subjected to serum-starvation or chemicals that arrest cells in a specific phase of the cell cycle [Harper, J. V. in, Vol. 296 157-1662004); Tobey, R. A., Valdez, J. G. & Crissman, H. A. Synchronization of human diploid fibroblasts at multiple stages of the cell cycle. *Experimental Cell Research* 179, 400-416 (1988); Kues, W. A. et al. Cell Cycle Synchronization of Porcine Fetal Fibroblasts Effects of Serum Deprivation and Reversible Cell Cycle Inhibitors. *Biology of Reproduction* 62, 412-419 (2000); Ballabeni, A. et al. Cell cycle adaptations of embryonic stem cells. *Proceedings of the National Academy of Sciences* (2011)]. For instance, thymidine arrests cells in the early S phase. However, thymidine treatment to synchronize cells and assess cell phenotypes in the S phase is only correct if the cell properties, $x_i$, are the same for S-phase-synchronized cells as the cell properties of non-synchronized cells that are happen to be in the S phase.

The same assumption is typically made when cell synchronization is induced by serum starvation or cell treatment with the microtubule depolymerizing drug nocodazole, which enrich the $G_0/G_1$ phase and M phase, respectively.

Figure 29:
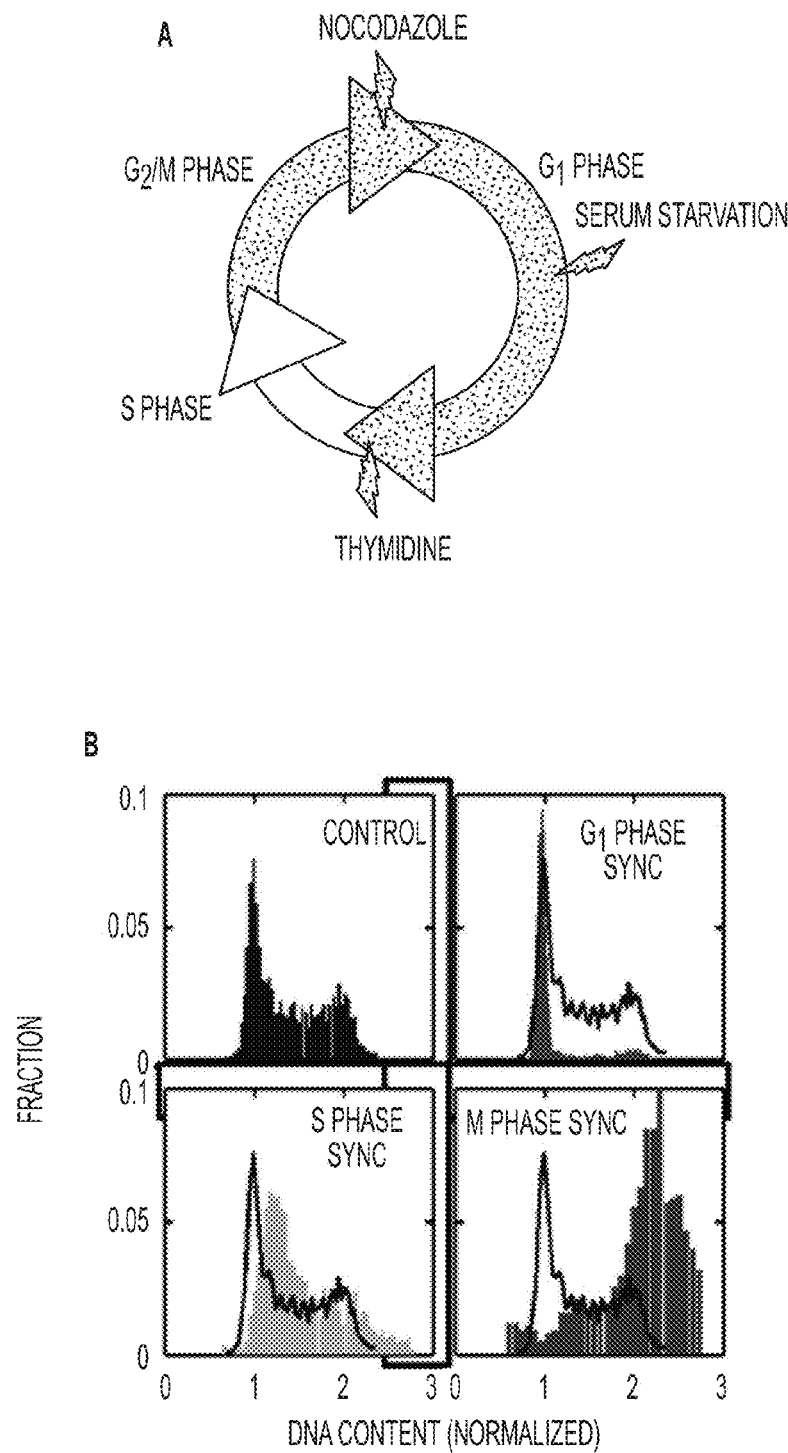
FIGS. 29 and 30 illustrate how conventional cell cycle synchronization methods affect cell/nuclear properties according to an embodiment of the current invention.
Figure 30:
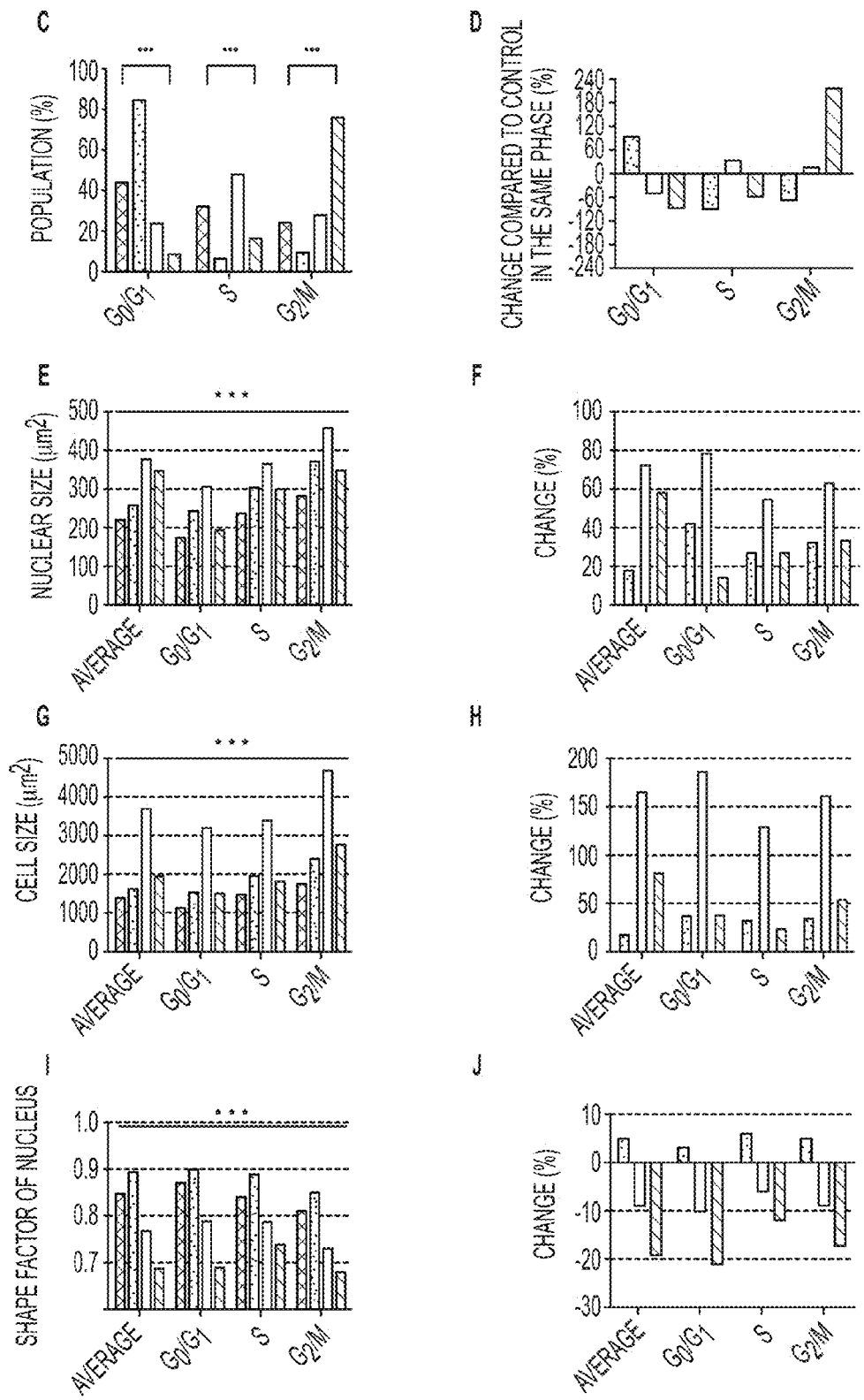

FIGS. 29 and 30 illustrate how conventional cell cycle synchronization methods affect cell/nuclear properties according to an embodiment of the current invention. (A) Ubiquitously used methods were applied to synchronize the phase of c2c12 cells. These include serum-starvation which enriches cells in the $G_1$ phase, nocodazole treatment which enriches cells in the M phase, and thymidine treatment which enriches cells in the early S phase. (B) Cell-cycle phase distributions obtained by microscopy-based analysis of untreated control asynchronized cells (bars), and serum-starved cells, thymidine-treated cells, and nocodazole-treated cells. The contour of the cell-cycle distribution for control cells is shown in each case to help visual comparison. (C and D). Proportion of cells in the $G_0/G_1$, S, and $G_2/M$ phases for control, serum-starved, thymidine-treated, and nocodazole-treated cells (C) and percentages changes caused by these different synchronization methods compared to control cells (D). (E-J). Population-averaged values and cell-cycle-phase-dependent mean values of nuclear size (E), cell size (G), and nuclear shape (I) and corresponding percentages changes (F, H, and J), compared phase-to-phase, induced in serum-starved, thymidine-treated, and nocodazole-treated cells in each phase compared to control cells. All apparent differences are statistically significant, P<0.001 (ANOVA) as compared to phenotypic values for control cells in each corresponding phase. For (B-L), three biological repeats conducted on different cells were analyzed for a total of >3,000 cells for each tested condition.

Exploiting the advantage that our assay can measure cycle phase and cell properties in the same individual cells simultaneously, we tested whether these commonly used cell synchronization methods verified this assumption. Surprisingly, synchronization methods, such as serum starvation and thymidine/nocodazole treatments, affected not only cell cycle distributions, as expected, but also greatly changed cell and nuclear properties (A-D). Results from our analysis confirmed that, as expected, these methods of synchronization did enrich cells in the target cycle phase: the S phase for thymidine treatment, the G1 phase following serum starvation, and the M phase for nocodazole treatment (B and C). However, these synchronization methods also had a significant and lasting effect on cell properties in every cell cycle phase (E-J). For instance, thymidine treatment greatly increased the size of cells in the enriched S phase by 120% compared to untreated cells in the same S phase, i.e. the mean size of treated cells in the S phase was 2.2 times the mean size of untreated cells in the S phase. The mean size of thymidine-treated cells in the enriched $G_0/G_1$ and $G_2/M$ phases were similarly increased by 130% and 220% compared to untreated (asynchronized) cells in the same $G_0/G_1$ and $G_2/M$ phases, respectively. Serum starvation and nocodazole treatment fared somewhat better, but still changed measured cell properties by >30%, including a 75% increase in cell size for nocodazole-treated cells in the $G_2/M$ phase. If synchronization were non-invasive, these phenotypic changes should have been vanishingly small.

Figure 31:
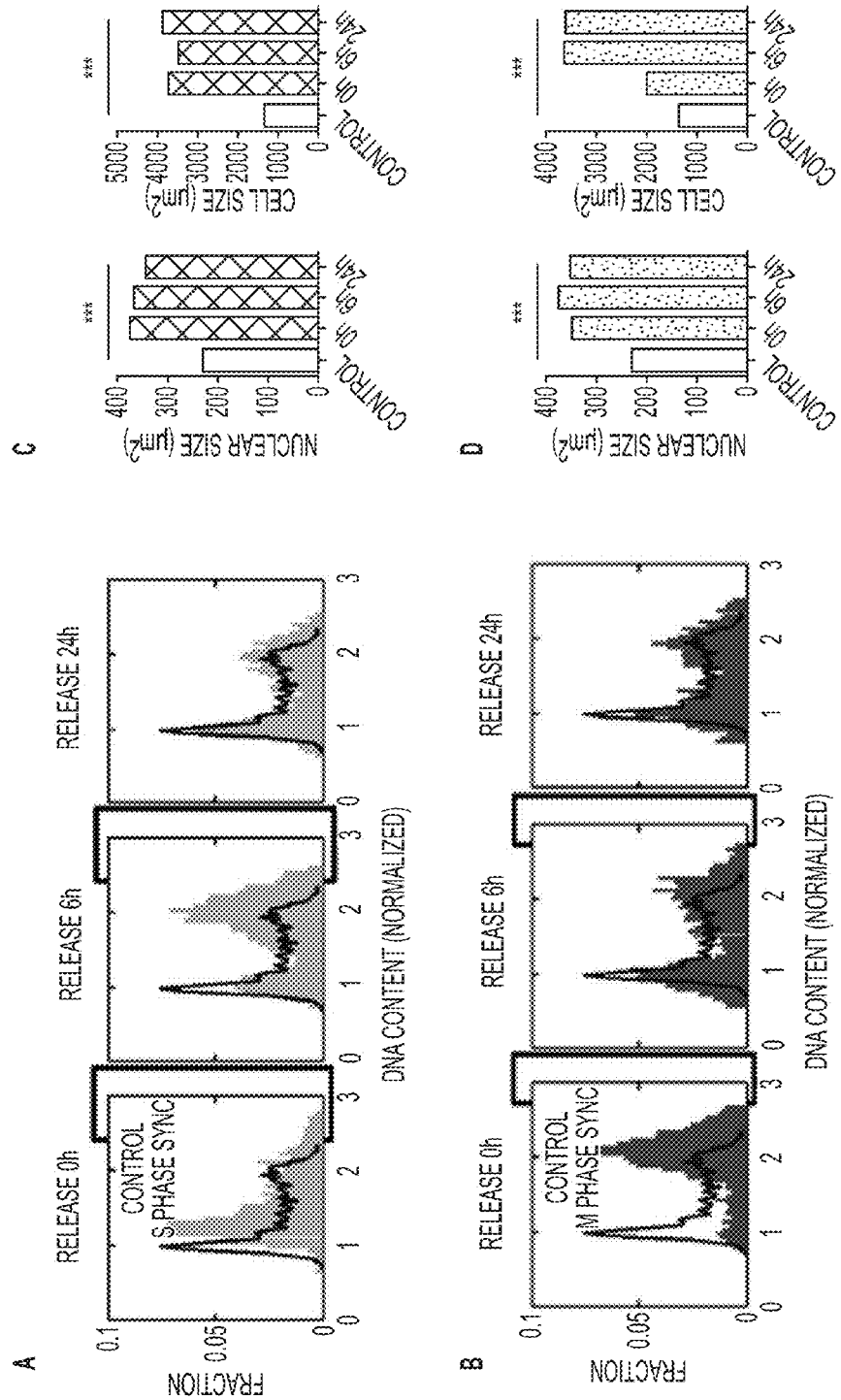
FIGS. 31 and 32 illustrate how alteration of cell cycle causes long term effects on cell properties according to an embodiment of the current invention.
Figure 32:
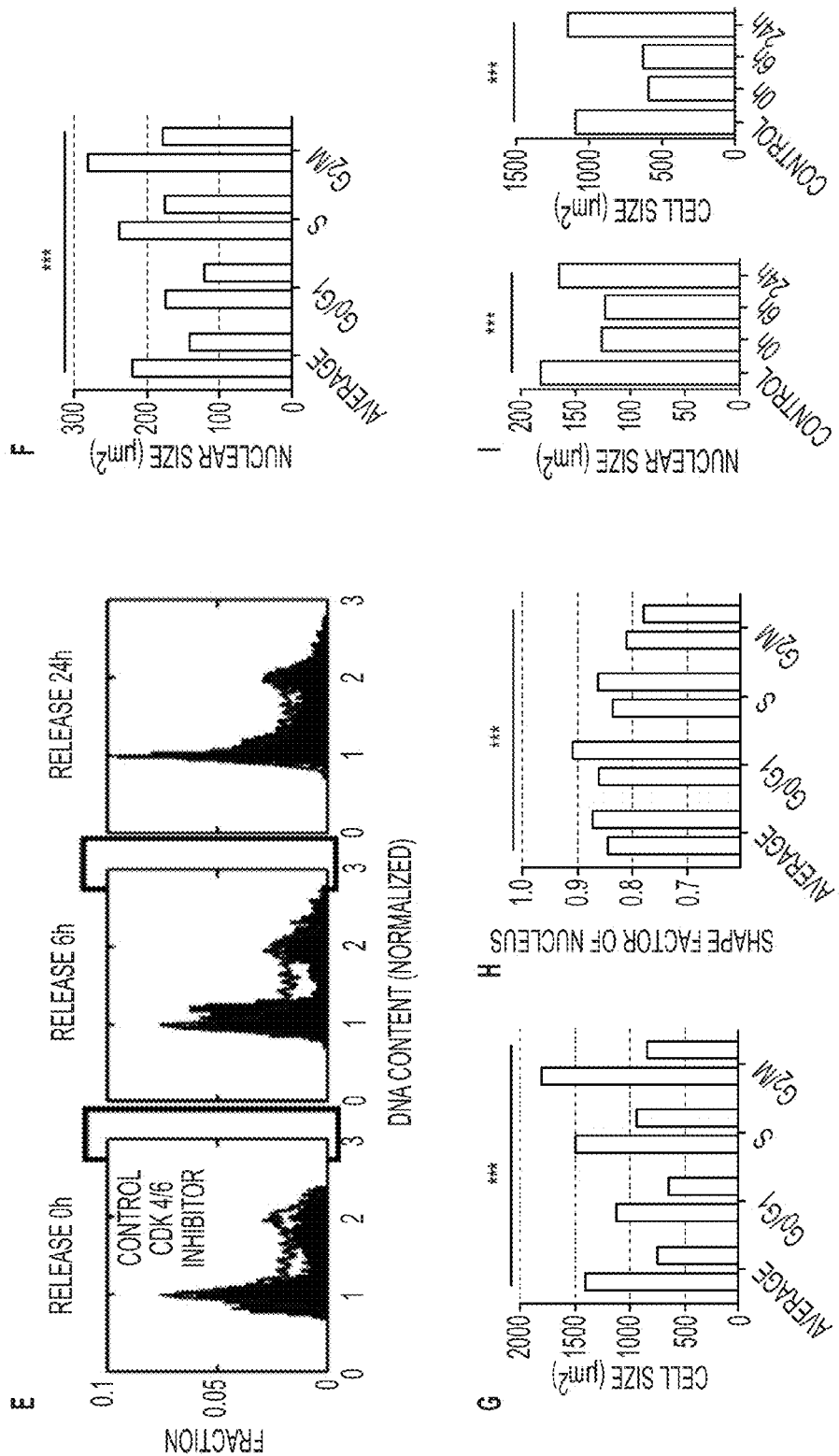

FIGS. 31 and 32 illustrate how alteration of cell cycle causes long term effects on cell properties according to an embodiment of the current invention. (A and B). Asynchronized cell cycle distribution is recovered after 24 h release of from synchronizing drug, thymidine treatment (A) and nocodazole treatment (B). (C and D). Mean changes in nuclear size and cell size induced 0 h, 6 h, and 24 h after release of thymidine (C) and nocodazole (D) compared to control cells. ***: P<0.001 (ANOVA). (E). Cell-cycle distributions of control cells and cells treated with Cdk4/6 inhibitor IV. Control and Cdk4/6 inhibitor treatment are shown. (F-H). Population-averaged (first bars) and cell-cycle-dependent nuclear size (F), cell size (G), and nuclear shape factor (H). I. Mean changes in nuclear size and cell size induced 0 h, 6 h, and 24 h after removing cdk4/6 inhibitor IV. Three biological repeats on different cells were analyzed for a total of >3,000 cells for each tested condition.

Importantly, we verified that adding back serum to serum-starved cells or washing cells to eliminate the synchronizing drug from the medium allowed cells to recover the cycle-phase distribution of untreated cells prior to forced synchronization within 24 h (A and B). However, changes in cell and nuclear properties did not recover their untreated values, i.e. all tested synchronization methods continued to affect cell/nuclear size and cell/nuclear shape, even 24 h after release (C and D). Together these results indicate that commonly used synchronization methods are highly invasive, as they do not keep cell properties constant in the enriched phase. One should use synchronization methods with caution, and should not ignore the effect of changes in phenotypic property associated with forced synchronization.

Next, we asked whether inhibition of well-characterized cell cycle regulators, such as Cdk4/6, could also inadvertently affect cellular phenotypes. Eq. 1 suggests that a change in the cell-population-averaged value of the cell phenotype <x> (say nuclear size) following protein inhibition could result from cell-cycle redistribution (i.e. changes in $f_i$). As expected, treatment of cells with specific Cdk4/6 inhibitor IV, trans-4-((6-(ethylamino)-2-((1-(phenylmethyl)-1H-indol-5-yl) amino)-4-pyrimidinyl)amino)-cyclohexanol (CINK4) blocked cells in the $G_0/G_1$ phase and reduced the population of cells in the S and $G_2/M$ phase (3E) [Soni, R. et al. Selective In Vivo and In Vitro Effects of a Small Molecule Inhibitor of Cyclin-Dependent Kinase 4. *Journal of the National Cancer Institute* 93, 436-446 (2001)]. Moreover, Cdk4/6 inhibition also significantly affected population-averaged nuclear and cell morphology (e.g. ~50% decrease in cell size in nuclear size accompanied by rounding of the nucleus) (F-H), and continued to affect cell properties up to 6 h after release (I). However, our assay which can evaluate cell-cycle-dependent values of phenotypes simultaneously (i.e. changes in x) revealed that inhibition of Cdk4/6 caused significant effects on the values of phenotypes in each phase. For instance, following Cdk4/6 inhibition, the nuclear size of cells in the $G_0/G_1$ phase decreased by >50% (P<0.0001). Hence our assay suggests that besides its well-known central role in cell cycle, Cdk4/6 may also play a structural role by regulating nuclear morphology. The role of structural proteins in cell cycle regulation Having manipulated cell cycle distributions through various forced synchronization schemes or Cdk4/6 inhibition to determine their (unexpected) effect on cellular and nuclear properties in each phase, we next manipulated cell properties through shRNA-mediated depletion of seemingly well-established structural regulators of these properties, while simultaneously measuring potential changes in cell cycle distribution. To help clarify this test, we return to Eq. 1. For a protein to be a bona fide, intrinsic regulator of nuclear size or other cell properties and not an indirect regulator by being a regulator of cell cycle (which in turn would affect cell properties, FIG. 26, A), the depletion of that protein should mostly induce changes in cell properties $x_i$, not changes in cell cycle fractions $f_i$.

Figure 33:
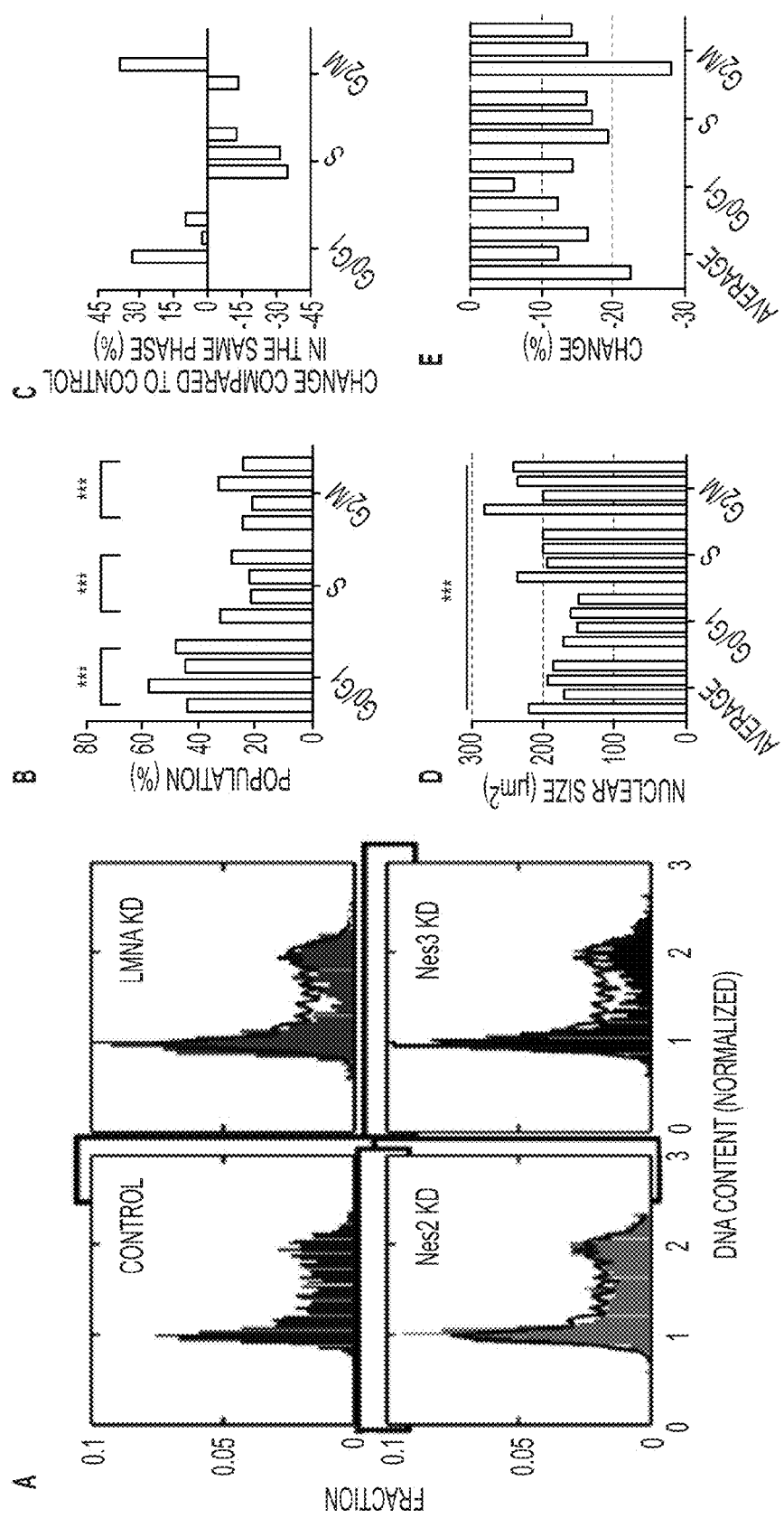
FIGS. 33 and 34 illustrate how combined measurements of cell cycle phase and cell properties reveal bona fide regulators of cell phenotypes and cycle phase according to an embodiment of the current invention.
Figure 34:
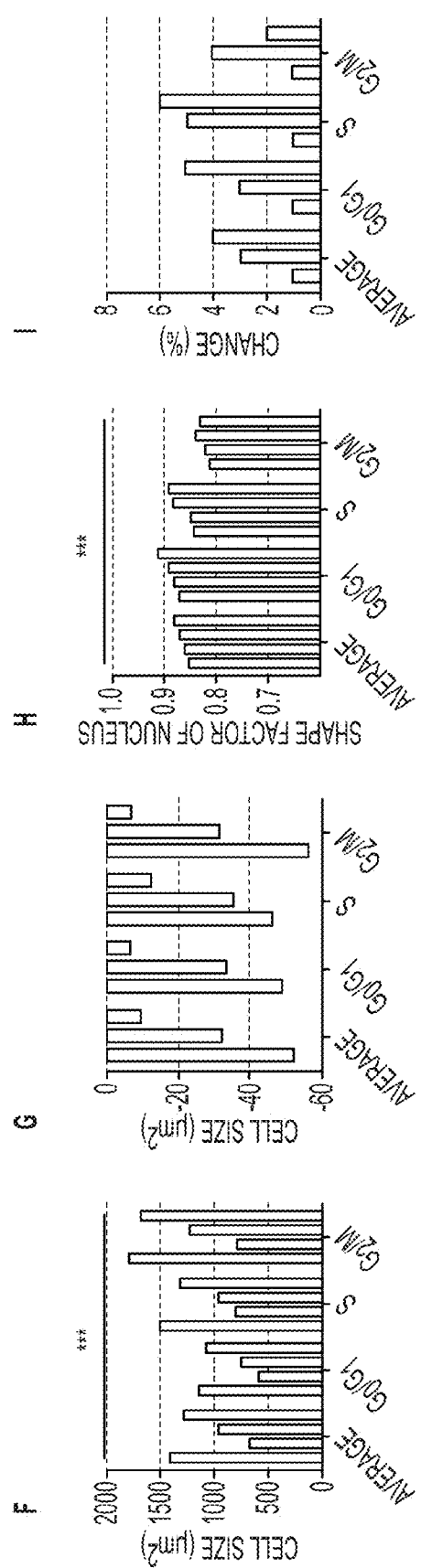

FIGS. 33 and 34 illustrate how combined measurements of cell cycle phase and cell properties reveal bona fide regulators of cell phenotypes and cycle phase according to an embodiment of the current invention. (A) Cell cycle distributions obtained by microscopy-based analysis of control cells and cells depleted of nuclear envelope-associated proteins Lamin A/C, Nesprin3, or Nesprin2giant. The profile of the cell cycle distribution for control cells is shown for visual comparison. (B and C) Proportions of cells in the $G_0/G_1$, S, and $G_2/M$ phases for control (bars), Lamin A/C-depleted cells, Nesprin3-depleted cells, and Nesprin2giant-depleted cells (B) and percentages changes caused by protein depletion compared to control cells (C). (D-I) Cell-cycle-phase-dependent mean values of nuclear size (D), cell size (F), and nuclear shape (H) and corresponding percentages changes (E, G, and I), compared phase to phase, induced in each phase by depletion of Lamin A/C, depletion of Nesprin3, and depletion of Nesprin2giant compared to control cells. All apparent differences are statistically significant, P<0.001 (ANOVA) as compared to phenotypic values for control cells in each corresponding phase. Three biological replicates were analyzed for all tested conditions (A-I).

Nuclear lamina protein Lamin A/C, which forms a thin elastic filamentous meshwork underneath the nuclear envelope and penetrates the intranuclear space, and LNC complex molecules Nesprin2giant and Nesprin3, which physically connect the nuclear lamina to the cytoskeleton, have recently been established as major structural proteins that regulate nuclear size and nuclear shape [Hale, C. M. et al. Dysfunctional Connections Between the Nucleus and the Actin and Microtubule Networks in Laminopathic Models. *Biophysical Journal* 95, 5462-5475 (2008)]. Indeed, we found that shRNA-mediated depletion of Lamin A/C, Nesprin2giant and Nesprin3 all significantly deformed and decreased the size of the nucleus and cell in all phases of the cell cycle ("average bars" in FIGS. 33 and 34, D-I).

However, the depletion of these nuclear envelope proteins also affected cycle-phase distribution (FIGS. 33, A-C) [Johnson, B. R. et al. A-type lamins regulate retinoblastoma protein function by promoting subnuclear localization and preventing proteasomal degradation. *Proceedings of the National Academy of Sciences of the United States of America* 101, 9677-9682 (2004); Dorner, D. et al. Lamina-associated polypeptide 2α regulates cell cycle progression and differentiation via the retinoblastoma—E2F pathway. *The Journal of Cell Biology* 173, 83-93 (2006); Salpingidou, G., Smertenko, A., Hausmanowa-Petrucewicz, I., Hussey, P. J. & Hutchison, C. J. A novel role for the nuclear membrane protein emerin in association of the centrosome to the outer nuclear membrane. *The Journal of Cell Biology* 178, 897-904 (2007)]. For instance, shRNA-mediated depletion of Lamin A/C enriched the $G_0/G_1$ phase, while reducing the fractions of cells in the S and $G_2/M$ phases (FIG. 33, C). This result was confirmed in primary LMNA$^{+/+}$ and LMNA$^{-/-}$ mouse embryonic fibroblasts.

Figure 35:
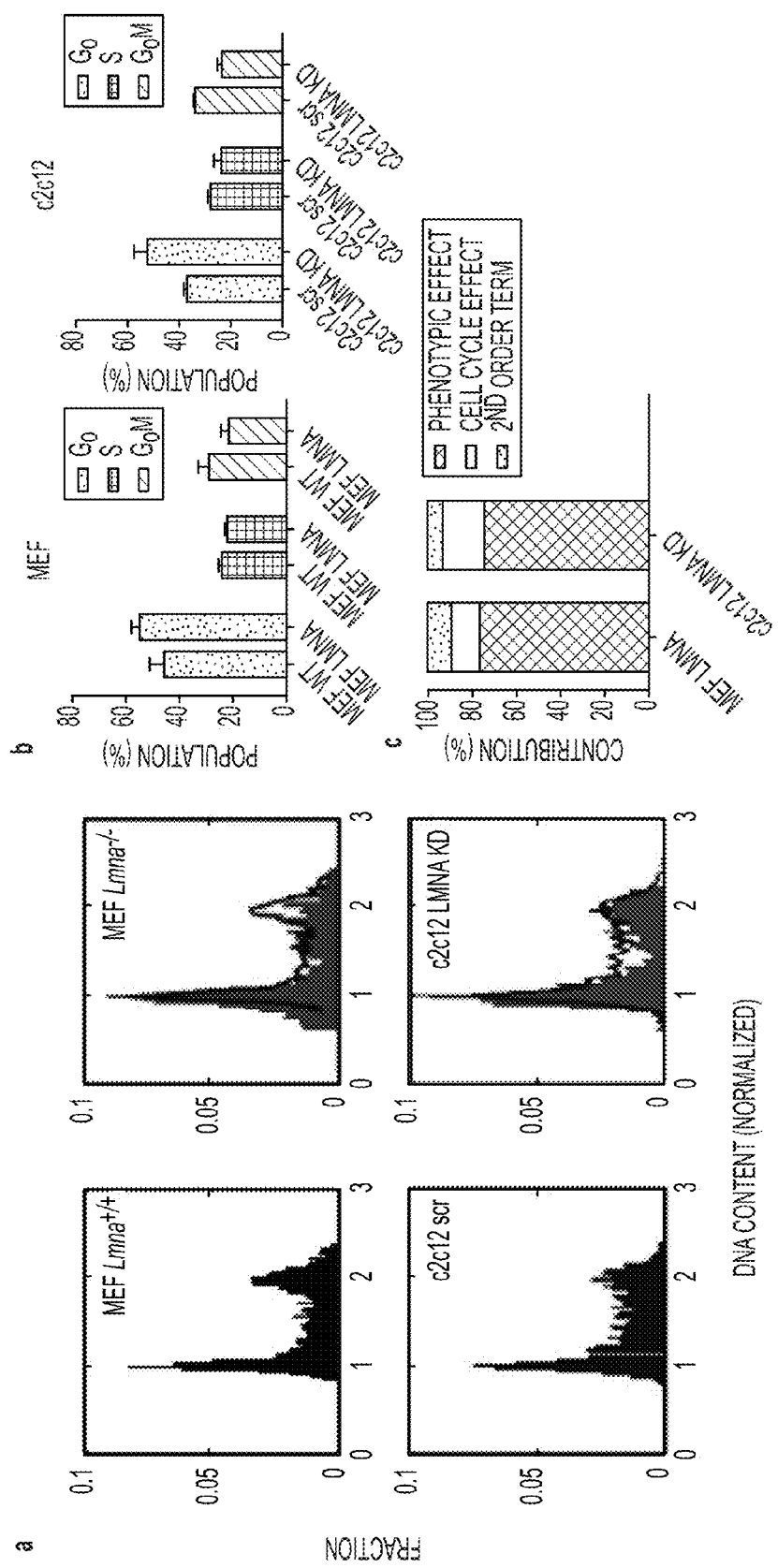
FIG. 35 illustrates how lamin deficiency enriches cells in the G0/G1 phase according to an embodiment of the current invention.

FIG. 35 illustrates how lamin deficiency enriches cells in the G0/G1 phase according to an embodiment of the current invention. (A). Cell cycle distributions of LMNA$^{-/-}$ MEFs and Lamin A/C KD c2c12 cells compared to LMNA$^{+/+}$ MEFs and control c2c12 cells transfected with a scrambled construct, respectively, obtained by the microscopy assay. (B). Quantitative analysis demonstrates significant (P<0.001) increase in the $G_0/G_1$ fractions and decrease in the $G_2/M$ fractions of both LMNA$^{-/-}$ MEFs and Lamin A/C KD c2c12 cells compared to control cells. (C). Relative contributions to population-averaged changes in nuclear size of LMNA$^{-/-}$ MEFs and Lamin A/C KD c2c12 cells show only ~75% contribution from direct intrinsic nuclear size changes. The rest of ~25% is contributed from re-distribution of cell cycle and the second order term. At least 1,000 cells were analyzed in three biological repeats (different cells are analyzed each time) for a total of >3,000 cells for each cell line.

Lamin A/C deficiency enriched the $G_0/G_1$ phase, while reducing the number of cells in other phases. Depletion of Nesprin3 also significantly enriched the $G_0/G_1$ phase and slightly, by significantly, reduced the fractions of cells in the S and $G_2/M$ phases. Nesprin 3 depletion had a much larger effect on cell cycle redistribution than Nesprin2giant (FIG. 33, B). Our assay allowed us to assess changes in nuclear size, phase by phase (for example, by comparing the mean values of nuclear size in the $G_2/M$ phase of both control cells and shRNA-depleted cells directly) (FIGS. 33 and 34, D-I). Furthermore, the assay revealed that the role of Lamin A/C and Nesprins in nuclear morphology and cell size strongly depended on cell-cycle phase (FIGS. 33 and 34, D-I). For instance, depletion of Lamin A/C and Nesprins had a 3-fold more significant effect on nuclear size for cells in the $G_0/G_1$ phase that cells in the $G_2/M$ phase (FIG. 33, E). Together these results showed that while Lamin A/C, Nesprin2giant and Nesprin3 could not be classified as intrinsic regulators of nuclear and cell size, as they were also regulators of cell cycle phase distribution, which indirectly affected cell and nuclear morphology.

Figure 36:
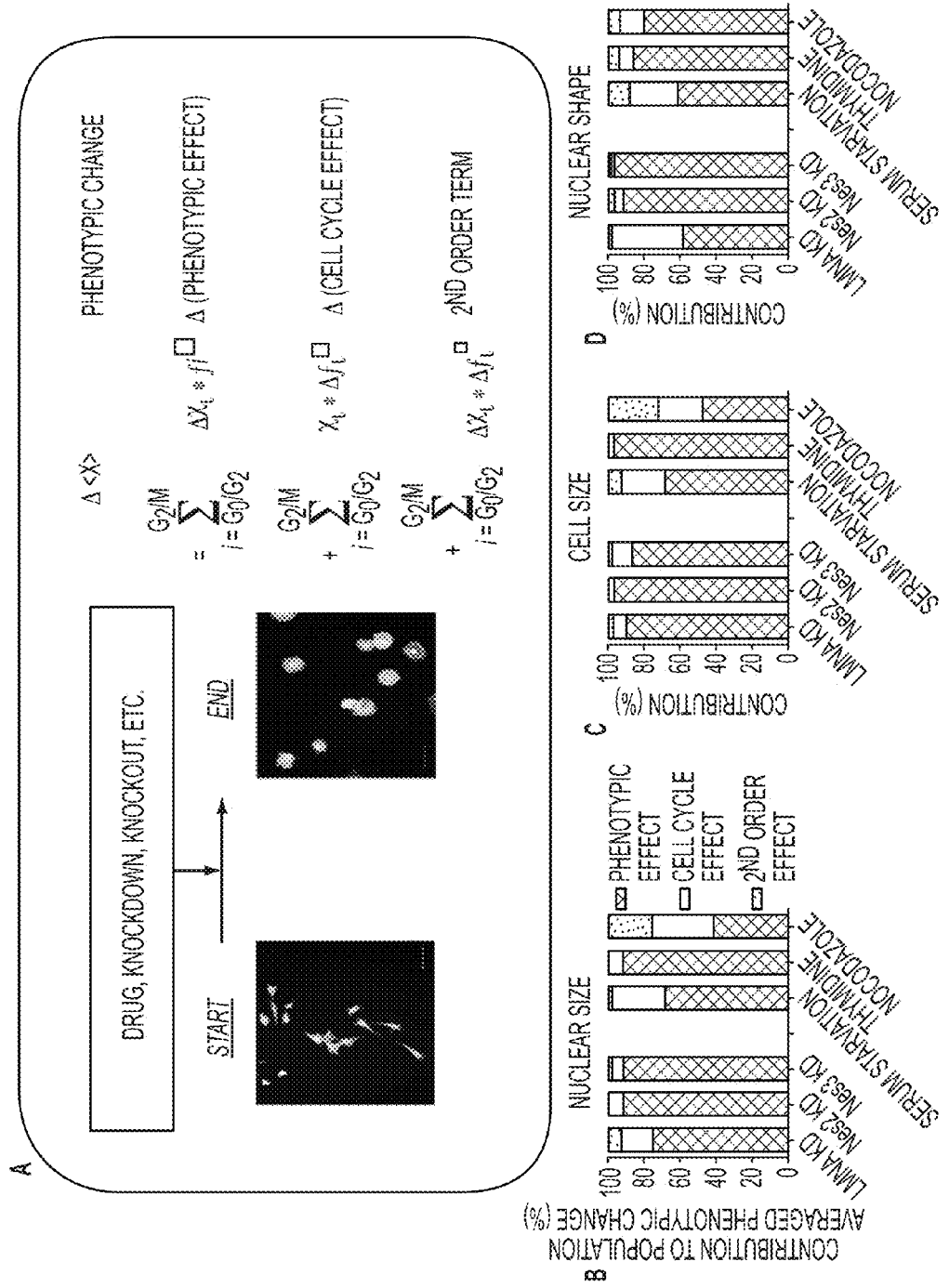
FIG. 36 illustrates contribution of cell cycle redistribution to population-averaged changes in cell properties according to an embodiment of the current invention.

Distinct contributions to global changes in cell properties from cell-cycle redistribution vs. intrinsic changes in cell properties FIG. 36 illustrates contribution of cell cycle redistribution to population-averaged changes in cell properties according to an embodiment of the current invention. (A). Changes in the population-averaged values of cell/nuclear properties can be expressed as a sum of three major contributions:

$$\Delta x = \langle x \rangle_{control} - \langle x \rangle_{KDorDrug} = \sum_{i=G_0/G_1}^{G_2/M} \Delta x_i f_i \bigg|_{control} + \sum_i \Delta f_i x_i \bigg|_{control} + \sum_i \Delta f_i \Delta x_i.$$

Here $\Delta x$ is the total change in the population-averaged value of the cell/nucleus property of interest caused by the depletion (denoted by lowercase KD) of either Nesprin2giant, Nesprin3, or Lamin A/C or induced by forced synchronization (lowercase Drug) compared to control cells; $\Delta x_i$ are the same differences but evaluated for cells in each cell-cycle phase i; and $\Delta f_i$ are the changes in cell-cycle fractions for each phase i. The summation Overall changes in cell properties, $\Delta x$, may stem from three distinct contributions: changes in intrinsic cell properties independent of changes in cell cycle (first term), indirect changes in cell properties due to a change in cell cycle distribution (second term), and coupled changes in cell cycle and cell properties (third term), which are expected to be second-order in magnitude.

B-D. Contributions to global changes in population-averaged nuclear size (B), cell size (C) and nuclear shape (D) due to intrinsic cell-cycle-independent changes in these properties (black), due to cell cycle redistribution (white), and due to coupled effects of cell cycle redistribution and intrinsic cell-cycle-independent changes in nuclear size (grey). This analysis was applied to c2c12 cells depleted of Lamin A/C, cells depleted of Nesprin2giant, and cells depleted of Nesprin3, as well as c2c12 cells subjected to serum—starvation, cells treated with thymidine, and cells treated with nocodazole. Three biological replicates were analyzed for all tested conditions (B-D).

When cells are subjected to nocodazole or thymidine treatments, serum starvation, or shRNA-depletion of structural proteins such as Lamin A/C and Nesprins, the population-averaged mean values of nuclear size, cell size, and nuclear shape change. We can quantify the contributions to changes in these mean values due to: (i) direct changes in intrinsic values of these properties ("phenotypic effect", FIG. 36, A), i.e. changes in the cell-cycle-independent values of these properties, (ii) indirect changes due to cell cycle re-distribution ("cell cycle effect", FIG. 36, A), and (iii) second-order effects due to coupled phenotypic changes and cell cycle distribution ("$2^{nd}$ order term", FIG. 36, A). Indeed, one can easily show that the global change in a cell property x can be written as:

$$\Delta x = \langle x \rangle_{control} - \langle x \rangle_{KDorDrug} = \sum_{i=G_0/G_1}^{G_2/M} \Delta x_i f_i \bigg|_{control} + \sum_i \Delta f_i x_i \bigg|_{control} + \sum_i \Delta f_i \Delta x_i. \quad \text{Eq 2}$$

Here $\Delta x$ is the total change in the mean value of nuclear size, cell size, and nuclear shape caused by shRNA-mediated depletion (subscript KD) of Nesprin2giant, Nesprin3, or LaminA/C or by pharmacological synchronization or protein inhibition (subscript Drug) compared to control cells; $\Delta x_i$ are the same differences but evaluated for cells in each cell-cycle phase i; and $\Delta f_i$ are the changes in cell-cycle fractions for each phase i. Therefore, overall changes in cell properties following protein depletion or drug treatment may stem from three distinct contributions: (i) intrinsic changes in cell properties independent of changes in cell cycle-phase distribution (first term in Eq 2), indirect changes in cell properties due a cell cycle-phase redistribution (second term), and coupled changes in cell cycle and cell properties (third term), which are expected to be second-order in magnitude (FIG. 36). For cells depleted of structural proteins such as nuclear-envelope-associated Nesprins, changes in cell properties should only be due to the first term, which means that $\Delta f_i \approx 0$ in Eq. 2 and, in turn, $\Delta x \approx \Sigma \Delta x_i f_{icontrol}$. For cells subjected to synchronization by serum-starvation or drug treatment, changes in cell properties should only be due to the second term (i.e. due to cell-cycle redistribution), which means that $\Delta x_i \approx 0$ in Eq. 2 and $\Delta x \approx \Sigma \Delta f_i x_{icontrol}$. Here $f_{icontrol}$ and $x_{icontrol}$ are the fractions of cells and values of the cell property of interest in phases i for control cells.

Ideally, if Lamin A/C, Nesprin2giant, and Nesprin3 were true bona fide (or intrinsic) structural proteins regulating nuclear shape and size without changing phase distributions, then the contribution from the first term to population-averaged changes in nuclear shape and size would be zero and the contribution from the second term would be 100% of <x>. Here, we found that overall changes in nuclear size upon depletion of Lamin A/C due to direct intrinsic changes in nucleus size (when properly compared phase-to-phase) was only 75%, and that the contribution due to cell-cycle redistribution was significant (>20%) (FIG. 36, B). Depletion of Nesprin2giant and Nesprin3 still induced 9% contribution to global change in nuclear size from cell cycle re-distribution (FIG. 36, B). Similar conclusions held for changes in cell size (FIG. 36, C) and nuclear shape (FIG. 36, D): changes in cell size and nuclear shape by depletion of Lamin A/C, Nesprin3, or Nesprin2giant were partly due to non-negligible contributions from cell cycle re-distribution.

Vice versa, we analyzed the contributions of (unwelcome) changes in cell/nuclear properties following forced synchronization by serum starvation, thymidine treatment, or nocodazole treatment (FIG. 36, B-D). Ideally, if synchronization were non-invasive, then the contribution from the first term in Eq. 2 to changes in nuclear shape and size would be 100% and the contribution from the other terms would be zero. Remarkably, we found that the contributions to changes in nuclear size due to forced cell-cycle redistribution was significantly smaller than the contributions from intrinsic changes in nuclear size: only 31% for serum starvation, 9% for thymidine treatment, and 35% for nocodazole treatment were due to changes in nuclear size induced by forced synchronization compared to contributions of 68%, 91%, and 41% that were due to (uncontrolled) changes in nuclear size in each phase (FIG. 36 B). Similar conclusions held when assessing changes in nuclear size and nuclear shape (FIG. 36, C and D).

A literature survey indicates that the vast majority of biological studies that make use of shRNA-induced depletion or genetic knockout or over-expression of specific proteins as methods to assess the function of a protein in mammalian cells only use changes in population-averaged values of the cell property under study (the left hand-side of Eq. 2) as a way to quantitatively assess a protein function in cell physiology, without taking into account possible changes in phase distribution caused by these cell manipulations. The remainder of these studies used forced synchronization as a way to reduce cell-cycle-dependent effects, and none measured both changes in cell properties and cell cycle distribution at the same time, as presented in this study. Our results suggest that this general approach to assess the role of proteins in establishing cell and nuclear properties could lead to erroneous conclusions.

Here, we used a microscopy-based assay that allowed us to measure cell cycle phase and cell/nuclear properties simultaneously in the same cells. This assay: (i) distinguished bona fide cell-cycle-independent regulators of cell and nuclear properties from cell-cycle-dependent regulators that regulate cell properties only or partially though cell cycle redistribution, (ii) revealed new regulators of cell cycle distribution (e.g. Nesprin2giant and Nesprin3 were not known to be cell cycle regulators), and (iii) quantified the distinct contributions of specific proteins to cell properties due to direct/intrinsic regulation by these proteins and due to indirect changes caused by uncontrolled cell cycle redistribution.

This study illuminates the critical importance of measuring cell and nuclear properties in each cell phase, highlights and quantifies the danger of using commonly used synchronization methods to eliminate potential effects of cell cycle redistribution on cell phenotypes, and suggests that regulators of other cell functions (e.g. nuclear morphology, cell motility), previously identified through shRNA-mediated depletion or knockout studies, may indeed be mixed cell-property/cell-cycle regulators.

Methods

Cell Culture, Cell Synchronization, and Pharmacological Treatments

Mouse myoblasts (c2c12) were cultured in Dulbecco's Modification of Eagle's Medium (DMEM) (Invitrogen, Carlsbad, Calif.) supplemented with 10% of fetal bovine serum (FBS, Hyclone, Logan, Utah) and 100 U penicillin and 100 µg streptomycin (Sigma, St. Louis, Mo.) and 0.1% of puromcyin. Human breast cancer cells, MDA-MB-231 (ATCC, Manassas, Va.), and freshly harvested $LMNA^{+/+}$ and LMNA$^{-/-}$ mouse embryonic fibroblasts were cultured in DMEM with 10% of FBS and 100 U penicillin and 100 µg streptomycin. Human transformed epithelial cells, MCF-10A, were cultured in DMEM F-12 medium (Invitrogen) with 5% of horse serum, 0.5 µg/ml of hydrocortisone, 20 ng/ml of hEGF, 10 µg/ml of bovine insulin (Sigma), and 100 µg/ml cholera toxin (Sigma). Human pancreatic normal epithelial cells (HPNE) were cultured in DMEM (low glucose), M3 base medium, FBS, Gentamicin, EGF, P/S (Sigma). Patient-derived pancreatic ductal adenocarcinomas, liver metastasis and primary tumor cells were cultured in DMEM with 10% of FBS and 100 U penicillin and 100 µg streptomycin. The culture environment was maintained at 37° C. and 5% $CO_2$. Cells were passaged every three days.

For each type of cell, ~10,000 cells were plated on a glass bottom dish (World Precision Instruments, Sarasota, Fla.). After incubation for 48 h, the treatment for synchronization was applied. To serum-starve cells, cells were washed three times with Hanks' balanced salt solution (HBSS) (GBICO) and cultured in serum-free medium for 72 h. For synchronization at early S phase, cells were treated with 2 mM of thymidine for 18 h twice. Between these two treatments, cells were rinsed with HBSS three times and cultured in normal growth medium to release cell cycle for 9 h. To synchronize cells in the M phase, cells were first treated with 2 mM of thymidine for 24 h. Followed by rinsing with HBSS three times, cells were released with normal growth medium for 3 h. After the short release, cells were treated with 100 ng/ml of microtubule-depolymerizing drug nocodazole for 12 h. For inhibition of Cdk4/6, cells were treated with 10 nM trans-4-((6-(ethylamino)-2-((1-(phenylmethyl)-1H-indol-5-yl)amino)-4-pyrimidinyl)amino)-cyclohexanol (CINK4) Cdk4/6 inhibitor (EMD Chemical) for 24 h, prior to cell cycle and phenotypic analysis.

Flow Cytometry

Our protocol follows that from Current Protocol from Cytometry (Wiley).[21] Briefly, cells were grown in a 10-cm dish for 48 h, then trypsinized, spin down at 1,000 rpm for 5 min, and resuspended in fresh culture medium without any serum. $10^6$ cells/ml were resuspended with a final concentration 5 µg/ml of Hoechst 33342 and incubated for 30 min at room temperature. After incubation, cells were spin down to remove the dye solution, resuspended in fresh culture medium, and then promptly subjected to flow cytometry. The raw data was extracted with FlowJo software (Tree Star Inc., Ashland, Oreg.) and processed with Matlab.

High-Throughput Fluorescence Microscopy

Cells were fixed with 3.7% of formaldehyde (Sigma) for 15 min at room temperature (RT). After fixation, cells were permeabilized with 0.1% Triton X-100 (Sigma) for 10 min and blocked for nonspecific binding with phosphate-buffered saline (PBS) supplemented with 10% of goat serum for 30 min. Cells were incubated with specific concentration of dye diluted from stock solution for 1 h. Nuclear DNA was stained with Hoechst 33342 (Sigma) at 1:40 dilution. Cytoplasm was stained with HCS CellMask Cy5 (Invitrogen) at 1:20000 dilution. Actin was stained with Phalloidin 488 (Invitrogen) at 1:40 dilution. PBS rinse was conducted three times between each step.

Fluorescent images were collected with a Nikon DS-QiMc camera installed on a customized Nikon TE300 microscope with a 10× Plan Fluor lens (N.A. 0.3, Nikon Melville, N.Y.), a motorized stage, and motorized excitation and emission filters (Prior Scientific, Rockland, Mass.) controlled by Nikon NIS Elements. Eighty-one (9-by-9 grid) fields of views were consistently generated using the software Nikon NIS-Elements. The size of the image acquired from the camera was 1280×1024 pixels, and the pixel size was 0.57 µm for a 10× objective. Our ΔX and ΔY for image capture was 662 µm and 520 µm respectively to allow 10% overlay between adjacent fields. The total size of the scanning region (81 images) was ~28.5 mm². Four different channels (UV, GFP, Cy5, and phase contrast) were collected for every field of view. The calibration glass-bottom dish contained dyes for three different fluorescent channels, UV, GFP, and Cy5. For each fluorescence channel, UV, GFP, and Cy5, two calibration images were acquired: with and without illumination. The calibration images were used to reduce the non-uniform illumination of fluorescent images. All of the phenotypic information was calculated with a custom high throughput program (written in Matlab) developed in our laboratory. Typically >1,000 cells were analyzed per different biological repeat (i.e. different cells) for a total >3,000 cells for each tested condition.

Segmentation of Cells and Nuclei

To precisely segment individual cells and nuclei, we used slightly different approaches based on the same principle. For nuclear segmentation, because of the relatively circular shape and relatively even intensity of the Hoechst stain, we filtered calibrated images (as described in the previous section) with a 23×23 pixel normalized Gaussian filter (similar scale as the size of nuclei) and an averaging filter (same size) to obtain $I_G$ (Gaussian intensity) and $I_M$ (averaged intensity). Subtracting $I_M$ from $I_G$ gives $I_N$, the nuclear intensity values without regional background. Empirical testing showed that a threshold setting of 10 was optimal.

Because cells are larger than their nuclei, a larger size of filters was needed. However, one major limitation with spatial domain image filters is non-continuous edges. Increasing the size of the filter increases the size of this "non-trustable" region. The use of a spatial filter 2r+1 in size will lead to the loss of r+1 pixels from the edge because of incomplete information, which greatly reduces the usable image size. For the nucleus, there are only ~12 pixels lost, which is acceptable. For an object the size of the cell, the much larger number of lost pixels is unacceptable. Thus, we did not use any spatial filter to segment individual cells. Rather, images of cells were processed with a 3×3 averaging smoothing filter.

To properly threshold single cell boundaries, measurement and elimination of the background intensity of images is more critical. First, we measured the average, $<I_{BG}>$, and associated standard deviation, $I_{RBG}$, of the background intensity of the smoothed imaged to obtain a set of pixel intensities less than $<I_{BG}>+3.5*I_{RBG}=I_{nn}$. Then, we update the value of $<I_{BG}>$ with $I_{nn}$, $I_{RBG}$, and the standard deviation of $I_{nn}$. Three to five iterations will generally result in stable values of $I_{BG}$ and $I_{RBG}$, which represent the average background intensity value and associated noise in background intensity magnitude, respectively. Next, we use $I_{BG}$ and $I_{RBG}$ to select the signal region of the fluorescence-labeled cells. We define the threshold factor, thc, and select all the pixels in the image with an intensity value larger than $I_{BG}+thc+I_{RBG}$. We make the assumption that the background noise intensity can be described by a Gaussian distribution and then set thc>2, which represents >95% of the background signal will not be selected. Depending on the signal intensity level, the value of thc will range between 2 and 5.

Using the above approach, we determined the cell boundary using phalloidin-stained F-actin images. F-actin usually gives a stronger signal at the cell boundary than at the cell center, differentiating the boundary from the cytoplasm with less bias than a more homogenous dye (such as HCS cell mask) would allow for. In fact, HCS cell mask intensities concentrated around the nucleus—the ticker region of the cell—and decayed towards the edge of the cell; because of the low NA objective, the edge intensity values was blurred, making edge detection very sensitive to bias and sample-to-sample variation.

Eigen-Based Analysis Example

Figure 37:
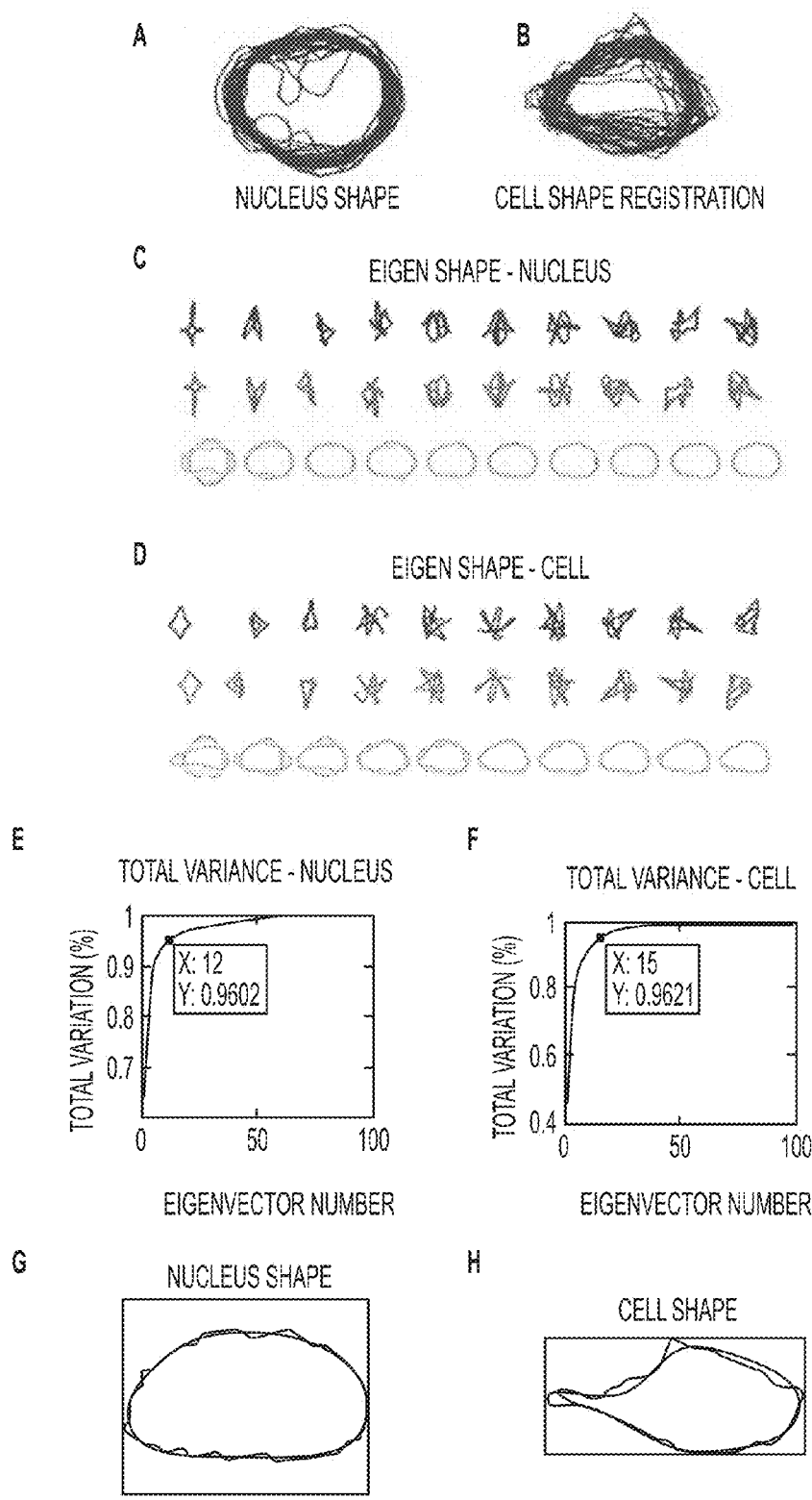
FIG. 37 illustrates eigenshape based analysis of cells according to an embodiment of the current invention.

FIG. 37 illustrates eigenshape based analysis of cells according to an embodiment of the current invention. (A and B). First, nucleus and cell shapes were aligned to eliminate rotational variation and mirror effects. Here we show 50 randomly selected shapes. (C and D). Eigenshapes of nuclei (C) and cell (D) shapes were obtained from principle component analysis. First 10 eigenshapes from nucleus and cell are shown here where top row are eigenshape vector at magnitude of +1 and middle row are eigenshape with magnitude of −1. The effects of each eigenshape vectors were demonstrated in the bottom row and represent how the mean shape of cells is shifted from low to high magnitude of each eigenshapes. (E and F). Total variation among shape along eigenvectors is plotted. For nucleus shape variations, 95% of variation is contributed from the first 12 eigenvectors and the first 16 eigenvectors are covered 95% of variation for cell shaping variation. (G and H). Reconstruction of nucleus shape and cell shape using a low number of eigenvectors agrees well with most of the original shapes.

Figure 38:
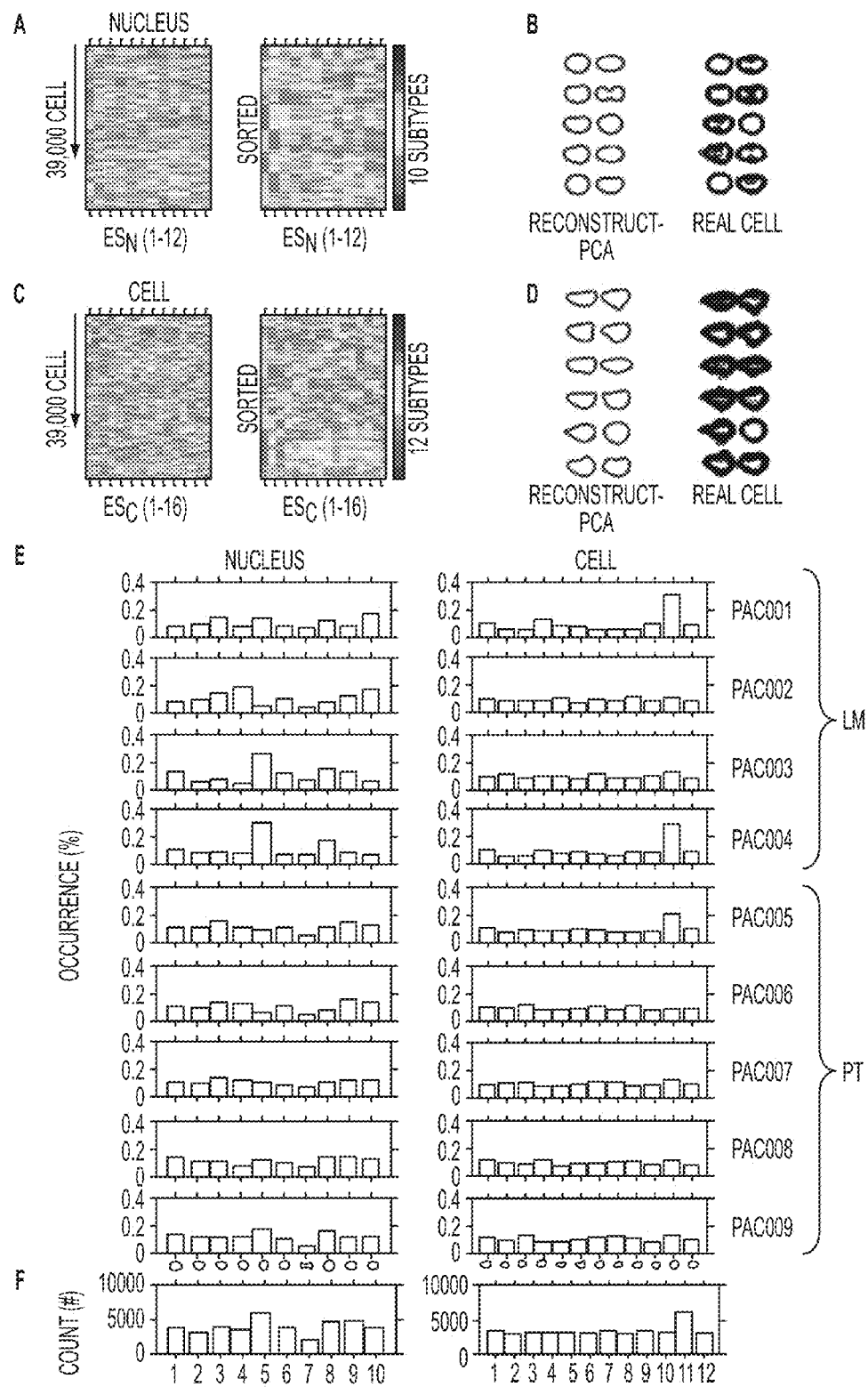
FIGS. 38 and 39 illustrate further eigenshape based analysis of cells according to an embodiment of the current invention.
Figure 39:
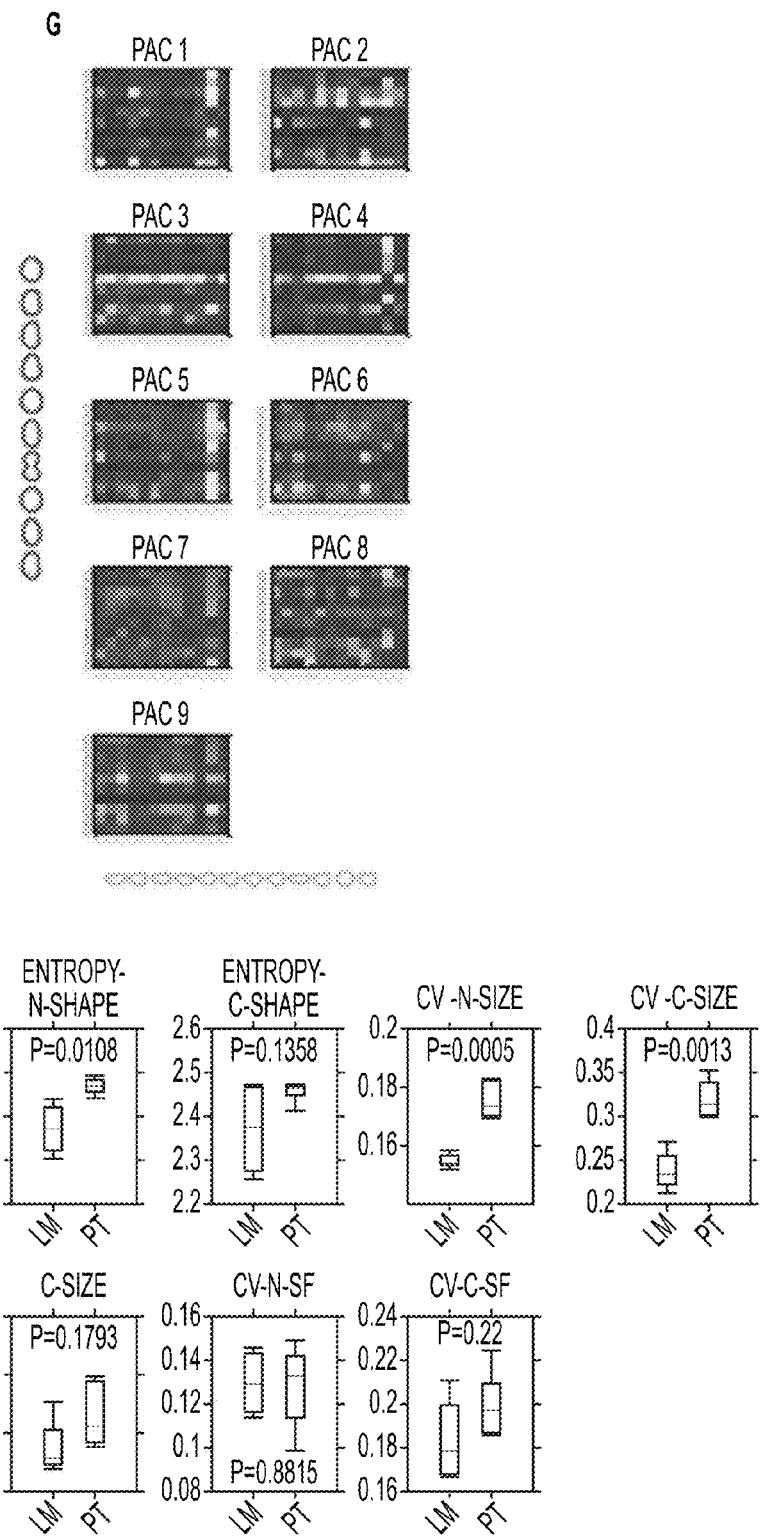

FIGS. 38 and 39 illustrate further eigenshape based analysis of cells according to an embodiment of the current invention. (A). Pancreatic cancer cell nuclei morphology was represented by the first 12 eigenshapes. The normalized magnitude of individual nuclei are shown in the Heatmap (left). K-means clustering method was implemented to identify the subtypes among all cancer cell nuclei. We identified 10 subtypes of cell shape from eigenshape score and the sorted results after k-means clustering was shown in heatmap (right). (B). Representative Nucleus shape (line among left two columns) of each subtype is reconstructed by the mean value of eigenvalue score among this subtype. The variation of shape in each subtype was further highlighted using the standard deviation of eigenvalue score. (C and D). The same procedures are used on cells shapes. (E). Histogram plots of cell population at different subtypes of nucleus and cells from different pancreatic cancer cell lines. (F). Histogram plots show the overall distribution of total number in each subtype. (G). Heat maps show the population distribution at different nucleus and cell subtypes of each cell lines. (H). Entropy of a population distribution was used to assess the heterogeneity of cell lines.

High entropy value represents the population are more equally distributed in each subtypes, i.e. the more heterogeneous. Box plots show entropy of population distribution of nucleus-cell shape and population distribution of nucleus shape from LM cell lines is significantly lower than PT cell lines (top row, the first two plots from left). However, population distribution of cell shape does not show significance between two different types (top row, middle plot). Variation of nucleus size or cell size among LM cell lines, estimated by coefficient variation of scaling factors, also shows significant lower heterogeneous in comparison to PT cell lines (top row, two plots from right). The result is consistent with the shape subtyping analysis and it suggests the morphology of LM cells is more uniform than PT. On the other hand, neither the mean size nor shape factor dispersion of cells or nucleus shows distinct signature between LM and PT.

We claim:

1. A diagnostic device comprising:
a microscope configured to obtain image data on a plurality of cells;
a computing device configured to:
receive the image data;
identify at least a portion of each of the plurality of cells based on the received image data;
determine at least one of a value of a morphological parameter for each identified at least a portion of the plurality of cells or a relative organization among the identified at least a portion of the plurality of cells; and
calculate statistics for the plurality of cells based on the at least one of the determined values of the morphological parameter or the determined relative organization, the statistics including information suitable for distinguishing metastatic cells from non-metastatic cells; and
an output device configured to output the statistics for diagnosis,
wherein said identifying the at least a portion of each of the plurality of cells comprises:
normalizing the image data;
segmenting nuclei of the plurality of cells in the normalized image data; and
identifying the at least a portion of each of the of the plurality of cells based on the segmented nuclei, and
wherein said segmenting nuclei comprises:
obtaining Gaussian intensity image data of the normalized image data;
obtaining averaged intensity image data of the normalized image data;
obtaining nuclear intensity image data based on the difference between the Gaussian intensity image data and the averaged intensity image data; and
segmenting nuclei based on the nuclear intensity image data.

2. The diagnostic device of claim 1, wherein normalizing the image comprises:
obtaining dark image data from the microscope;
obtaining reference illuminated image data from the microscope;
calibrating the image data of the plurality of cells based on the difference between intensities in the image data of the plurality of cells and the dark image data and the difference between intensities in the dark image data and the reference illuminated image data.

3. The diagnostic device of claim 1, further comprising segmenting cell boundaries based on watershed segmentation.

4. The diagnostic device of claim 1, wherein said determining the value of the morphological parameter comprises:
transforming a two-dimensional boundary of the cell and a nucleus of the cell into a one-dimensional curve.

5. The diagnostic device of claim 1, wherein said identifying at least a portion of each of the plurality of cells comprises:
obtaining a total intensity of the plurality of cells in the image data;
obtaining an estimate of average intensity across a cell cycle of the plurality of cells;
obtaining a number of cells in the plurality of cells based on the total intensity and the estimate of average intensity; and
identifying the cells based on the number of cells.

6. A diagnostic device comprising:
a microscope configured to obtain image data on a plurality of cells;
a computing device configured to:
receive the image data;
identify at least a portion of each of the plurality of cells based on the received image data;

determine at least one of a value of a morphological parameter for each identified at least a portion of the plurality of cells or a relative organization among the identified at least a portion of the plurality of cells; and calculate statistics for the plurality of cells based on the at least one of the determined values of the morphological parameter or the determined relative organization, the statistics including information suitable for distinguishing metastatic cells from non-metastatic cells; and an output device configured to output the statistics for diagnosis, wherein said identifying the at least a portion of each of the plurality of cells comprises:
  normalizing the image data;
  segmenting nuclei and cell boundaries of the plurality of cells in the normalized image data; and
  identifying the at least a portion of each of the of the plurality of cells based on the segmented nuclei and the segmented cell boundaries, and
wherein said segmenting cell boundaries comprises:
  obtaining averaged image data of the normalized image data;
  obtaining an average background intensity of the averaged image data;
  obtaining a noise in background intensity magnitude;
  filtering the normalized image data based on the average background intensity and the noise in background intensity magnitude; and
  segmenting cell boundaries based on the filtered normalized image data.

7. The diagnostic device of claim 6, wherein the image data of the plurality of cells comprises first fluorescence channel data and second fluorescence channel data,
  wherein said segmenting nuclei of the cells in the normalized image data is based on the first fluorescence channel data,
  wherein said segmenting cell boundaries in the normalized image data is based on the second fluorescence channel data.

8. A method of characterizing a plurality of cells comprising:
  receiving image data of a plurality of cells;
  identifying at least a portion of each of the plurality of cells in the received image data;
  determining at least one of a value of a morphological parameter for each identified at least a portion of each of the plurality of cells or a relative organization among the identified at least a portion of each of the plurality of cells;
  calculating statistics for the plurality of cells based on the at least one of the determined values of the morphological parameter or the determined relative organization, the statistics including information suitable for distinguishing metastatic cells from non-metastatic cells; and
  outputting the statistics for diagnosis,
  wherein identifying the cell comprises:
    normalizing the image data;
    segmenting nuclei of the plurality of cells in the normalized image data; and
    identifying the at least a portion of each of the plurality of cells based on the segmented nuclei, and
  wherein said segmenting nuclei comprises:
    obtaining Gaussian intensity image data of the normalized image data;
    obtaining averaged intensity image data of the normalized image data;
    obtaining nuclear intensity image data based on the difference between the Gaussian intensity image data and the averaged intensity image data; and
    segmenting nuclei based on the nuclear intensity image data.

9. The method of claim 8, wherein normalizing the image comprises:
  obtaining dark image data from the microscope;
  obtaining reference illuminated image data from the microscope;
  calibrating the image data of the plurality of cells based on the difference between intensities in the image data of the plurality of cells and the dark image data and the difference between intensities in the dark image data and the reference illuminated image data.

10. The method of claim 8, wherein calculating a morphological parameter for the identified cell comprises:
  transforming a two-dimensional boundary of the cell and a nucleus of the cell into a one-dimensional curve.

11. The method of claim 8, wherein identifying the plurality of cells comprises:
  obtaining a total intensity of the plurality of cells in the image data;
  obtaining an estimate of average intensity across a cell cycle of the plurality of cells;
  obtaining a number of cells in the plurality of cells based on the total intensity and the estimate of average intensity; and
  identifying the cells based on the number of cells.

12. A method of characterizing a plurality of cells comprising:
  receiving image data of a plurality of cells;
  identifying at least a portion of each of the plurality of cells in the received image data;
  determining at least one of a value of a morphological parameter for each identified at least a portion of each of the plurality of cells or a relative organization among the identified at least a portion of each of the plurality of cells;
  calculating statistics for the plurality of cells based on the at least one of the determined values of the morphological parameter or the determined relative organization, the statistics including information suitable for distinguishing metastatic cells from non-metastatic cells; and
  outputting the statistics for diagnosis,
  wherein identifying the cell comprises:
    normalizing the image data;
    segmenting nuclei of the plurality of cells in the normalized image data; and
    identifying the at least a portion of each of the plurality of cells based on the segmented nuclei,
  further comprising:
    segmenting cell boundaries of the plurality of cells in the normalized image data; and
    identifying the plurality of cells based on the segmented nuclei and the segmented cell boundaries,
  further comprising:
    segmenting cell boundaries of the plurality of cells in the normalized image data,
    wherein identifying the at least a portion of each of the plurality of cells is based on the segmented nuclei and the segmented cell boundaries, and
  wherein said segmenting cell boundaries comprises:
    obtaining averaged image data of the normalized image data;
    obtaining an average background intensity of the averaged image data;

obtaining a noise in background intensity magnitude;

filtering the normalized image data based on the average background intensity and the noise in background intensity magnitude; and segmenting cell boundaries based on the filtered normalized image data.

13. The method of claim 12, wherein the image data of the plurality of cells comprises first fluorescence channel data and second fluorescence channel data, wherein said segmenting nuclei of the cells in the normalized image data is based on the first fluorescence channel data, wherein said segmenting cell boundaries in the normalized image data is based on the second fluorescence channel data.

* * * * *